US011052137B2

(12) United States Patent
Lavigne et al.

(10) Patent No.: US 11,052,137 B2
(45) Date of Patent: *Jul. 6, 2021

(54) ANTIMICROBIAL AGENTS

(71) Applicants: LYSANDO AG, Triesenberg (LI); KATHOLIEKE UNIVERSITEIT LEUVEN, K.U. LEUVEN R&D, Leuven (BE)

(72) Inventors: Rob Lavigne, Merksem (BE); Stefan Miller, Regensburg (DE); Yves Briers, Rohr AG (CH); Guido Volckaert, Holsbeek (BE); Maarten Walmagh, Herk-de-Stad (BE)

(73) Assignees: LYSANDO AG, Triesenberg (LI); KATHOLIEKE UNIVERSITES LEUVEN, K.U. LEUVEN R&D, Leuven (BE)

( * ) Notice: Subject to any disclaimer, the term of this patent is extended or adjusted under 35 U.S.C. 154(b) by 36 days.

This patent is subject to a terminal disclaimer.

(21) Appl. No.: 16/169,472

(22) Filed: Oct. 24, 2018

(65) Prior Publication Data
US 2019/0209663 A1    Jul. 11, 2019

Related U.S. Application Data

(60) Continuation of application No. 14/535,457, filed on Nov. 7, 2014, now Pat. No. 10,137,175, which is a division of application No. 13/380,312, filed as application No. PCT/EP2010/059146 on Jun. 28, 2010, now Pat. No. 8,906,365.

(30) Foreign Application Priority Data

Jun. 26, 2009 (EP) .................................. 09163953

(51) Int. Cl.
| | |
|---|---|
| *A61K 38/44* | (2006.01) |
| *C07K 14/005* | (2006.01) |
| *C07K 14/47* | (2006.01) |
| *C07K 14/46* | (2006.01) |
| *C12N 1/21* | (2006.01) |
| *C12N 9/36* | (2006.01) |
| *C12N 15/56* | (2006.01) |
| *C07K 19/00* | (2006.01) |
| *A61K 38/47* | (2006.01) |
| *A61L 2/00* | (2006.01) |
| *C12N 15/52* | (2006.01) |
| *C12N 15/62* | (2006.01) |
| *C12N 9/50* | (2006.01) |
| *A61K 38/00* | (2006.01) |

(52) U.S. Cl.
CPC .............. *A61K 38/47* (2013.01); *A61L 2/00* (2013.01); *C07K 14/005* (2013.01); *C07K 14/4723* (2013.01); *C12N 9/2462* (2013.01); *C12N 9/503* (2013.01); *C12N 15/52* (2013.01); *C12N 15/62* (2013.01); *A61K 38/00* (2013.01); *C07K 2319/00* (2013.01); *C07K 2319/20* (2013.01); *C12Y 302/01017* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,985,271 A | 11/1999 | Fischetti et al. | |
| 5,993,809 A | 11/1999 | Weaver et al. | |
| 6,440,935 B1 | 8/2002 | Jaynes | |
| 6,503,881 B2 | 1/2003 | Krieger et al. | |
| 6,936,244 B2 | 8/2005 | Fiochetti et al. | |

(Continued)

FOREIGN PATENT DOCUMENTS

| | | |
|---|---|---|
| DE | 10 2006 061002 | 6/2008 |
| EP | 0 510 907 | 10/1992 |

(Continued)

OTHER PUBLICATIONS

Zanetti et al., Cathelicidin Peptides as Candidates for a Novel Class of Antimicrobials, Curr. Pharma. Design, 2002, 8, 779-93.*

(Continued)

*Primary Examiner* — Robert B Mondesi
*Assistant Examiner* — Todd M Epstein
(74) *Attorney, Agent, or Firm* — Parker Highlander PLLC

(57) ABSTRACT

The application relates to antimicrobial agents against Gram-negative bacteria, in particular to fusion proteins composed of an enzyme having the activity of degrading the cell wall of Gram-negative bacteria and a peptide stretch fused to the enzyme at the N- or C-terminus, as well as pharmaceutical compositions comprising the same. Moreover, it relates to nucleic acid molecules encoding such a fusion protein, vectors comprising said nucleic acid molecules and host cells comprising either said nucleic acid molecules or said vectors. In addition, it relates to such a fusion protein for use as a medicament, in particular for the treatment or prevention of Gram-negative bacterial infections, as diagnostic means or as cosmetic substance. The application also relates to the treatment or prevention of Gram-negative bacterial contamination of foodstuff, of food processing equipment, of food processing plants, of surfaces coming into contact with foodstuff, of medical devices, of surfaces in hospitals and surgeries.

17 Claims, No Drawings
Specification includes a Sequence Listing.

(56) References Cited

U.S. PATENT DOCUMENTS

| | | | |
|---|---|---|---|
| 7,045,677 B2* | 5/2006 | Cottingham | A01K 67/0278 800/14 |
| 7,572,602 B1 | 8/2009 | Donovan | |
| 8,383,102 B2 | 2/2013 | Donovan | |
| 9,388,400 B2 | 7/2016 | Miller et al. | |
| 2002/0127220 A1 | 9/2002 | Fiochetti et al. | |
| 2003/0113298 A1* | 6/2003 | Fischetti | A61K 38/46 424/93.6 |
| 2003/0167477 A1 | 9/2003 | Cottingham | |
| 2006/0034820 A1 | 2/2006 | Lim et al. | |
| 2006/0147442 A1 | 7/2006 | Homan et al. | |
| 2009/0130185 A1 | 5/2009 | Coote et al. | |
| 2010/0092968 A1 | 4/2010 | Beissinger et al. | |

FOREIGN PATENT DOCUMENTS

| | | |
|---|---|---|
| JP | 2012/530510 | 12/2012 |
| WO | WO 94/04688 | 3/1994 |
| WO | WO 96/06532 | 3/1996 |
| WO | WO 00/12528 | 3/2000 |
| WO | WO 2001/000855 | 1/2001 |
| WO | WO 03/089455 | 10/2003 |
| WO | WO 2005/024002 | 3/2005 |
| WO | WO 2005/108563 | 11/2005 |
| WO | WO 2007/022768 | 3/2007 |
| WO | WO 2009/041830 | 4/2009 |
| WO | WO 2009/068858 | 6/2009 |
| WO | WO 2010/011960 | 1/2010 |
| WO | WO 2010/020657 | 2/2010 |
| WO | WO 2010/023207 | 3/2010 |
| WO | WO 2010/091294 | 8/2010 |
| WO | WO 2010/149792 | 12/2010 |
| WO | WO 2010/149795 | 12/2010 |
| WO | WO 2011/023702 | 3/2011 |
| WO | WO 2011/134998 | 11/2011 |

OTHER PUBLICATIONS

Wakamatsu et al., Dimer Structure of Magainin 2 Bound to Phospholipid Vesicles, Biopolymers, 2002, 64, 314-327.*

Conlon et al., Host-defense peptides in skin secretions of African clawed frogs, Gen. Compar. Endocrin., 2012, 176, 513-18.*

Deslouches et al., Activity of the De Novo Engineered Antimicrobial Peptide WLBU2 against Pseudomonas aeruginosa in Human Serum and Whole Blood, Antimicrobial. Chemotherapy, 2005, 49, 3208-16.*

Kashani et al., Recombinant Endolysins as Potential Therapeutics against Antibiotic-Resistant *Staphylococcus aureus*, Clinical Microbiology Rev., 2018, 31, 1-26.*

Yan, Hong, and Robert EW Hancock. "Synergistic interactions between mammalian antimicrobial defense peptides." *Antimicrobial agents and chemotherapy* 45.5 (2001): 1558-1560.

"Amphipathic", English-Russian Thesaurus of Genetic Terms, 1995, cited in corresponding Eurasian Application No. 20100628.

"Antimicrobial peptides", Cited in corresponding Eurasian Application No. 20100628, English translation shown on p. 2.

"Bacteriophages", Cited in corresponding Eurasian Application No. 20100628, English translation shown on p. 2.

"Chain A, Pleruocidin", Accession No. 1Z64_A, accessed from www.ncbi.nlm.nih.gov on Jan. 24, 2019.

"Infection", Great Soviet Encyclopedia, dated 1969-1978. English Translation.

"LYS_BPCP1", EBI accession No. UNITPROT:15057, dated Apr. 1, 1990.

"pET-21-d(+) Vectors", Product Information Sheet, Novagen, 1998.

"PHIKZ144 [Pseudomonas phage phiKZ]", Genbank Accession No. AAL83045.1, downloaded from www.ncbi.nlm.nih.gov, 2002.

Amersham Pharmacia Biotech BioDirectory, p. 94, print 2000.

Amersham Pharmacia Biotech Catalogue, p. 332, print 1998.

Arima et al., "Bactericidal action of lysozymes attached with various sizes of hydrophobic peptides to the C-terminal using genetic modification", *FEBS Lett.*, 415(1):114-8, 1997.

Becker et al., "Th phage K lytic enzyme LysK and lysostaphin act synergistically to kill MRSA", *FEMS Microbiol Lett.*, 287(2):184-91, 2008.

Béven, L., and H. Wroblewski. "Effect of natural amphipathic peptides on viability, membrane potential, cell shape arid motility of mollicutes." *Research in Microbiology* 148.2 (1997): 163-475.

Boehringer Mannheim Biochemicals Catalog, p. 13, print 1996.

Borysowski et al., "Bacteriophage endolysins as a novel class of antibacterial agents", *Exp Biol Med.*, 231:366-377, 2006.

Branden et al., Introduction to Protein Structure, Garland Publishing Inc., New York, p. 247, 1991.

Brändén, Carl-Ivar, and John Tooze. *Introduction to Protein Structure*. Taylor & Francis, 1999.

Brandenburg et al. "Biophysical characterization of lysozyme binging to LPS Re and lipid A", *Eur J Biochem.*, 258: 686-695, 1998.

Briers et al., "A standardized approach for accurate quantification of murein hydrolase activity in high-throughput assays," *J. Biochem. Biophys. Methods*, 70:531-533, 2007.

Briers, Yves, et al. "Muralytic activity and modular structure of the endolysins of Pseudomonas aeruginosa bacteriophages φKZ and EL." *Molecular Microbiology* 65.5 (2007): 1334-1344.

Briers. Yves, et al. "The high-affinity peptidoglycan binding domain of Pseudomonas phage endolysin KZ144." *Biochemical and Biophysical Research Communications* 383.2 (2009): 187-191.

Bülow, Leif, and Klaus Mosbach. "Multienzyme systems obtained by gene fusion," *Trends in Biotechnology* 9.1 (1991): 226-231.

Cheng, Qi, et al. "Removal of group B *Streptococci* colonizing the vagina and oropharynx of mice with a bacteriophage lytic enzyme," *Antimicrobial Agents and Chemotherapy* 49.1 (2005): 111-117.

Conlon, J. Michael, et al. "Peptidomic analysis of skin secretions supports separate species status for the tailed frogs. Ascaphus truei and Ascaphus montanus." *Comparative Biochemistry and Physiology Part D: Genomics and Proteomics* 2.2 (2007): 121-125.

Dawson, Raymond M., and Chun-Qiang Liu. "Cathelicidin peptide SMAP-29: comprehensive review of its properties and potential as a novel class of antibiotics." *Drug Development Research* 70.7 (2009): 481-498.

Deacon, Ashley M., et al. "Protein crystallography using a multilayer monochromator." *Journal of Synchrotron Radiation* 5.3 (1998): 494-496.

Diaz, Eduardo, Rubens Lopez, and Jose L. Garcia, "Chimeric phage-bacterial enzymes: a clue to the modular evolution of genes," *Proceedings of the National Academy of Sciences* 87.20 (1990): 8125-8129.

Diaz, Eduardo, Rubens López, and Jose L. Garcia. "Chimeric pneumococcal cell wall lytic enzymes reveal important physioiogical and evolutionary traits." *Journal of Biological Chemistry* 266.9 (1991): 5464-5471.

Ding, J. L., P. Li, and B. Ho. "The Sushi peptides: structural characterization and mode of action against Gram-negative bacteria." *Cellular and Molecular Life Sciences* 65.7-8 (2008): 1202-1219.

Dmitriev, Boris A., et al. "Tertiary structure of *Staphylococcus aureus* cell wall murein." *Journal of Bacteriology* 186.21 (2004): 7141-7148.

Donovan, David M., et al. "Peptidoglycan hydrolase fusions maintain their parental specificities." *Appl. Environ. Microbiol.* 72.4 (2006): 2988-2996.

Düring, Klaus, et al. "The non-enzymatic microbicidal activity of lysozymes." *FEBS Letters* 449.2-3 (1999): 93-100.

England, Patrick, et al. "Functional characterization of the somatic hypermutation process leading to antibody D1. 3, a high affinity antibody directed against lysozyme." *The Journal of Immunology* 162.4 (1999): 2129-2136.

Falla, Timothy J., D. Nedra Karunaratne, and Robert EW Hancock. "Mode of action of the antimicrobial peptide indolicidin." *Journal of Biological Chemistry* 271.32 (1996): 19298-19303.

Feng, Xuan, Xiaoyan Yang, and Liujiao Bian. "Construction of the recombinant plasmid expressing A novel fusion protein cecropin B human lysozyme." *Biotechnology* 14.6 (2004): 3-5.

(56) References Cited

OTHER PUBLICATIONS

Fischetti, Vincent A. "Bacteriophage endolysins: a novel anti-infective to control Gram-positive pathogens." International Journal of Medical Microbiology 300.6 (2010): 357-362.
Fischetti, Vincent A. "Bacteriophage lysins as effective antibacterials." Current Opinion in Microbiology 11.5 (2008): 393-400.
Fokine, Andrei, et al. "Structure of the bacteriophage φKZ lytic transglycosylase gp144." Journal of Biological Chemistry283.11 (2008): 7242-7250.
Garcia, E. R. N. E. S. T. O., et al. "Molecular evolution of lytic enzymes of Streptococcus pneumoniae and its bacteriophages." Proceedings of the National Academy of Sciences 85.3 (1988): 914-918.
Garlitz, Jennifer A., et al. "Ethylammonium nitrate: a protein crystallization reagent" Acta Crystallographica Section D: Biological Crystallography 55.12 (1999): 2037-2038.
GenBank, Accession No. AAL83015.1, 2002, www.ncbi.nlm.nih.gov.
GenBank, Accession No. AY030242.1, 2001, www.ncbi.nlm.nih.gov.
Graham, Shirley, and Peter J. Coote. "Potent, synergistic inhibition of Staphylococcus aureus upon exposure to a combination of the endopeptidase lysostaphin and the cationic peptide ranalexin." Journal of Antimicrobial Chemotherapy 59.4 (2007): 759-762.
Hancock, Robert EW, and Hans-Georg Sahl. "Antimicrobial and host-defense peptides as new anti-infective therapeutic strategies." Nature biotechnology 24.12 (2006): 1551.
Ibrahim, Hisham R., Takayoshi Aoki, and Antonio Pellegrini. "Strategies for new antimicrobial proteins and peptides: lysozyme and aprotinin as model molecules." Current Pharmaceutical Design 8.9 (2002): 671-693.
Ibrahim, Hisham Radwan, et al. "Enhanced bactericidal action of lysozyme to Escherichia coli by inserting a hydrophobic pentapeptide into its C terminus." Journal of Biological Chemistry 269.7 (1994): 5059-5063.
ICN 2000-2001 catalogue for Cell Culture, p. 41, print 2000.
Invitrogen, pEXP5-NT/TOPO® and pEXP5-CT/TOPO® TA Expression Kits, 2006.
Ito, Yoshihiro, et al. "Bactericidal activity of human lysozymes carrying various lengths of polyproline chain at the C-terminus." FEBS letters 415.3 (1997): 285-288.
Jado, Isabel, et al. "Phage lytic enzymes as therapy for antibiotic-resistant Streptococcus pneumoniaeinfection in a murine sepsis model." Journal of Antimicrobial Chemotherapy52.6 (2003): 967-973.
Leitch, E. C., and M. D. P. Willcox. "Synergic antistaphylococcal properties of lactoferrin and lysozyme." Journal of Medical Microbiology 47.9 (1998): 837-842.
Li, Qingtian, et al. "Potential therapeutic efficacy of a bactericidal—immunomodulatory fusion peptide against methicillin-resistant Staphylococcus aureus skin infection." Applied Microbiology and Biotechnology 86.1 (2010): 305-309.
Loeffler, Jutta M., Daniel Nelson, and Vincent A. Fischetti. "Rapid killing of Streptococcus pneumaniae with a bacteriophage cell wall hydrolase." Science 294.5549 (2001): 2170-2172.
Loessner, Martin J. "Bacteriophage endolysins—current state of research and applications." Current Opinion in Microbiology8.4 (2005); 480-487.
López, Rubens, Ernesto Garcia, and Pedro Garcia. "Enzymes for anti-infective therapy: phage lysins." Drug Discovery Today: Therapeutic Strategies 1.4 (2004): 469-474.
Lowenberger, Carl, et al. "Antimicrobial activity spectrum, cDNA cloning, and mRNA expression of a newly isolated member of the cecropin family from the mosquito vector Aedes aegypti." Journal of Biological Chemistry 274.29 (1999): 20092-20097.
Lu, Xue-mei, et al. "Expression of the antimicrobial peptide cecropin fused with human lysozyme inEscherichia coli." Applied Microbiology and Biotechnology 87.6 (2010): 2169-2176.

Maloy, W. Lee, and U. Prasad Kari "Structure—activity studies on magainins and other host defense peptides." Biopolymers: Original Research on Biomolecules 37.2 (1995): 105-122.
Manoharadas, Salim, Angela Witte, and Udo Bläsi. "Antimicrobial activity of a chimeric enzybiotic towards Staphylococcus aureus." Journal of Biotechnology 139.1 (2009): 118-123.
Matthews, B. W., and S. J. Remington. "The three dimensional structure of the lysozyme from bacteriophage T4." Proceedings of the National Academy of Sciences 71.10 (1974): 4178-4182.
Melo, Manuel N., Rafael Ferre, and Miguel Arb Castanho. "Antimicrobial peptides: linking partition, activity and high membrane-bound concentrations." Nature Reviews Microbiology 7.3 (2009): 245.
Merck KGaA Catalogue, p. 819, print 1996.
Merk, Helmut, et al. "Cell-free expression of two single-chain monoclonal antibodies against lysozyme: effect of domain arrangement on the expression." The Journal of Biochemistry125.2 (1999): 328-333.
Morita, Masatomo, et al. "Functional analysis of antibacterial activity of Bacillus amyloliquefaciens phage endolysin against Gram-negative bacteria." FEBS Letters 500.1-2 (2001): 56-59.
Muyombwe, Anthony, Yasunori Tanji, and Hajime Unno. "Cloning and expression of a gene encoding the lytic functions of Bacillus amyloliquefaciens phage: evidence of an auxiliary lysis system." Journal of Bioscience and Bioengineering 88.2 (1999): 221-225.
Nelson, Daniel, Lawrence Loomis, and Vincent A. Fischetti. "Prevention and elimination of upper respiratory, colonization of mice by group A Streptococci by using a bacteriophage lytic enzyme." Proceedings of the National Academy of Sciences 98.7 (2001): 4107-4112.
Niu, Mingfu, et al. "The molecular design of a recombinant antimicrobial peptide CP and its in vitro activity." Protein Expression and Purification 57.1 (2008): 95-100.
Oncor Appligene 1996-1997 Catalogue, p. 201, print 1996.
Orito, Y., et al. "Bacillus amyloliquefaciens phage endolysin can enhance permeability of Pseudomonas aeruginosa outer membrane and induce cell lysis." Applied Microbiology and Biotechnology 65.1 (2004): 105-109.
Park, In Yup, et al. "Parasin I, an antimicrobial peptide derived from histone H2A in the catfish, Parasilurus asotus." FEBS letters 437.3 (1998): 258-262.
Park, Taehyun, et al. "Topological dynamics of holins in programmed bacterial lysis." Proceedings of the National Academy of Sciences 103.52 (2006): 19713-19718.
PCT International Search Report and Written Opinion issued in International application No. PCT/EP2010/059146, dated Dec. 14, 2010.
PCT International Search Report on Patentability issued in International application No. PCT/EP2010/0591146, dated Jan. 12, 2012.
pET-32a-c(+) Vectors, Product Insert, Novagen, 1998.
Powers, Jon-Paul S., and Robert EW Hancock. "The relationship between peptide structure and antibacterial activity," Peptides 24.11 (2003): 1681-1691.
Rashel, Mohammad, et al. "Efficient elimination of multidrug-resistant Staphylococcus aureus by cloned lysin derived from bacteriophage φMR11." The Journal of Infectious Diseases 196.8 (2007): 1237-1247.
Reimann, C. T., et al. "Proteins in vacuo: a molecular dynamics study of the unfolding behavior of highly charged disulfide-bond-intact lysozyme subjected to a temperature pulse." Physical Review E 60.6 (1999): 7277.
Ruckenstein, Eli, and Xianfang Zeng. "Macroporous chitin affinity membranes for lysozyme separation." Biotechnology and Bioengineering 56.6 (1997): 610-617.
Sadowski, M. I., and D. T. Jones. "The sequence-structure relationship and protein function prediction." Current Opinion in Structural Biology 19.3 (2009): 357-362.
Sanz, Jesús M., and José L. Garcia. "Structural studies of the lysozyme coded by the pneumococcal phage Cp-1: Conformational changes induced by choline." European Journal of Biochemistry 187.2 (1990): 409-416.

(56) References Cited

OTHER PUBLICATIONS

Schuch, Raymond, Daniel Nelson, and Vincent A. Fischetti. "A bacteriolytic agent that detects and kills Bacillus anthracis." *Nature* 418.6900 (2002): 884.

Seffernick. Jennifer L., et al. "Melamine deaminase and atrazine chlorohydrolase: 98 percent identical but functionally different." *Journal of Bacteriology* 183.8 (2001): 2405-2410.

Steiner, H., et al. "Sequence d specificity of two antibacterial proteins involved in insect immunity." *Nature* 292.5820 (1981): 246.

Stojković, Emina A., and Lucia B. Rothman-Denes. "Coliphage N4 N-acetylmuramidase defines a new family of murein hydrolases." *Journal of Molecular Biology* 366.2 (2007): 406-419.

Tack, Brian F., et al, "SMAP-29 has two LPS-binding sites and a central hinge." *European Journal of Biochemistry* 269.4 (2002): 1181-1189.

Tan, Nguan Soon, et al. "Definition of endotoxin binding sites in horseshoe crab thctor C recombinant sushi proteins and neutralization of endotoxin by sushi peptides." *The FASEB Journal* 14.12 (2000): 1801-1813.

Terpe, K. "Overview of tag protein fusions: from molecular and biochemical fundamentals to commercial systems." *Applied Microbiology and Biotechnology* 60.5 (2003): 523-533.

Tossi, Alessandro, Luca Sandri, and Anna Giangaspero. "Amphipathic, α-helical antimicrobial peptides." *Peptide Science* 55.1 (2000): 4-30.

UniProt Database, "Lactotransferrin," P02788, 2014.

Van der Linden, Danitsja S., et al. "Synergistic effects of ovine-derived cathelicidins and other antimicrobials against *Escherichia coli* O157: H7 and *Staphylococcus aureus* 1056 MRSA." *Biotechnology Letters* 31.8 (2009): 1265-1267.

Vollmer, Waldemar, et al. "Bacterial peptidoglycan (murein) hydrolases." *FEMS Microbiology Reviews* 32.2 (2008): 259-286.

Wilcox; Sara. "The new antimicrobials: cationic peptides." *BioTeach Journal* 2 (2004): 88-91.

Witkowski, Andrzej, et al. "Conversion of a β-ketoacyl synthase to a malonyl decarboxylase by replacement of the active-site cysteine with glutamine." *Biochemistry* 38.36 (1999): 11643-11650.

Yan, Lizhen, and Michael E. Adams. "Lycotoxins, antimicrobial peptides from venom of the wolf spiderLycosa carolinensis." *Journal of Biological Chemistry* 273.4 (1998): 2059-2066.

Zasloff, Michael. "Antimicrobial peptides of multicellular organisms," *Nature* 415.6870 (2002): 389.

Zhen, Y. S. "Anticancer Drug Research and Development." (2004): 442-455.

Zhou, Liangfan, et al. "TrxA mediating fusion expression of antimicrobial peptide CM4 from multiple joined genes in *Escherichia coli*." *Protein Expression and Purification* 64.2 (2009): 225-230.

Loomans et al., "Histidine-based zinc-binding sequences and the antimicrobial activity of calprotectin." *The Journal of infectious diseases* 177.3 (1998): 812-814.

UniProt Database Accession No. Q6Y7T6, Oct. 2008. 1 page.

\* cited by examiner

ANTIMICROBIAL AGENTS

This application is a continuation of U.S. application Ser. No. 14/535,457, now U.S. Pat. No. 10,137,175, filed Nov. 7, 2014, which is a divisional of U.S. application Ser. No. 13/380,312, now U.S. Pat. No. 8,906,365, filed Mar. 9, 2012, as a national phase application under 35 U.S.C. § 371 of International Application No. PCT/EP2010/059146 filed Jun. 28, 2010, which claims priority to European Application No. 09163953.4, filed on Jun. 26, 2009. The entire text of each of the above-referenced disclosures is specifically incorporated herein by reference without disclaimer.

BACKGROUND OF THE INVENTION

1. Field of the Invention

The present invention relates to antimicrobial agents against Gram-negative bacteria, in particular to fusion proteins composed of an enzyme having the activity of degrading the cell wall of Gram-negative bacteria and an additional peptide stretch fused to the enzyme on the N- or C-terminus. Moreover, the present invention relates to nucleic acid molecules encoding said fusion protein, vectors comprising said nucleic acid molecules and host cells comprising either said nucleic acid molecules or said vectors. In addition, the present invention relates to said fusion protein for use as a medicament, in particular for the treatment or prevention of Gram-negative bacterial infections, as diagnostic means or as cosmetic substance. The present invention also relates to the treatment or prevention of Gram-negative bacterial contamination of foodstuff, of food processing equipment, of food processing plants, of surfaces coming into contact with foodstuff, of medical devices, of surfaces in hospitals and surgeries. Furthermore, the present invention relates to pharmaceutical or cosmetic compositions comprising said fusion protein.

2. Description of Related Art

Gram-negative bacteria possess an outer membrane, with its characteristic asymmetric bilayer as a hallmark. The outer membrane bilayer consists of an inner monolayer containing phospholipids (primarily phosphatidyl ethanolamine) and an outer monolayer that is mainly composed of a single glycolipid, lipopolysaccharide (LPS). There is an immense diversity of LPS structures in the bacterial kingdom and the LPS structure may be modified in response to prevailing environmental conditions. The stability of the LPS layer and interaction between different LPS molecules is mainly achieved by the electrostatic interaction of divalent ions ($Mg^{2+}$, $Ca^{2+}$) with the anionic components of the LPS molecule (phosphate groups in the lipid A and the inner core and carboxyl groups of KDO). Furthermore, the dense and ordered packing of the hydrophobic moiety of lipid A, favored by the absence of unsaturated fatty acids, forms a rigid structure with high viscosity. This makes it less permeable for lipophilic molecules and confers additional stability to the outer membrane (OM).

Various types of agents having bactericidal or bacteriostatic activity are known, e.g. antibiotics, endolysins, antimicrobial peptides and defensins. Increasingly microbial resistance to antibiotics, however, is creating difficulties in treating more and more infections caused by bacteria. Particular difficulties arise with infections caused by Gram-negative bacteria like *Pseudomonas aeruginosa* and Enterobacteriaceae.

Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. They are either β(1,4)-glycosylases (lysozymes), transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage C1 endolysin towards group A streptococci (Nelson et al., 2001). Since then many publications have established endolysins as an attractive and complementary alternative to control bacterial infections, particularly by Gram positive bacteria. Subsequently different endolysins against other Gram positive pathogens such as *Streptococcus pneumoniae* (Loeffler et al., 2001), *Bacillus anthracis* (Schuch et al., 2002), *S. agalactiae* (Cheng et al., 2005) and *Staphylococcus aureus* (Rashel et al, 2007) have proven their efficacy as enzybiotics. Nowadays, the most important challenge of endolysin therapy lies in the insensitivity of Gram-negative bacteria towards the exogenous action of endolysins, since the outer membrane shields the access of endolysins from the peptidoglycan. This currently prevents the expansion of the range of effective endolysins to important Gram-negative pathogens.

Antimicrobial peptides (AMPs) represent a wide range of short, cationic, gene encoded peptide antibiotics that can be found in virtually every organism. Different AMPs display different properties, and many peptides in this class are being intensively researched not only as antibiotics, but also as templates for cell penetrating peptides. Despite sharing a few common features (e.g., cationicity, amphipathicity and short size), AMP sequences vary greatly, and at least four structural groups (α-helical, β-sheet, extended and looped) have been proposed to accommodate the diversity of the observed AMP conformations. Likewise, several modes of action as antibiotics have been proposed, and it was shown e.g. that the primary target of many of these peptides is the cell membrane whereas for other peptides the primary target is cytoplasmic invasion and disruption of core metabolic functions. AMPs may become concentrated enough to exhibit cooperative activity despite the absence of specific target binding; for example, by forming a pore in the membrane, as is the case for most AMPs. However, this phenomenon has only been observed in model phospholipid bilayers, and in some cases, AMP concentrations in the membrane that were as high as one peptide molecule per six phospholipid molecules were required for these events to occur. These concentrations are close to, if not at, full membrane saturation. As the minimum inhibitory concentration (MIC) for AMPs are typically in the low micromolar range, scepticism has understandably arisen regarding the relevance of these thresholds and their importance in vivo (Melo et al., Nature reviews, Microbiology, 2009, 245).

Defensins are a large family of small, cationic, cysteine- and arginine-rich antimicrobial peptides, found in both vertebrates and invertebrates. Defensins are divided into five groups according to the spacing pattern of cysteines: plant, invertebrate, α-, β-, and θ-defensins. The latter three are mostly found in mammals. α-defensins are proteins found in neutrophils and intestinal epithelia. β-defensins are the most widely distributed and are secreted by leukocytes and epithelial cells of many kinds. θ-defensins have been rarely found so far e.g. in leukocytes of rhesus macaques. Defensins are active against bacteria, fungi and many enveloped and nonenveloped viruses. However, the concentrations needed for efficient killing of bacteria are mostly high, i.e. in the µ-molar range. Activity of many peptides may be limited in presence of physiological salt conditions, divalent cations and serum. Depending on the content of hydrophobic amino acid residues Defensins also show haemolytic activity.

SUMMARY OF THE INVENTION

Thus, there is a need for new antimicrobial agents.

This object is solved by the subject matter defined in the claims.

The term "protein" as used herein refers synonymously to the term "polypeptide". The term "protein" as used herein refers to a linear polymer of amino acid residues linked by peptide bonds in a specific sequence. The amino-acid residues of a protein may be modified by e.g. covalent attachments of various groups such as carbohydrates and phosphate. Other substances may be more loosely associated with the polypeptide chains, such as heme or lipid, giving rise to the conjugated proteins which are also comprised by the term "protein" as used herein. The various ways in which the polypeptide chains fold have been elucidated, in particular with regard to the presence of alpha helices and beta-pleated sheets. The term "protein" as used herein refers to all four classes of proteins being all-alpha, all-beta, alpha/beta and alpha plus beta. Moreover, the term "protein" refers to a complex, wherein the complex refers to a homomer.

The term "fusion protein" as used herein refers to an expression product resulting from the fusion of two nucleic acid sequences. Such a protein may be produced, e.g., in recombinant DNA expression systems. Moreover, the term "fusion protein" as used herein refers to a fusion of a first amino acid sequence as e.g. an enzyme, with a second or further amino acid sequence. The second or further amino acid sequence may define a domain or any kind of peptide stretch. Preferably, said second and/or further amino acid sequence is foreign to and not substantially homologous with any domain of the first amino acid sequence.

The term "peptide stretch" as used herein refers to any kind of peptide linked to a protein such as an enzyme.

The term "peptide" as used herein refers to short polypeptides consisting of from about 2 to about 100 amino acid residues, more preferably from about 4 to about 50 amino acid residues, more preferably to about 5 to 30 amino acid residues, wherein the amino group of one amino acid residue is linked to the carboxyl group of another amino acid residue by a peptide bond. A peptide may have a specific function. A peptide can be a naturally occurring peptide or a synthetically designed and produced peptide. The peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)).

Examples of naturally occurring peptides are antimicrobial peptides, defensins, sushi peptides. Examples of synthetically produced peptides are polycationic, amphiphatic or hydrophobic peptides. A peptide in the meaning of the present invention does not refer to His-tags, Strep-tags, thioredoxin or maltose binding proteins (MBP) or the like, which are used to purify or locate proteins.

The term "endolysin" as used herein refers to an enzyme which is suitable to hydrolyse bacterial cell walls. "Endolysins" comprise of at least one "enzymatically active domain" (EAD) having at least one of the following activities: endopeptidase, chitinase, T4 like muraminidase, lambda like muraminidase, N-acetyl-muramoyl-L-alanine-amidase (amidase), muramoyl-L-alanine-amidase, muramidase, lytic transglycosylase (C), lytic transglycosylase (M), N-acetyl-muramidase, N-acetyl-glucosaminidase (lysozyme) or transglycosylases as e.g. KZ144 and EL188. In addition, the endolysins may contain also regions which are enzymatically inactive, and bind to the cell wall of the host bacteria, the so-called CBDs (cell wall binding domains).

The term "EAD" as used herein refers to the enzymatically active domain of an endolysin. The EAD is responsible for hydrolysing bacterial peptidoglycans. It exhibits at least one enzymatic activity of an endolysin. The EAD can also be composed of more than one enzymatically active module.

The term "autolysins" refers to enzymes related to endolysins but encoded by bacteria and involved in e.g. cell division. An overview of autolysins can be found in "Bacterial peptidoglycan (murein) hydrolases. Vollmer W, Joris B, Charlier P, Foster S. FEMS Microbiol Rev. 2008 March; 32(2):259-86".

The term "bacteriocin" as used herein refers to protein-like, polypeptide-like or peptide-like substances which are able to inhibit the growth of other bacteria. Preferably said inhibition is specifically by means of absorption of said other bacteria to specific receptors of the bacteriocin. In general, bacteriocins are produced by microorganisms. However, the term "bacteriocin" as used herein refers both to an isolated form by a microorganism or to a synthetically produced form, and refers also to variants which substantially retain the activities of their parent bacteriocins, but whose sequences have been altered by insertion or deletion of one or more amino acid residues.

The term, "antimicrobial peptide" (AMP) as used herein refers to any peptide that has microbiocidal and/or microbiostatic activity. Thus, the term "antimicrobial peptide" as used herein refers in particular to any peptide having antibacterial, anti-fungal, anti-mycotic, anti-parasitic, anti-protozoal, anti-viral, anti-infectious, anti-infective and/or germicidal, algicidal, amoebicidal, microbiocidal, bacteriocidal, fungicidal, parasiticidal, protozoacidal, protozoicidal properties.

The term "defensin" as used herein refers to a peptide present within animals, preferably mammals, more preferably humans, wherein the defensin plays a role in the innate host defense system as the destruction of foreign substances such as infectious bacteria and/or infectious viruses and/or fungi. A defensin is a non-antibody microbicidal and/or tumoricidal protein, peptide or polypeptide. Examples for "defensins" are "mammalian defensins," alpha-defensins, beta-defensins, indolicidin and magainins. The term "defensins" as used herein refers both to an isolated form from animal cells or to a synthetically produced form, and refers also to variants which substantially retain the cytotoxic activities of their parent proteins, but whose sequences have been altered by insertion or deletion of one or more amino acid residues.

The term "sushi peptide" as used herein refers to complement control proteins (CCP) having short consensus repeats. The sushi module of sushi peptides functions as a protein-protein interaction domain in many different proteins. Peptides containing a Sushi domain have been shown to have antimicrobial activities.

As used herein, the term "cationic peptide" refers to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. Examples of naturally occurring cationic peptides which can be recombinantly produced are defensins, magainins, melittin and cecropins.

The term "polycationic peptide" as used herein refers to a synthetically produced peptide composed of mostly lysine and/or arginine residues.

The term "amphipathic peptide" as used herein refers to peptides having both hydrophilic and hydrophobic functional groups. Preferably, the term "amphipathic peptide" as used herein refers to a peptide having a defined arrangement of hydrophilic and hydrophobic groups e.g. amphipatic peptides may be e.g. alpha helical, having predominantly non polar side chains along one side of the helix and polar residues along the remainder of its surface.

The term "hydrophobic group" as used herein refers to chemical groups such as amino acid side chains which are substantially water insoluble, but soluble in an oil phase, with the solubility in the oil phase being higher than that in water or in an aqueous phase. In water, amino acids having a hydrophobic side chain interact with one another to generate a nonaqueous environment. Examples of amino acids with hydrophobic side chains are alanine, valine, leucine, isoleucine, phenylalanine, histidine, tryptophane and tyrosine.

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence.

The term "substitution" as used herein refers to the exchange of an amino acid residue located at a certain position for a different one.

The present invention relates to new antibacterial agents against Gram-negative bacteria, in particular to fusion proteins composed of an enzyme having the activity of degrading the cell wall of Gram-negative bacteria and a peptide stretch fused to the enzyme on the N- or C-terminus or at both termini.

In one aspect of the present invention the enzyme having the activity of degrading the cell wall of Gram-negative bacteria is an endolysin, autolysin or bacteriocin.

In another aspect of the present invention the enzyme according to the present invention may further comprise regions which are enzymatically inactive, and bind to the cell wall of the host bacteria, the so-called CBDs (cell wall binding domains).

Preferred fusion proteins according to the present invention are depicted in SEQ ID NO:36 to 63. The fusion proteins according to SEQ ID NO:36 to 63 may comprise one or more additional amino acid residues on the N-terminus. Preferably the additional amino acid residue is methionine.

Preferably, the endolysin is encoded by bacteriophages specific for Gram-negative bacteria such as Gram-negative bacteria of bacterial groups, families, genera or species comprising strains pathogenic for humans or animals like Enterobacteriaceae (*Escherichia*, especially *E. coli*, *Salmonella*, *Shigella*, *Citrobacter*, *Edwardsiella*, *Enterobacter*, *Hafnia*, *Klebsiella*, especially *K. pneumoniae*, *Morganella*, *Proteus*, *Providencia*, *Serratia*, *Yersinia*), Pseudomonadaceae (*Pseudomonas*, especially *P. aeruginosa*, *Burkholderia*, *Stenotrophomonas*, *Shewanella*, *Sphingomonas*, *Comamonas*), *Neisseria*, *Moraxella*, *Vibrio*, *Aeromonas*, *Brucella*, *Francisella*, *Bordetella*, *Legionella*, *Bartonella*, *Coxiella*, *Haemophilus*, *Pasteurella*, *Mannheimia*, *Actinobacillus*, *Gardnerella*, Spirochaetaceae (*Treponema* and *Borrelia*), Leptospiraceae, *Campylobacter*, *Helicobacter*, *Spirillum*, *Streptobacillus*, Bacteroidaceae (*Bacteroides*, *Fusobacterium*, *Prevotella*, *Porphyromonas*), *Acinetobacter*, especially *A. baumanii*.

Preferably, the autolysin is encoded by Gram-negative bacteria such as Gram-negative bacteria of bacterial groups, families, genera or species comprising strains pathogenic for humans or animals like Enterobacteriaceae (*Escherichia*, especially *E. coli*, *Salmonella*, *Shigella*, *Citrobacter*, *Edwardsiella*, *Enterobacter*, *Hafnia*, *Klebsiella*, especially *K. pneumoniae*, *Morganella*, *Proteus*, *Providencia*, *Serratia*, *Yersinia*), Pseudomonadaceae (*Pseudomonas*, especially *P. aeruginosa*, *Burkholderia*, *Stenotrophomonas*, *Shewanella*, *Sphingomonas*, *Comamonas*), *Neisseria*, *Moraxella*, *Vibrio*, *Aeromonas*, *Brucella*, *Francisella*, *Bordetella*, *Legionella*, *Bartonella*, *Coxiella*, *Haemophilus*, *Pasteurella*, *Mannheimia*, *Actinobacillus*, *Gardnerella*, Spirochaetaceae (*Treponema* and *Borrelia*), Leptospiraceae, *Campylobacter*, *Helicobacter*, *Spirillum*, *Streptobacillus*, Bacteroidaceae (*Bacteroides*, *Fusobacterium*, *Prevotella*, *Porphyromonas*), *Acinetobacter*, especially *A. baumanii*.

The bacteriocin is preferably specific for Gram-negative bacteria as listed above, but may also be less specific.

The enzyme according to the present invention has cell wall degrading activity against Gram-negative bacteria of bacterial groups, families, genera or species comprising strains pathogenic for humans or animals like Enterobacteriaceae (*Escherichia*, especially *E. coli*, *Salmonella*, *Shigella*, *Citrobacter*, *Edwardsiella*, *Enterobacter*, *Hafnia*, *Klebsiella*, especially *K. pneumoniae*, *Morganella*, *Proteus*, *Providencia*, *Serratia*, *Yersinia*), Pseudomonadaceae (*Pseudomonas*, especially *P. aeruginosa*, *Burkholderia*, *Stenotrophomonas*, *Shewanella*, *Sphingomonas*, *Comamonas*), *Neisseria*, *Moraxella*, *Vibrio*, *Aeromonas*, *Brucella*, *Francisella*, *Bordetella*, *Legionella*, *Bartonella*, *Coxiella*, *Haemophilus*, *Pasteurella*, *Mannheimia*, *Actinobacillus*, *Gardnerella*, Spirochaetaceae (*Treponema* and *Borrelia*), Leptospiraceae, *Campylobacter*, *Helicobacter*, *Spirillum*, *Streptobacillus*, Bacteroidaceae (*Bacteroides*, *Fusobacterium*, *Prevotella*, *Porphyromonas*), *Acinetobacter*, especially *A. baumanii*.

Specific examples of an endolysin part derived from a phage or that is a wild type endolysin are depicted in the following table:

TABLE 1

| phage | publication | Wild type endolysin | predicted function of the endolysin |
|---|---|---|---|
| ΦV10 | Perry, L. L. and Applegate, B. M. | PhiV10p30 | chitinase |
| FELS-1 | McClelland, M. and Wilson, R. K. | STM0907.Fels0 | chitinase |
| ε15 | Kropinksi, A. M. and McConnel, M. R. | epsilon15p25 | chitinase |
| YUA | Ceyssens. P. (Laboratory for Gene technology) | YuA20 | lytic transglycosylase (C)/1 transmembranair domain (N) |
| B3 | Braid, M. D. and Kitts, C. L. | ORF23 | lytic transglycosylase (C)/2 transmembranair domains (N) |
| BCEPμ | Summer, E. J. and Young, R. | BcepMu22 | lytic transglycosylase (M)/1 transmembranair domain (N) |
| F116 | Byrne, M. and Kropinski, A. M. | F116p62 | muraminidase (T4-like) |
| FELS-2 | McClelland, M. and Wilson, R. K. | STM2715.S.Fels2 | muraminidase (T4-like) |
| ES18 | Casjens, S. R. and Hendrix, R. W. | gp76 | muraminidase (T4-like) |
| SETP3 | De Lappe, N and Cormican, M. | SPSV3_gp23 | muraminidase (T4-like) |
| ΦECO32 | Savalia, D and Severinov, K | phi32_17 | muraminidase (T4-like) |
| HK022 | Juhala, R and Hendrix, R. W. | HK022p54 | muraminidase (lambdalike) |
| HK97 | Juhala, R and Hendrix, R. W. | HK97p58 | muraminidase (lambdalike) |
| HK620 | Clark, A. J. and Dhillon, T. S. | HK620p36 | muraminidase (lambdalike) |
| E1 | Pickard, D. and Dougan, G | VIP0007 | muraminidase (lambdalike) |
| SF6 | Casjens, S and Clark, A. J. | Sf6p62 | muraminidase (lambdalike) |
| SFV | Allison, G. E. and Verma, N. K. | R (SfVp40) | muraminidase (lambdalike) |
| BCEPC6B | Summer, E J and Young, R. | gp22 | muraminidase (lambdalike) |
| BCEPNAZGUL | Summer, E J and Young, R. | Nazgul38 | muraminidase (lambdalike) |
| P2 | Christie, G. E. and Calender, R. | K (P2p09) | muraminidase (lambdalike) |
| WΦ | Christie, G. E. and Esposito, D. | K (Wphi09) | muraminidase (lambdalike) |
| RV5 | Kropinski, A. M. and Johnson | rv5_gp085 | muraminidase (lambdalike) |
| JS98 | Zuber, S and Denou, E. | EpJS98_gp116 | muraminidase (T4-like) |
| 13A | Savalia, D and Molineux, I. | gp3.5 | muramoyl-L-alanine amidase |
| BA14 | Savalia, D and Molineux, I. | gp3.5 | muramoyl-L-alanine amidase |
| ECODS1 | Savalia, D and Molineux, I. | gp3.5 | muramoyl-L-alanine amidase |
| K1F | Scholl, D and Merril, C | CKV1F_gp16 | muramoyl-L-alanine amidase |
| T3 | Pajunen, M. I. and Mollineux, I. J. | T3p18 | muramoyl-L-alanine amidase |
| GH-1 | Kropinski, A. M. and Kovalyova, I. V. | gh-1p12 | muramoyl-L-alanine amidase |
| K11 | Molineux, I. and Savalia, D. | gp3.5 | muramoyl-L-alanine amidase |
| ΦCTX | Nakayama, K and Hayashi, T. | ORF12 | PG-binding domain (N)/muramidase (C) |
| BCEP43 | Summer, E J and Young, R. | Bcep43-27 | PG-binding domain (N)/muramidase (C) |
| BCEP781 | Summer, E J and Young, R. | Bcep781-27 | PG-binding domain (N)/muramidase (C) |
| BCEP1 | Summer, E J and Young, R. | Bcep1-28 | PG-binding domain (N)/muramidase (C) |
| BCEPNY3 | Summer, E J and Young, R. | BcepNY3gene26 | PG-binding domain (N)/muramidase (C) |
| ΦE12-2 | DeShazer, D and Nierman, W. C. | gp45 | PG-binding domain (N)/muramidase (C) |
| Φ52237 | DeShazer, D and Nierman, W. C. | gp28 | PG-binding domain (N)/muramidase (C) |
| ΦP27 | Recktenwald, J and Schmidt, H. | P27p30 | endopeptidase |
| RB49 | Monod, C and Krisch, H. M. | RB49p102 | endopeptidase |
| Φ1 | Arbiol, C. and Comeau, A. M. | phi1-p102 | endopeptidase |
| T5 | Pankova, N. V. and Ksenzenko, V. N. | lys (T5.040) | endopeptidase |
| 201phi2-1 | Thomas et al., 2008 | | PG-binding domain (N)/unknown catalytic domain (C) |
| Aeh1 | Monod, C and Krisch, H. M. | Aeh1p339 | muraminidase (T4-like) |
| YYZ-2008 | Kropinski, A. M. | YYZgp45 | muraminidase (lambda-like) |

Also preferred is the endolysin part deriving from endolysins of the *Pseudomonas aeruginosa* phages ΦKZ and EL, of the *Pseudomonas putida* phage, of the *E. coli* phage N4, of the phage LUZ24, gp61 muramidase, STM0016 endolysin and PSP3 endolysin.

Further examples for the endolysin part is selected from the group consisting of phiKZgp144 according to SEQ ID NO:1, ELgp188 according to SEQ ID NO:2, *Salmonella* endolysin according to SEQ ID NO:3, Enterobacteria phage T4 endolysin according to SEQ ID NO:4, *Acinetobacter baumanii* endolysin according to SEQ ID NO:5, *E. coli* Phage K1F endolysin according to SEQ ID NO:18, OBPgpLYS according to SEQ ID NO:34, PSP3 *Salmonella* endolysin (PSP3gp10) according to SEQ ID NO:20, *E. coli* Phage P2 endolysin (P2gp09) according to SEQ ID NO:21, *Salmonella typhimurium* phage muramidase STM0016 according to SEQ ID NO:22, *E. coli* Phage N4 muramidase N4-gp61 according to SEQ ID NO:23 and N4-gp61 trunc. according to SEQ ID NO:24, KZ144 according to SEQ ID NO:25.

In another preferred embodiment of the present invention the endolysins, autolysins and bacteriocins of the fusion protein according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, pegylation, chemical changes of the amino-, SH- or carboxyl-groups. Said endolysins, autolysins and bacteriocins of the fusion protein according to the present invention exhibit the lytic activity of the respective wild-type endolysin, autolysin and bacteriocins. However, said activity can be the same, higher or lower as the activity of the respective wild-type endolysin. Said activity can be about 10, 20, 30, 40, 50, 60, 70, 80, 90, 100, 110, 120, 130, 140, 150, 160, 170, 180, 190 or about 200% of the activity of the respective wild-type endolysin or even more. The activity can be measured by assays well known in the art by a person skilled in the art as e.g. the plate lysis assay or the liquid lysis assay which are e.g. described in (Briers et al., *J. Biochem. Biophys Methods* 70: 531-533, (2007) or Donovan D M, Lardeo M Foster-Frey J. *FEMS Microbiol Lett.* 2006 December; 265(1) or similar publications.

Preferably, the peptide stretch of the fusion protein according to the invention is fused to the N-terminus and/or to the C-terminus of the endolysin, autolysin or bacteriocin. In a particular preferred embodiment said peptide stretch is only fused to the N-terminus of the enzyme. In another preferred embodiment the peptide stretch is only fused to the C-terminus of the enzyme. However, also preferred are modified fusion proteins having a peptide stretch both on the N-terminus and on the C-terminus. Said peptide stretches on the N-terminus and on the C-terminus can be the same or distinct peptide stretches. The peptide stretch can be linked to the enzyme by additional amino acid residues e.g. due to cloning reasons. Preferably said peptide stretch can be linked to the fusion protein by at least 1, 2, 3, 4, 5, 6, 7, 8, 9 or 10 additional amino acid residues. In a preferred embodiment the peptide stretch is linked to the enzyme by the additional amino acid residues glycine and serine (Gly-Ser) or leucine and glutamic acid (Leu-Glu). Moreover, the peptide stretch of the fusion protein according to the invention further comprises additional amino acids on its N-terminus. Preferably the peptide stretch comprises the amino acid methionine (Met), alanine and methionine and glycine (Ala-Met-Gly-Ser) or alanine and methionine and glycine and serine (Ala-Met-Gly-Ser).

The peptide stretch of the fusion protein according to the present invention is preferably covalently bound to the enzyme. Preferably, said peptide stretch consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred is a peptide stretch comprising about 5 to about 100 amino acid residues, about 5 to about 50 or about 5 to about 30 amino acid residues. More preferred is a peptide stretch comprising about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues.

Preferably, the peptide stretch is no tag such as a His-tag, Strep-tag, Avi-tag, Myc-tag, Gst-tag, JS-tag, cystein-tag, FLAG-tag or other tags known in the art and no thioredoxin or maltose binding proteins (MBP). However, the peptide stretch and/or the endolysin, autolysin or bacteriocin according to the present invention may comprise in addition such tag or tags.

More preferably the peptide stretch has the function to lead the fusion protein through the outer membrane but may have activity or may have no or only low activity when administered without being fused to the enzyme. The function to lead the fusion protein through the outer membrane of Gram-negative bacteria is caused by the potential of the outer membrane or LPS disrupting or permeabilising or destabilizing activity of said peptide stretch.

In one aspect of the present invention the fused peptide stretch is an amphipatic peptide, which comprises one or more of the positively charged amino acid residues of lysine, arginine and/or histidine, combined to one or more of the hydrophobic amino acid residues of valine, isoleucine, leucine, methionine, phenylalanine, tryptophan, cysteine, alanine, tyrosine, histidine, threonin, serine, proline and/or glycine. Side chains of the amino acid residues are preferably oriented in order that cationic and hydrophobic surfaces are clustered at opposite sides of the peptide. Preferably, more than about 30, 40, 50, 60 or 70% of the amino acid residues in said peptide are positively charged amino acid. Preferably, more than about 30, 40, 50, 60 or 70%, of the amino acid residues in said peptide are hydrophobic amino acid residues. Advantageously, the amphipathic peptide is fused to the N-terminal and/or the C-terminal end of the enzyme having cell wall degrading activity, thus enhancing the amphipathicity of the latter proteins.

In another embodiment of the invention, the amphipathic peptide fused to the enzyme consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues. In a preferred embodiment at least about 30, 40, 50, 60 or 70% of the said amino acid residues of the amphipatic peptide are either arginine or lysine residues and/or at least about 30, 40, 50, 60 or 70% of the said amino acid residues of the amphipathic peptide are of the hydrophobic amino acids valine, isoleucine, leucine, methionine, phenylalanine, tryptophan, cysteine, alanine, tyrosine, histidine, threonin, serine, proline and/or glycine.

Preferred amphipatic peptides are Pleurocidin according to SEQ ID NO:6, Cecropin P1 according to SEQ ID NO:7, Buforin II according to SEQ ID NO:8, Buforin I according to SEQ ID NO:19 and Magainin according to SEQ ID NO:9. Further preferred amphipatic peptides are Cathelidicine e.g. LL-37 according to SEQ ID NO:10, Nigrocine 2 according to SEQ ID NO:26 and Ascaphine 5 according to SEQ ID NO:27.

In a further aspect of the present invention the fused peptide stretch is an antimicrobial peptide, which comprises a positive net charge and around 50% hydrophobic amino acids. The antimicrobial peptides are amphipathic, with a length of about 12 to about 50 amino acid residues.

Specific examples of antimicrobial peptides according to the present invention are listed in the following table.

TABLE 2

| Peptid | Sequenz | |
|---|---|---|
| LL-37 | LLGDFFRKSKEKIGKEFKRIVQRIKDFLRNLVPRTES | SEQ ID NO: 10 |
| SMAP-29 | RGLRRLGRKIAHGVKKYGPTVLRIIRIAG | SEQ ID NO: 11 |
| Indolicidin | ILPWKWPWWPWRR | SEQ ID NO: 12 |
| Protegrin | RGGRLCYCRRRFCVCVGR | SEQ ID NO: 13 |

TABLE 2-continued

| Peptid | Sequenz | |
|---|---|---|
| Cecropin P1 | SWLSKTAKKLENSAKKRISEGIAIAIQGGPR | SEQ ID NO: 7 |
| Magainin | GIGKFLHSAKKFGKAFVGEIMNS | SEQ ID NO: 9 |
| Pleurocidin | GWGSFFKKAAHVGKHVGKAALTHYL | SEQ ID NO: 6 |
| Cecropin A (A.aegypti) | GGLKKLGKKLEGAGKRVFNAAEKALPVVAGAKALRK | SEQ ID NO: 14 |
| Cecropin A (D. melanogaster) | GWLKKIGKKIERVGQHTRDATIQGLGIPQQAANVAATARG | SEQ ID NO: 15 |
| Buforin II | TRSSRAGLQFPVGRVHRLLRK | SEQ ID NO: 8 |
| Sarcotoxin IA | GWLKKIGKKIERVGQHTRDATIQGLGIAQQAANVAATAR | SEQ ID NO: 16 |
| Apidaecin | ANRPVYIPPPRPPHPRL | SEQ ID NO: 28 |
| Ascaphine 5 | GIKDWIKGAAKKLIKTVASHIANQ | SEQ ID NO: 27 |
| Nigrocine 2 | GLLSKVLGVGKKVLCGVSGLVC | SEQ ID NO: 26 |
| Pseudin 1 | GLNTLKKVFQGLHEAIKLINNHVQ | SEQ ID NO: 29 |
| Ranalexin | FLGGLIVPAMICAVTKKC | SEQ ID NO: 30 |
| Melittin | GIGAVLKVLTTGLPALISWIKRKRQQ | SEQ ID NO: 31 |

In a further aspect of the present invention the fused peptide stretch is a sushi peptide which is described by Ding J L, Li P, Ho B Cell Mol Life Sci. 2008 April; 65(7-8): 1202-19. The Sushi peptides: structural characterization and mode of action against Gram-negative bacteria. Especially preferred is the sushi 1 peptide according to SEQ ID NO:32.

Preferred sushi peptides are sushi peptides S1 and S3 and multiples thereof; FASEB J. 2000 September; 14(12):1801-13.

In a further aspect of the present invention the fused peptide stretch is a defensin, preferably Cathelicidine, Cecropin P1, Cecropin A or Magainin II.

In a further aspect of the present invention the fused peptide stretch is a hydrophobic peptide e.g. Apidaecine having the amino acid sequence according to SEQ ID NO:28, WLBU2-Variant having the amino acid sequence according to SEQ ID NO:33 and Walmagh1 having the amino acid sequence according to SEQ ID NO:35. The hydrophobic peptide having the amino acid sequence Phe-Phe-Val-Ala-Pro (SEQ ID NO:17) is not part of the present invention.

In another preferred embodiment of the present invention the peptide stretches of the fusion protein according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, peglyation, chemical changes of the amino-, SH- or carboxyl-groups.

Specific examples of fusion proteins according to the present invention are listed in the following table:

TABLE 3

| Fusion protein | Fusion protein | Enzyme part | Peptide stretch (N-terminal unless otherwise indicated) |
|---|---|---|---|
| P1-E6 | SEQ ID NO: 36 | KZ144 (SEQ ID NO: 25) | Ascaphine 5 (SEQ ID NO: 27) |
| P2-E6 | SEQ ID NO: 37 | KZ144 (SEQ ID NO: 25) | Apiadaecine (SEQ ID NO: 28) |
| P3-E6 | SEQ ID NO: 38 | KZ144 (SEQ ID NO: 25) | Nigrocine 2 (SEQ ID NO: 26) |
| P4-E6 | SEQ ID NO: 39 | KZ144 (SEQ ID NO: 25) | Pseudin 1 (SEQ ID NO: 29) |
| P7-E6 | SEQ ID NO: 40 | KZ144 (SEQ ID NO: 25) | Ranalexin (SEQ ID NO: 30) |
| P8-E6 | SEQ ID NO: 41 | KZ144 (SEQ ID NO: 25) | WLBU2-Variant (SEQ ID NO: 33) |
| P9-E6 | SEQ ID NO: 42 | KZ144 (SEQ ID NO: 25) | Sushi 1 (SEQ ID NO: 32) |
| P10-E6 | SEQ ID NO: 43 | KZ144 (SEQ ID NO: 25) | Melittin (SEQ ID NO: 31) |
| P11-E6 | SEQ ID NO: 44 | KZ144 (SEQ ID NO: 25) | LL-37 (SEQ ID NO: 10) |
| P12-E6 | SEQ ID NO: 45 | KZ144 (SEQ ID NO: 25) | Indolicidin (SEQ ID NO: 12) |
| P13-E6 | SEQ ID NO: 46 | KZ144 (SEQ ID NO: 25) | SMAP-29 (SEQ ID NO: 11) |
| P14-E6 | SEQ ID NO: 47 | KZ144 (SEQ ID NO: 25) | Protegrin (SEQ ID NO: 13) |
| P15-E6 | SEQ ID NO: 48 | KZ144 (SEQ ID NO: 25) | Cecropin P1 (SEQ ID NO: 7) |
| P16-E6 | SEQ ID NO: 49 | KZ144 (SEQ ID NO: 25) | Magainin (SEQ ID NO: 9) |
| P17-E6 | SEQ ID NO: 50 | KZ144 (SEQ ID NO: 25) | Pleurocidin (SEQ ID NO: 6) |
| P18-E6 | SEQ ID NO: 51 | KZ144 (SEQ ID NO: 25) | Cecropin A (A. aegypti) (SEQ ID NO: 14) |
| P19-E6 | SEQ ID NO: 52 | KZ144 (SEQ ID NO: 25) | Cecropin A (A. melanogaster) (SEQ ID NO: 15) |
| P20-E6 | SEQ ID NO: 53 | KZ144 (SEQ ID NO: 25) | Buforin II (SEQ ID NO: 8) |
| P21-E6 | SEQ ID NO: 54 | KZ144 (SEQ ID NO: 25) | Sarcotoxin IA (SEQ ID NO: 16) |
| P1-E3 | SEQ ID NO: 55 | STM0016 (SEQ ID NO: 22) | Ascaphine 5 (SEQ ID NO: 27) |

TABLE 3-continued

| Fusion protein | Fusion protein | Enzyme part | Peptide stretch (N-terminal unless otherwise indicated) |
|---|---|---|---|
| | SEQ ID NO: 56 | STM0016 (SEQ ID NO: 22) | Nigrocine 2 (SEQ ID NO: 26) |
| | SEQ ID NO: 57 | STM0016 (SEQ ID NO: 22) | SMAP-29 (SEQ ID NO: 11) |
| | SEQ ID NO: 58 | STM0016 (SEQ ID NO: 22) | Sarcotoxin IA (SEQ ID NO: 16) |
| P10-E4 | SEQ ID NO: 59 | N4-gp61 (SEQ ID NO: 23) | Melittin (SEQ ID NO: 31) |
| | SEQ ID NO: 60 | N4-gp61 (SEQ ID NO: 23) | SMAP-29 (SEQ ID NO: 11) |
| P10-E5 | SEQ ID NO: 61 | N4-gp61 trunc. (SEQ ID NO: 24) | Melittin (SEQ ID NO: 31) |
| | SEQ ID NO: 62 | N4-gp61 trunc. (SEQ ID NO: 24) | Cecropin P1 (SEQ ID NO: 7) |
| | SEQ ID NO: 63 | N4-gp61 trunc. (SEQ ID NO: 24) | SMAP-29 (SEQ ID NO: 11) |

The fusion protein according to the present invention, and thus in particular the especially preferred fusion proteins according to SEQ ID NO: 36 to 63, may additional comprise a methionine on the N-terminus.

The fusion protein according to the present invention, and thus in particular the especially preferred fusion proteins according to SEQ ID NO: 36 to 63 may additional comprise a tag e.g. for purification. Preferred is a His6-tag, preferably at the C-terminus and/or the N-terminus of the fusion protein. Said tag can be linked to the fusion protein by additional amino acid residues e.g. due to cloning reasons. Preferably said tag can be linked to the fusion protein by at least 1, 2, 3, 4, 5, 6, 7, 8, 9 or 10 additional amino acid residues. In a preferred embodiment the fusion protein comprises a His6-tag at its C-terminus linked to the fusion protein by the additional amino acid residues lysine and glycine (Lys-Gly) or leucine and glutamic acid (Leu-Glu). In another preferred embodiment the fusion protein comprises a His6-tag at its N-terminus linked to the fusion protein by the additional amino acid residues lysine and glycine (Lys-Gly) or leucine and glutamic acid (Leu-Glu). In another preferred embodiment the fusion protein comprises a His6-tag at its N- and C-terminus linked to the fusion protein by the additional amino acid residues lysine and glycine (Lys-Gly) or leucine and glutamic acid (Leu-Glu).

In a more preferred embodiment the fusion protein comprises a His6-tag at its C-terminus linked to the fusion protein by the additional amino acid residues leucine and glutamic acid (Leu-Glu) and the peptide stretch of the fusion protein according to the invention is linked to the N-terminus of the enzyme by the additional amino acid residues glycine and serine. In another preferred embodiment the fusion protein comprises a His6-tag at its C-terminus linked to the fusion protein by the additional amino acid residues leucine and glutamic acid (Leu-Glu) and the peptide stretch of the fusion protein according to the invention is linked to the N-terminus of the enzyme by the additional amino acid residues glycine and serine (Gly-Ser) and the fusion protein comprises on the N-terminus the additional amino acid residues methionine (Met) or alanine, methionine and glycine (Ala-Met-Gly) or alanine, methionine, glycine and serine (Ala-Met-Gly-Ser). Preferably the fusion proteins are according to SEQ ID NO: 77 to 90.

Fusion proteins are constructed by linking at least two nucleic acid sequences using standard cloning techniques as described e.g. by Sambrook et al. 2001, Molecular Cloning: A Laboratory Manual. Such a protein may be produced, e.g., in recombinant DNA expression systems. Such fusion proteins according to the present invention can be obtained by fusing the nucleic acids for endolysin and the respective peptide stretch.

The fusion proteins according to the present invention may be fused or linked to other additional proteins. Example for this other additional protein is thioredoxin.

The present invention further relates to an isolated nucleic acid molecule encoding the fusion protein according to the present invention. The present invention further relates to a vector comprising the nucleic acid molecule according to the present invention. Said vector may provide for the constitutive or inducible expression of said fusion protein according to the present invention.

The invention also relates to a method for obtaining said fusion proteins from a micro-organism, such as a genetically modified suitable host cell which expresses said fusion proteins. Said host cell may be a micro-organism such as bacteria or yeast or an animal cell as e.g. a mammalian cell, in particular a human cell. In one embodiment of the present invention the host cell is a *Pichia pastoris* cell. The host may be selected due to mere biotechnological reasons, e.g. yield, solubility, costs, etc. but may be also selected from a medical point of view, e.g. a non-pathological bacteria or yeast, human cells.

Another aspect of the present invention is related to a method for genetically transforming a suitable host cell in order to obtain the expression of the fusion proteins according to the invention wherein the host cell is genetically modified by the introduction of a genetic material encoding said fusion proteins into the host cell and obtain their translation and expression by genetic engineering methods well known by the man skilled in the art.

In a further aspect the present invention relates to a composition, preferably a pharmaceutical composition, comprising a fusion protein according to the present invention and/or a host transformed with a nucleic acid molecule or a vector comprising a nucleotide sequence encoding a fusion protein according to the present invention.

In a preferred embodiment of the present invention the composition comprises additionally agents permeabilizing the outer membrane of Gram-negative bacteria such metal chelators as e.g. EDTA, TRIS, lactic acid, lactoferrin, polymyxin, citric acid and/or other substances as described e.g. by Vaara (Agents that increase the permeability of the outer membrane. Vaara M. Microbiol. Rev. 1992 September; 56 (3):395-441). Also preferred are compositions comprising combinations of the above mentioned permeabilizing agents. Especially preferred is a composition comprising about 10 μM to about 100 mM EDTA, more preferably about 50 μM to about 10 mM EDTA, more preferably about 0.5 mM to about 10 mM EDTA, more preferably about 0.5 mM to about 2 mM EDTA, more preferably about 0.5 mM to 1 mM EDTA. However, also compositions comprising about 10 μM to about 0.5 mM EDTA are preferred. Also preferred is a composition comprising about 0.5 mM to about 2 mM EDTA, more preferably about 1 mM EDTA and additionally about 10 to about 100 mM TRIS.

The present invention also relates to a fusion protein according to the present invention and/or a host transformed with a nucleic acid comprising a nucleotide sequence encoding a fusion protein according to the present invention for use as a medicament. In a further aspect the present invention relates to the use of a fusion protein according to the present invention and/or a host transformed with a vector comprising a nucleic acid molecule comprising a nucleotide sequence encoding a modified, fusion protein according to the present invention in the manufacture of a medicament for the treatment and/or prevention of a disorder, disease or condition associated with Gram-negative bacteria. In particular the treatment and/or prevention of the disorder, disease or condition may be caused by Gram-negative bacteria of bacterial groups, families, genera or species comprising strains pathogenic for humans or animals like Enterobacteriaceae (*Escherichia*, especially *E. coli*, *Salmonella, Shigella, Citrobacter, Edwardsiella, Enterobacter, Hafnia, Klebsiella*, especially *K. pneumoniae, Morganella, Proteus, Providencia, Serratia, Yersinia*), Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella*, Spirochaetaceae (*Treponema* and *Borrelia*), Leptospiraceae, *Campylobacter, Helicobacter, Spirillum, Streptobacillus*, Bacteroidaceae (*Bacteroides, Fusobacterium, Prevotella, Porphyromonas*), *Acinetobacter*, especially *A. baumanii*.

The present invention further relates to a medicament comprising a fusion protein according to the present invention and/or a host transformed with a nucleic acid comprising a nucleotide sequence encoding a fusion protein according to the present invention.

In a further aspect the present invention relates to a method of treating a disorder, disease or condition in a subject in need of treatment and/or prevention, which method comprises administering to said subject an effective amount of a fusion protein according to the present invention and/or an effective amount of a host transformed with a nucleic acid comprising a nucleotide sequence encoding a fusion protein according to the present invention or a composition according to the present invention. The subject may be a human or an animal.

In particular said method of treatment may be for the treatment and/or prevention of infections of the skin, of soft tissues, the respiratory system, the lung, the digestive tract, the eye, the ear, the teeth, the nasopharynx, the mouth, the bones, the vagina, of wounds of bacteraemia and/or endocarditis caused by Gram-negative bacteria, in particular by the Gram-negative bacteria as listed above.

The dosage and route of administration used in a method of treatment (or prophylaxis) according to the present invention depends on the specific disease/site of infection to be treated. The route of administration may be for example oral, topical, nasopharyngeal, parenteral, intravenous, rectal or any other route of administration.

For application of a fusion protein according to the present invention and/or an effective amount of a host transformed with a nucleic acid comprising a nucleotide sequence encoding a fusion protein according to the present invention or a composition according to the present invention to a site of infection (or site endangered to be infected) a formulation may be used that protects the active compounds from environmental influences such as proteases, oxidation, immune response etc., until it reaches the site of infection. Therefore, the formulation may be capsule, dragee, pill, powder, suppository, emulsion, suspension, gel, lotion, cream, salve, injectable solution, syrup, spray, inhalant or any other medical reasonable galenic formulation. Preferably, the galenic formulation may comprise suitable carriers, stabilizers, flavourings, buffers or other suitable reagents. For example, for topical application the formulation may be a lotion, cream, gel, salve or plaster, for nasopharyngeal application the formulation may be saline solution to be applied via a spray to the nose. For oral administration in case of the treatment and/or prevention of a specific infection site e.g. in the intestine, it can be necessary to protect a fusion protein according to the present invention from the harsh digestive environment of the gastrointestinal tract until the site of infection is reached. Thus, bacteria as carrier, which survive the initial steps of digestion in the stomach and which secret later on a fusion protein according to the present invention into the intestinal environment can be used.

In a specific embodiment of the present invention the use of a fusion protein according to the present invention and/or a host transformed with a vector comprising a nucleic acid molecule comprising a nucleotide sequence encoding a fusion protein according to the present invention in the manufacture of a medicament for the treatment and/or prevention of a disorder, disease or condition caused by *Pseudomonas*, particularly by *Pseudomonas aeruginosa* in particular intestinal affections, in particular in infants, infections of the meninges, e.g. meningitis haemorrhagica, infections of the middle ear, the skin (*Ecthyma gangraenosum*), in particular burns, the urinary tract, rhinitis, bacteremic pneumonia, in particular wherein the patient is suffering from cystic fibrosis or hematologic malignancies such as leukemia, or with neutropenia from immunosuppressive therapy, septicemia, in particular because of long-term intravenous or urinary catheterization, invasive surgical procedures and severe burns, endocarditis, in particular wherein the patient is a intravenous drug user or a patient with complications from open heart surgery, highly destructive ocular infections, in particular after the use of contaminated ophthalmologic solutions or severe facial burns, osteochondritis, in particular as a result of severe trauma or puncture wounds through contaminated clothing.

In another specific embodiment of the present invention the disorder, disease or condition is caused by *Burkholderia pseudomallei*, in particular Whitmore's Disease, chronic pneumonia, septicemia, in particular wherein the patient has a traumatized skin lesion.

In another specific embodiment of the present invention the disorder, disease or condition is caused by *Salmonella thyphimurium* and *Salmonella enteritidis*, in particular acute gastroenteritis and local purulent processes, particularly osteomyelitis, endocarditis, cholecystitis and especially caused by *Salmonella thyphimurium* meningitis, in particular wherein the patient is less than two years old.

In another specific embodiment of the present invention the disorder, disease or condition is caused by *Salmonella typhi*, in particular typus.

In another specific embodiment of the present invention the disorder, disease or condition is caused by *Salmonell paratyphi*, in particular paratyphus.

In another specific embodiment of the present invention the disorder, disease or condition is caused by *Acinetobacter baumannii*, in particular bronchitis, pneumonia, wound infections and septicemia, in particular as a result of intravenous catheterization.

In another specific embodiment of the present invention the disorder, disease or condition is caused by *Escherichia coli*, in particular extra intestinal infections, particularly appendicitis, purulent cholecystitis, peritonitis, purulent meningitis and infection of the urinary tract, intraintestinal *E. coli* infections, particularly epidemic enteritis, and infectious disease similar to dysentery, septicemia, enterotoxemia, mastitis and dysentery.

In another specific embodiment of the present invention the disorder, disease or condition is caused by *Klebsiella*

*pneumoniae*, in particular pneumonia, bacteremia, meningitis and infections of the urinary tract.

Preferably, a fusion protein according to the present invention is used for medical treatment, if the infection to be treated (or prevented) is caused by multiresistant bacterial strains, in particular by strains resistant against one or more of the following antibiotics: streptomycin, tetracycline, cephalothin, gentamicin, cefotaxime, cephalosporin, ceftazidime or imipenem. Furthermore, a fusion protein according to the present invention can be used in methods of treatment by administering it in combination with conventional antibacterial agents, such as antibiotics, lantibiotics, bacteriocins or endolysins, etc.

The present invention also relates to a pharmaceutical pack comprising one or more compartments, wherein at least one compartment comprises one or more fusion protein according to the present invention and/or one or more hosts transformed with a nucleic acid comprising a nucleotide sequence encoding a fusion protein according to the present invention or a composition according to the present invention, In another aspect the present invention relates to a process of preparation of a pharmaceutical composition, said process comprising admixing one or more fusion protein according to the present invention and/or one or more hosts transformed with a nucleic acid comprising a nucleotide sequence encoding a fusion protein according to the present invention with a pharmaceutically acceptable diluent, excipient or carrier.

In an even further aspect the composition according to the present invention is a cosmetic composition. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the fusion protein according to the present invention in order to degrade already existing or freshly settling pathogenic Gram-negative bacteria.

In a further aspect the present invention relates to the fusion protein according to the present invention for use as diagnostic means in medicinal, food or feed or environmental diagnostics, in particular as a diagnostic means for the diagnostic of bacteria infection caused in particular by Gram-negative bacteria. In this respect the fusion protein according to the present invention may be used as a tool to specifically degrade pathogenic bacteria, in particular Gram-negative pathogenic bacteria. The degradation of the bacterial cells by the fusion protein according to the present invention can be supported by the addition of detergents like Triton X-100 or other additives which weaken the bacterial cell envelope like polymyxin B. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. β-galactosidase for enterobacteria, coagulase for coagulase positive strains).

In a further aspect the present invention relates to the use of the fusion protein according to the present invention for the treatment, removal, reduction or prevention of Gram-negative bacterial contamination of foodstuff, of food processing equipment, of food processing plants, of surfaces coming into contact with foodstuff such as shelves and food deposit areas and in all other situations, where pathogenic, facultative pathogenic or other undesirable bacteria can potentially infest food material, of medical devices and of all kind of surfaces in hospitals and surgeries.

In particular, a fusion protein of the present invention may be used prophylactically as sanitizing agent. Said sanitizing agent may be used before or after surgery, or for example during hemodialysis. Moreover, premature infants and immunocompromised persons, or those subjects with need for prosthetic devices may be treated with a fusion protein according to the present invention. Said treatment may be either prophylactically or during acute infection. In the same context, nosocomial infections, especially by antibiotic resistant strains like *Pseudomonas aeruginosa* (FQRP), *Acinetobacter* species and Enterobacteriaceae such as *E. coli*, *Salmonella*, *Shigella*, *Citrobacter*, *Edwardsiella*, *Enterobacter*, *Hafnia*, *Klebsiella*, *Morganella*, *Proteus*, *Providencia*, *Serratia* and *Yersinia* species may be treated prophylactically or during acute phase with a fusion protein of the present invention. Therefore, a fusion protein according to the present invention may be used as a disinfectant also in combination with other ingredients useful in a disinfecting solution like detergents, tensids, solvents, antibiotics, lanthibiotics, or bacteriocins.

For the use of the fusion protein according to the present invention as a disinfectant e.g. in hospital, dental surgery, veterinary, kitchen or bathroom, the fusion protein can be prepared in a composition in form of e.g. a fluid, a powder, a gel, or an ingredient of a wet wipe or a disinfection sheet product. Said composition may additionally comprise suitable carrier, additives, diluting agents and/or excipients for its respective use and form, respectively, —but also agents that support the antimicrobial activity like EDTA or agents enhance the antimicrobial activity of the fusion proteins. The fusion protein may also be used with common disinfectant agents like, Alcohols, Aldehydes, Oxidizing agents, Phenolics, Quaternary ammonium compounds or UV-light. For disinfecting for example surfaces, objects and/or devices the fusion protein can be applied on said surfaces, objects and/or devices. The application may occur for instance by wetting the disinfecting composition with any means such as a cloth or rag, by spraying, pouring. The fusion proteins may be used in varying concentration depending on the respective application and the "reaction time" intended to obtain full antimicrobial activity.

Another aspect of the present invention is that the invention can be used like a tool box, i.e. any peptide stretch disclosed above may be fused to any endolysin, autolysin or bacteriocin disclosed herein. Thus, it is possible to combine the respective peptide stretch, which enables the binding of the fusion protein to the respective bacteria and the endolysin, autolysin or bacteriocin, which inhibit the growth of the respective bacteria. Consequently, it is possible to construct a suitable fusion protein for any bacteria which should be eliminated.

Further scope of applicability of the present invention will become apparent from the detailed description given hereinafter, however, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

The following examples explain the present invention but are not considered to be limiting. Unless indicated differently, molecular biological standard methods were used, as e.g., described by Sambrock et al., 1989, Molecular Cloning: A Laboratory Manual, 2nd edition, Cold Spring Harbor Laboratory Press, Cold Spring Harbor, N.Y.

EXAMPLE 1. CLONING, EXPRESSION AND PURIFICATION OF GP144 AND GP188 MODIFIED WITH AN AMPHIPATHIC PEPTIDE

As a proof of principle, the potential of the LPS disrupting activity of amphipathic peptides to lead gp144 and gp188 through the outer membrane and the consequent antibacterial activity against Gram-negative bacteria is demonstrated. Gp144 and gp188 are modular endolysins originating from *Pseudomonas aeruginosa* phages φKZ and EL with an N-terminal peptidoglycan binding and C-terminal catalytic domain (Briers et al., 2007).

To extend the 5' end of the open reading frame encoding gp144 or gp188 with a gene fragment encoding the amphipathic α4 helix of T4 lysozyme (aa 143-155: Pro-Asn-Arg-Ala-Lys-Arg-Val-Ile-Thr-Thr-Phe-Arg-Thr according to SEQ ID NO: 92) a tail PCR with an extended 5' primer and standard 3' primer was applied. The PCR product was cloned in the pEXP5CT/TOPO® expression vector (Invitrogen, Carlsbad, Calif., USA).

Expression of all constructs was performed in *E. coli* BL21 (DE3) pLysS cells. All proteins were purified by $Ni^{2+}$ affinity chromatography using the C-terminal 6xHis-tag. The yields for different purifications are shown in table 4. Remarkably, α4-KZ144 production was not toxic for the host, in contrast to KZ144, resulting in a significant higher yield.

Purified stock solutions were ~90% pure. All gp144 derivatives showed multimer formation which could be converted to monomers by addition of β-mercapto-ethanol, indicating that interdisulfide bonds cause multimerization.

TABLE 4

Yields of recombinant purification of endolysins modified with an amphipathic peptide*.

| Fusion | Endolysin | |
|---|---|---|
| | gp144 | gp188 |
| α4 helix | 179 mg | 38 mg |

*The total yield of purified recombinant protein per liter E. colt expression culture is shown. This value was determined by spectrophotometric measurement of the protein concentration and the total volume of the purified stock solution. The purification of gp188 derivatives was performed under more stringent conditions (65 mM imidazole) compared to gp144 derivatives (50 mM imidazole) to ensure high purity.

Characterization of Gp144 and Gp188 Modified with an Amphipathic Peptide

1.A. Enzymatic Activity of Gp144 and Gp188 Modified with an Amphipathic Peptide

To assess the influence of the modification on the enzymatic activity of gp144 or gp188, the specific activity of the variants was measured on chloroform-permeabilized *Pseudomonas aeruginosa* cells and compared to the corresponding unmodified endolysin. Different incremental amounts of all modified endolysins were tested to determine the corresponding saturation curve.

The slope of the linear regression of the linear region of this curve is a measure for the specific activity and was expressed relatively to the slope of unmodified gp144 or gp188 (Table 5).

TABLE 5

Enzymatic activity of gp144 or gp188 modified with an amphipathic peptide*.

| Fusion | Endolysin | |
|---|---|---|
| | gp144 | gp188 |
| α4 helix | 23% | 146% |

*The specific enzymatic activity of the different variants was determined and expressed relatively to the specific activity of the corresponding original endolysin (=100%), which was tested simultaneously. The buffer conditions of the assay were the optimal conditions of the corresponding endolysins ($KH_2PO_4/K_2HPO_4$ I = 120 mM pH 6.2 and I = 80 mM pH 7.3 for gp144 and gp188, respectively).

1.B. Antibacterial Activity of Gp144 and Gp188 Modified with an Amphipathic Peptide Exponential (~$10^6$/ml) *P. aeruginosa* PAO1 cells were incubated at room temperature with unmodified and modified gp144/gp188. After 1 hour, cell suspensions were diluted and plated. The residual colonies were counted after an overnight incubation (Table 6). Unmodified gp144 gp188 does not reduce cell numbers significantly compared to the negative control. This observation illustrates the efficacy of the outer membrane as a barrier. Fusion proteins with the amphipathic α4-helix inactivate exponential cells with 50±11 and 34±11% for α4-KZ144 and α4-EL188, respectively. When stationary cells with a 100-fold higher density are used, these values are similar (35±18 and 32±17%, respectively). Despite the rather high variability between different replicates, these values differ significantly from the untreated cells (α=0.05). In general, modified gp144 derivatives tend to have a higher antibacterial activity than gp188 derivatives.

TABLE 6

Antibacterial effect of endolysins gp144 and gp188 and their derivatives*.

| Exponentially growing cells | Endolysins | | | |
|---|---|---|---|---|
| | gp144 | | gp188 | |
| Fusion | % | log | % | log |
| unmodified | 0 ± 15 | 0.00 ± 0.06 | 10 ± 13 | 0.05 ± 0.06 |
| α4 helix | 50 ± 11 | 0.31 ± 0.09 | 34 ± 11 | 0.19 ± 0.07 |

*Exponentially growing *P. aeruginosa* PAO1 cells were 100 x diluted and incubated (final density was ~$10^6$/ml) with 10 μg undialyzed protein (final concentration 100 μg/ml, buffer: 20 mM $NaH_2PO_4$—NaOH pH 7.4; 0.5M NaCl; 0.5M imidazole) for 1 hour at room temperature. Aliquots are diluted and plated. The antibacterial activity is expressed as the relative inactivation (%) (=100 − ($N_i$/$N_0$)*100 with $N_0$ = number of untreated cells and $N_i$ = number of treated cells) and in logarithmic units (=$\log_{10}N_0/N_i$). All samples were replicated in six fold. Averages/standard deviations are represented. Statistical analysis was performed using a student's t-test.

EXAMPLE 2. CLONING, EXPRESSION AND PURIFICATION OF GP144 AND GP188 MODIFIED WITH A HYDROPHOBIC PEPTIDE

As a proof of principle, the potential of the LPS disrupting activity of a hydrophobic pentapeptides to lead gp144 and gp188 through the outer membrane and the consequent antibacterial activity against Gram-negative bacteria is demonstrated. Gp144 and gp188 are modular endolysins originating from *Pseudomonas aeruginosa* phages φKZ and EL with an N-terminal peptidoglycan binding and C-terminal catalytic domain (Briers et al., 2007).

To extend the 5' end of the open reading frame encoding gp144 or gp188 with a gene fragment encoding 5 hydrophobic residues (Phe-Phe-Val-Ala-Pro) a tail PCR with an extended 5' primer and standard 3' primer was applied. The PCR product was cloned in the pEXP5CT/TOPO® expression vector (Invitrogen, Carlsbad, Calif., USA).

Expression of all constructs was performed in *E. coli* BL21 (DE3) pLysS cells. All proteins were purified by Ni2+ affinity chromatography using the C-terminal 6×His-tag. The yields for different purifications are shown in table 7.

Purified stock solutions were ~90% pure. All gp144 derivatives showed multimer formation which could be converted to monomers by addition of β-mercapto-ethanol, indicating that interdisulfide bonds cause multimerization.

TABLE 7

Yields of recombinant purification of endolysin derivatives*.

| Fusion | Endolysin | |
|---|---|---|
| | gp144 | gp188 |
| Phe-Phe-Val-Ala-Pro | 25 mg | 85 mg |

*The total yield of purified recombinant protein per liter E. colt expression culture is shown. This value was determined by spectrophotometric measurement of the protein concentration and the total volume of the purified stock solution. The purification of gp188 derivatives was performed under more stringent conditions (65 mM imidazole) compared to gp144 derivatives (50 mM imidazole) to ensure high purity.

Characterization of Gp144 and Gp188 Modified with a Hydrophobic Pentapeptide

2.A. Enzymatic Activity of Gp144 and Gp188 Modified with a Hydrophobic Pentapeptide To assess the influence of the modifications on the enzymatic activity of gp144 or gp188, the specific activity of the variants was measured on chloroform-permeabilized *Pseudomonas aeruginosa* cells and compared to the corresponding unmodified endolysin. Different incremental amounts of all modified endolysins were tested to determine the corresponding saturation curve. The slope of the linear regression of the linear region of this curve is a measure for the specific activity and was expressed relatively to the slope of unmodified gp144 or gp188 (Table 8).

TABLE 8

Enzymatic activity of gp144 or gp188 modified with a hydrophobic peptide*.

| Fusion | Endolysin | |
|---|---|---|
| | gp144 | gp188 |
| Hydrophobic pentapeptide | 150% | 100% |

*The specific enzymatic activity of the different variants was determined and expressed relatively to the specific activity of the corresponding original endolysin (=100%), which was tested simultaneously. The buffer conditions of the assay were the optimal conditions of the corresponding endolysins (KH$_2$PO$_4$/K$_2$HPO$_4$ I = 120 mM pH 6.2 and I = 80 mM pH 7.3 for gp144 and gp188, respectively).

2.B. Antibacterial Activity of Gp144 and Gp188 Modified with a Hydrophobic Pentapeptide Exponential (~10$^6$/ml) *P. aeruginosa* PAO1 cells were incubated at room temperature with unmodified and modified gp144/gp188. After 1 hour, cell suspensions were diluted and plated. The residual colonies were counted after an overnight incubation (Table 9). Unmodified gp144 gp188 does not reduce cell numbers significantly compared to the negative control. This observation illustrates the efficacy of the outer membrane as a barrier. Incubation with the hydrophobic pentapeptide fusion proteins causes a significant reduction ($\alpha$=0.05) of the bacterial cell number (83±7 and 69±21% for modified gp144 and gp188, respectively). In general, modified gp144 derivatives tend to have a higher antibacterial activity than gp188 derivatives.

TABLE 9

Antibacterial effect of endolysins gp144 and gp188 and their derivatives*.

| Exponentially growing cells | Endolysins | | | |
|---|---|---|---|---|
| | gp144 | | gp188 | |
| Fusion | % | log | % | log |
| unmodified | 0 ± 15 | 0.00 ± 0.06 | 10 ± 13 | 0.05 ± 0.06 |
| Hydrophobic pentapeptide | 83 ± 7 | 0.9 ± 0.2 | 69 ± 21 | 0.7 ± 0.3 |

*Exponentially growing *P. aeruginosa* PAO1 cells were 100 x diluted and incubated (final density was ~10$^8$/ml) with 10 μg undialyzed protein (final concentration 100 μg/ml, buffer: 20 mM NaH$_2$P0$_4$—NaOH pH 7.4; 0.5M NaCl; 0.5M imidazole) for 1 hour at room temperature. Aliquots are diluted and plated. The antibacterial activity is expressed as the relative inactivation (%) (=100 − (N$_i$/No)*100 with N$_0$ = number of untreated cells and N$_i$ = number of treated cells) and in logarithmic units (=log$_{10}$N$_0$/N$_i$). All samples were replicated in six fold. Averages/standard deviations are represented. Statistical analysis was performed using a student's t-test.

EXAMPLE 3: CLONING, EXPRESSION AND PURIFICATION OF KZ144 AND STM0016 MODIFIED WITH VARIOUS PEPTIDE STRETCHES ON THE N-TERMINUS OF THE ENDOLYSIN

KZ144 according to SEQ ID NO: 25 is a modular endolysin originating from *Pseudomonas aeruginosa* phage φKZ with an N-terminal peptidoglycan binding and C-terminal catalytic domain (Briers et al., 2007). The endolysin KZ144 is encoded by the nucleic acid molecule according to SEQ ID NO: 64. The nucleic acid molecule according to SEQ ID NO: 64 was synthetically produced with a BamH I (5"-GGA TCC-3') restriction site at the 5"-end of the nucleic acid molecule and an Xho I (5'-CTC GAG-3') restriction site at the 3'-end of the nucleic acid molecule.

STM0016 is a hypothetical protein with homology to the *E. coli* phage N4 endolysin N4-gp61.

The endolysin STM0016 is encoded by the nucleic acid molecule according to SEQ ID NO: 65. The nucleic acid molecule according to SEQ ID NO: 65 was synthetically produced with a BamH I (5'-GGA TCC-3') restriction site at the 5'-end of the nucleic acid molecule and an Xho I (5"-CTC GAG-3') restriction site at the 3'-end of the nucleic acid molecule.

N4-gp61 is an *E. coli* N4 phage endolysin. The endolysin is encoded by the nucleic acid according to SEQ ID NO: 91. The nucleic acid molecule according to SEQ ID NO: 91 was synthetically produced with a BamH I (5"-GGA TCC-3') restriction site at the 5"-end of the nucleic acid molecule and an Xho I (5'-CTC GAG-3') restriction site at the 3'-end of the nucleic acid molecule.

The following peptide stretches in table 10 were used for production of fusion proteins with the endolysin KZ144 or STM0016:

TABLE 10

| Peptide stretch | Nucleic acid molecule encoding the peptide stretch |
|---|---|
| Pseudin 1 (SEQ ID NO: 29) | SEQ ID NO: 66 |
| Ranalexin (SEQ ID NO: 30) | SEQ ID NO: 67 |
| Sushi 1 (SEQ ID NO: 32) | SEQ ID NO: 68 |
| WLBU2-Variant (SEQ ID NO: 33) | SEQ ID NO: 69 |

TABLE 10-continued

| Peptide stretch | Nucleic acid molecule encoding the peptide stretch |
|---|---|
| Melittin (SEQ ID NO: 31) | SEQ ID NO: 70 |
| SMAP-29 (SEQ ID NO: 11) | SEQ ID NO: 71 |
| Pleurocidin (SEQ ID NO: 6) | SEQ ID NO: 72 |
| Cecropin A (*A. aegypti*) (SEQ ID NO: 14) | SEQ ID NO: 73 |
| Cecropin A (*A. melanogaster*) (SEQ ID NO: 15) | SEQ ID NO: 74 |
| Buforin II (SEQ ID NO: 8) | SEQ ID NO: 75 |
| Sarcotoxin IA (SEQ ID NO: 16) | SEQ ID NO: 76 |

The nucleic acid molecules encoding the respective peptide stretches were synthetically produced with a Nde I (5'-CAT ATG-3') restriction site at the 5'-end of the nucleic acid molecule and a BamH I (5'-GGA TCC-3') restriction site at the 3'-end of the nucleic acid molecule, except the nucleic acid molecule encoding the Sushi 1 peptide, which was produced with a Nco I restriction site plus two additional nucleotides (5'-CCA TGG GC-3') at the 5'-end of the nucleic acid molecule.

Fusion proteins are constructed by linking at least two nucleic acid sequences using standard cloning techniques as described e.g. by Sambrook et al. 2001, Molecular Cloning: A Laboratory Manual. Therefore the nucleic acid molecules encoding the peptide stretches were cleaved in a digest with the respective restriction enzymes Nde I and BamH I and in case of the nucleic acid molecule encoding the peptide stretch Sushi 1 the digest was performed with the restriction enzymes Nco I and BamH I. Subsequently the cleaved nucleic acids encoding the peptide stretches were ligated into the pET21 b expression vector (Novagen, Darmstadt, Germany), which was also cleaved in a digest with the respective restriction enzymes Nde I and BamH I before. The cleaved nucleic acid molecule encoding the peptide stretch Sushi I was ligated into a modified pET32 b expression vector (unmodified vector obtainable from Novagen, Darmstadt, Germany), which was also cleaved in a digest with the respective restriction enzymes Nco I and BamH I before. The modification of the pET32b expression vector refers to the deletion of the sequence encoding a S-tag and the central His-tag.

Afterwards, the nucleic acid molecule encoding the endolysin KZ144 was cleaved in a digest with the restriction enzyme BamH I and Xho I, so that the endolysin could be ligated into the pET21b expression vector (Novagen, Darmstadt, Germany) and the modified pET32 b expression vector, respectively, which were also cleaved in a digest with the respective restriction enzymes BamH I and Xho I before. The nucleic acid molecule encoding the endolysin STM0016 and the nucleic acid molecule encoding the endolysin N4gp61 were cleaved in a digest with the restriction enzyme BamH I and Xho I, so that the respective endolysin could be ligated into the pET21b expression vector (Novagen, Darmstadt, Germany).

Thus, the nucleic acid molecule encoding the peptide stretch is ligated into the respective vector at the 5'-end of the nucleic acid molecule encoding the endolysin KZ144 or STM0016. Moreover, the nucleic acid molecule encoding the endolysin KZ144 or STM0016 is ligated into the respective plasmid, so that a nucleic acid molecule encoding a His-tag consisting of six histidine residues is associated at the 3'-end of the nucleic acid molecule encoding the endolysin.

As some fusion proteins may either be toxic upon expression in bacteria, or not homogenous due to protein degradation, the strategy might be to express these fusion proteins fused or linked to other additional proteins. Example for these other additional protein is thioredoxin, which was shown to mediate expression of toxic antimicrobial peptides in *E. coli* (TrxA mediating fusion expression of antimicrobial peptide CM4 from multiple joined genes in *Escherichia coli*. Zhou L, Zhao Z, Li B, Cai Y, Zhang S. Protein Expr Purif. 2009 April; 64(2):225-230). In the case of the fusion protein consisting of the N-terminal Sushi 1 peptide and the endolysin KZ144, the Sushi 1 peptide is ligated into the modified pET32 b expression vector, so that an additional thioredoxin is associated at the 5'-end of the Sushi 1 peptide. The thioredoxin could be removed from the expressed fusion protein by the use of enterokinase, therefore between the nucleic acid molecule encoding the Sushi peptide and the one encoding the thioredoxin is an enterokinase restriction site introduced.

The sequence of the endolysin-peptide-fusions was controlled via DNA-sequencing and correct clones were transformed into *E. coli* BL21(DE3) (Novagen, Darmstadt, Germany) for protein expression.

Recombinant expression of the fusion proteins according to SEQ ID NO: 77 to 90 is performed in *E. coli* BL21 (DE3) pLysS and *E. coli* BL21 (DE3) cells (Novagen, Darmstadt, Germany). The cells were growing until an optical density of OD600 nm of 0.5-0.8 was reached. Then the expression of the fusion protein was induced with 1 mM IPTG (isopropylthiogalactoside) and the expression was performed at 37° C. for a period of 4 hours.

*E. coli* BL21 cells were harvested by centrifugation for 20 min at 6000 g and disrupted via sonication on ice. Soluble and insoluble fraction of the *E. coli* crude extract were separated by centrifugation (Sorvall, SS34, 30 min, 15 000 rpm). All proteins were purified by $Ni^{2+}$ affinity chromatography (Akta FPLC, GE Healthcare) using the C-terminal 6×His-tag, encoded by the pET21b or pET32b vectors.

As described above, some of the fusion proteins were expressed using a modified pET32b vector (S-tag and central His-tag deleted), which fuses thioredoxin on the N-terminus of the proteins of interest. The vector also contains an enterokinase cleavage site right before the protein of interest. This site allows the proteolytic cleavage between thioredoxin and the protein of interest, which can purified via the remaining C-terminal His-tag. For antimicrobial function of the fusion protein Sushi 1-KZ144 it may be necessary to remove the thioredoxin by proteolytic cleavage. Therefore the fusion protein was cleaved with 2-4 units/mg recombinant enterokinase (Novagen, Darmstadt, Germany) to remove the thioredoxin following the protocol provided by the manufacturer. After enterokinase cleavage the fusion protein was purified via His-tag purification as described below.

The $Ni^{2+}$ affinity chromatography is performed in 4 subsequent steps, all at room temperature:

1. Equilibration of the Histrap FF 5 ml column (GE Healthcare) with up to 10 column volumes of Washing Buffer (20 mM imidazole, 1 M NaCl and 20 mM Hepes on pH 7.4) at a flow rate of 3-5 ml/min.
2. Loading of the total lysate (with wanted fusion protein) on the Histrap FF 5 ml column at a flow rate of 3-5 ml/min.
3. Washing of the column with up to 10 column volumes of Washing Buffer to remove unbound sample followed by a second washing step with 10% Elution buffer (500 mM imidazole, 0.5 M NaCl and 20 mM Hepes on pH 7.4) at a flow rate of 3-5 ml/min.
4. Elution of bounded fusion proteins from the column with a linear gradient of 4 column volumes of Elution Buffer (500 mM imidazole, 0.5 M NaCl and 20 mM Hepes on pH 7.4) to 100% at a flow rate of 3-5 ml/min.

Purified stock solutions of fusion proteins in Elution Buffer (20 mM Hepes pH 7.4; 0.5 M NaCl; 500 mM imidazole) were at least 90% pure as determined visually on SDS-PAGE gels (data not shown).

The other fusion proteins consisting of KZ144 and the respective peptide stretches were constructed as described in example 3.

*E. coli* DSMZ 11753, *Acinetobacter baumannii* DSMZ 30007 and *Pseudomonas aeruginosa* PAO1p cells (Burn wound isolate, Queen Astrid Hospital, Brussels; Pirnay J P et al. (2003), *J Clin Microbiol.*, 41(3):1192-1202) were used as test strains. Overnight cultures were diluted 10-fold in fresh LB medium and grown to $OD_{600}$=0.6. The culture was spun down and diluted 10-fold in dilution buffer (10 mM HEPES, 0.5 mM EDTA; pH 7.4). Bacteria were incubated at room temperature with each 10 µg undialyzed fusion protein at a final concentration of 100 µg/ml in buffer (20 mM $NaH_2PO_4$—NaOH pH 7.4; 0.5 M NaCl; 0.5 M imidazole). After 1 hour cell dilution series were made in PBS and plated on LB. Additionally, a negative control was plated using buffer (20 mM $NaH_2PO_4$—NaOH pH 7.4; 0.5 M NaCl; 0.5 M imidazole). The residual colonies were counted after an overnight incubation at 37° C. Based on the counted cell numbers the antibacterial activity as logarithmic units (=$\log_{10}N_0/N_i$ with $N_0$=number of untreated cells and $N_i$=number of treated cells) was calculated (Table 11). All samples were replicated at least in four fold.

The antimicrobial activity of these fusion proteins is given in the following table.

TABLE 11

Antimicrobial activity of KZ144 modified with various peptide stretches against gram-negative bacteria

| Fusion protein | Enzyme part | Peptide stretch (N-terminal unless otherwise indicated) | Activity against *Pseudomonas aeruginosa* | Activity against *E. coli* DSMZ 11753 | Activity against *Acinetobacter baumannii* DSMZ 30007 |
|---|---|---|---|---|---|
| SEQ ID NO: 77 | KZ144 (SEQ ID NO: 25) | Pseudin 1 (SEQ ID NO: 29) | + | n.d. | n.d. |
| SEQ ID NO: 78 | KZ144 (SEQ ID NO: 25) | Ranalexin (SEQ ID NO: 30) | + | n.d. | n.d. |
| SEQ ID NO: 79 | KZ144 (SEQ ID NO: 25) | Sushi 1 (SEQ ID NO: 32) | + | n.d. | ++ |
| SEQ ID NO: 80 | KZ144 (SEQ ID NO: 25) | WLBU2-Variant (SEQ ID NO: 33) | n.d. | + | n.d. |
| SEQ ID NO: 81 | KZ144 (SEQ ID NO: 25) | Melittin (SEQ ID NO: 31) | + | n.d. | n.d. |
| SEQ ID NO: 82 | KZ144 (SEQ ID NO: 25) | SMAP-29 (SEQ ID NO: 11) | +++ | +++ | n.d. |
| SEQ ID NO: 83 | KZ144 (SEQ ID NO: 25) | Cecropin A (*A. aegypti*) (SEQ ID NO: 14) | ++ | + | ++ |
| SEQ ID NO: 84 | KZ144 (SEQ ID NO: 25) | Pleurocidin (SEQ ID NO: 6) | + | n.d. | n.d. |
| SEQ ID NO: 85 | KZ144 (SEQ ID NO: 25) | Cecropin A (*A. melanogaster*) (SEQ ID NO: 15) | + | n.d. | n.d. |
| SEQ ID NO: 86 | KZ144 (SEQ ID NO: 25) | Buforin II (SEQ ID NO: 8) | + | n.d. | n.d. |
| SEQ ID NO: 87 | KZ144 (SEQ ID NO: 25) | Sarcotoxin IA (SEQ ID NO: 16) | ++ | ++ | ++ |
| SEQ ID NO: 93 | KZ144 (SEQ ID NO: 25) | α4 helix (SEQ ID NO: 92) | ± | n.d. | n.d. |

Abreviations: ± <1 log; +: 1 log; ++: 2-3 log; +++: 4 or more logs; n.d. means that this strain was not tested with the respective fusion protein.

EXAMPLE 4: ANTIMICROBIAL ACTIVITY OF THE ENDOLYSIN KZ144 MODIFIED WITH VARIOUS PEPTIDE STRETCHES ON THE N-TERMINUS

The fusion protein consisting of KZ144 and the peptide stretch α4 helix was constructed as described in example 1.

EXAMPLE 5: ANTIMICROBIAL ACTIVITY OF THE ENDOLYSIN STM0016 MODIFIED WITH VARIOUS PEPTIDE STRETCHES ON THE N-TERMINUS

The fusion proteins consisting of STM0016 and the peptide stretch Sarcotoxin IA or SMAP-29 was constructed as described in example 3.

*E. coli* DSMZ 11753, *Salmonella typhimujrium* DSMZ 17058 and *Pseudomonas aeruginosa* PAO1p cells (Burn wound isolate, Queen Astrid Hospital, Brussels; Pirnay J P et al. (2003), J Clin Microbiol., 41(3):1192-1202) were used as test strains. The antimicrobial activity of the fusion proteins consisting of the endolysin STM0016 and the peptide Sarcotoxin IA or SMAP-29 was examined as described in example 4. The antimicrobial activity of these fusion proteins is given in the following table.

TABLE 12

| Fusion protein | Enzyme part | Peptide stretch (N-terminal unless otherwise indicated) | Activity against Pseudomonas aeruginosa | Activity against E. coli DSMZ 11753 | Activity against Salmonella typhimurium DSMZ 17058 |
| --- | --- | --- | --- | --- | --- |
| SEQ ID NO: 88 | STM0016 (SEQ ID NO: 22) | Sarcotoxin IA (SEQ ID NO: 16) | + | n.d. | + |
| SEQ ID NO: 89 | STM0016 (SEQ ID NO: 22) | SMAP-29 (SEQ ID NO: 11) | + | + | + |

Abreviations: +: 1 log; n.d. means that this strain was not tested with the respective fusion protein.

EXAMPLE 6: ANTIMICROBIAL ACTIVITY OF THE ENDOLYSIN N4GP61 MODIFIED WITH A PEPTIDE STRETCH ON THE N-TERMINUS

The fusion protein consisting of N4gp61 and the peptide stretch SMAP-29 was constructed as described in example 3.

E. coli DSMZ 11753, Salmonella typhimujrium DSMZ 17058 and Pseudomonas aeruginosa PAO1p cells (Burn wound isolate, Queen Astrid Hospital, Brussels; Pirnay J P et al. (2003), J Clin Microbiol., 41(3):1192-1202) were used as test strains. The antimicrobial activity of the fusion protein consisting of the endolysin N4gp61 and the peptide SMAP-29 was examined as described in example 4. The antimicrobial activity of this fusion protein is given in the following table.

TABLE 13

| Fusion protein | Enzyme part | Peptide stretch (N-terminal unless otherwise indicated) | Activity against Pseudomonas aeruginosa | Activity against E. coli DSMZ 11753 | Activity against Salmonella typhimurium DSMZ 17058 |
| --- | --- | --- | --- | --- | --- |
| SEQ ID NO: 90 | N4-gp61 (SEQ ID NO: 23) | SMAP-29 (SEQ ID NO: 11) | + | + | + |

Abreviations: +: 1 log; n.d. means that this strain was not tested with the respective fusion protein.

EXAMPLE 7: ANTIMICROBIAL ACTIVITY OF THE ENDOLYSIN GP188 MODIFIED WITH A PEPTIDE STRETCH ON THE N-TERMINUS

The fusion proteins consisting of the endolysin gp188 and the peptide stretches α4 helix, SMAP-29 or Sarcotoxin IA were constructed as described in example 1. E. coli DSMZ 11753, Acinetobacter baumannii DSMZ 30007 and Pseudomonas aeruginosa PAO1p cells (Burn wound isolate, Queen Astrid Hospital, Brussels; Pirnay J P et al. (2003), J Clin Microbiol., 41(3):1192-1202) were used as test strains. The antimicrobial activity of the fusion proteins consisting of the endolysin gp188 and the respective peptide stretches was examined as described in example 4. The antimicrobial activity of these fusion proteins is given in the following table.

TABLE 14

| Fusion protein | Enzyme part | Peptide stretch (N-terminal unless otherwise indicated) | Activity against Pseudomonas aeruginosa | Activity against E. coli DSMZ 11753 | Activity against Acinetobacter baumannii DSMZ 30007 |
| --- | --- | --- | --- | --- | --- |
| SEQ ID NO: 94 | gp188 (SEQ ID NO: 2) | α4 helix (SEQ ID NO: 92) | ± | n.d. | n.d. |
| SEQ ID NO: 95 | gp188 (SEQ ID NO: 2) | SMAP-29 (SEQ ID NO: 11) | ++ | ++ | ++ |

TABLE 14-continued

| Fusion protein | Enzyme part | Peptide stretch (N-terminal unless otherwise indicated) | Activity against *Pseudomonas aeruginosa* | Activity against *E. coli* DSMZ 11753 | Activity against *Acinetobacter baumannii* DSMZ 30007 |
| --- | --- | --- | --- | --- | --- |
| SEQ ID NO: 96 | gp188 (SEQ ID NO: 2) | Sarcotoxin IA (SEQ ID NO: 16) | + | + | + |

Abreviations: ± <1 log; +: 1 log; ++: 2-3 log; n.d. means that this strain was not tested with the respective fusion protein.

EXAMPLE 8: ANTIMICROBIAL ACTIVITY OF THE *SALMONELLA* ENDOLYSIN MODIFIED WITH THE PEPTIDE STRETCH SMAP-29 ON THE N-TERMINUS

The fusion proteins consisting of the *Salmonella* endolysin having an amino acid sequence according to SEQ ID NO: 3 and the peptide stretch SMAP-29 were constructed analogous to example 3. *E. coli* DSMZ 11753 and *Salmonella typhimurium* DSMZ 17058 were used as test strains. The antimicrobial activity of the fusion protein was examined as described in example 4. The antimicrobial activity of this fusion protein is given in the following table.

TABLE 15

| Fusion protein | Enzyme part | Peptide stretch (N-terminal unless otherwise indicated) | Activity against *E. coli* DSMZ 11753 | Activity against *Salmonella typhimurium* DSMZ 17058 |
| --- | --- | --- | --- | --- |
| SEQ ID NO: 97 | *Salmonella* endolysin (SEQ ID NO: 3) | SMAP-29 (SEQ ID NO: 11) | + | + |

Abreviations: +: 1 log;

EXAMPLE 9: ANTIMICROBIAL ACTIVITY OF THE *ACINETOBACTER BAUMANNII* ENDOLYSIN MODIFIED WITH VARIOUS PEPTIDE STRETCHES ON THE N-TERMINUS

The fusion proteins consisting of the *Acinetobacter baumannii* endolysin having an amino acid sequence according to SEQ ID NO: 5 and the peptide stretches SMAP-29, Pseudin 1 and Sushi 1 were constructed analogous to example 3. *Acinetobacter baumannii* DSMZ 30007 and *Pseudomonas aeruginosa* PAO1p cells (Burn wound isolate, Queen Astrid Hospital, Brussels; Pirnay J P et al. (2003), *J Clin Microbiol.*, 41(3):1192-1202) were used as test strains. The antimicrobial activity of the fusion proteins was examined as described in example 4. The antimicrobial activity of these fusion proteins is given in the following table.

TABLE 16

| Fusion protein | Enzyme part | Peptide stretch (N-terminal unless otherwise indicated) | Activity against *Pseudomonas aeruginosa* | Activity against *Acinetobacter baumannii* DSMZ 30007 |
| --- | --- | --- | --- | --- |
| SEQ ID NO: 98 | *Acinetobacter baumannii* endolysin (SEQ ID NO: 5) | Pseudin 1 (SEQ ID NO: 29) | ± | n.d. |
| SEQ ID NO: 99 | *Acinetobacter baumannii* endolysin (SEQ ID NO: 5) | SMAP-29 (SEQ ID NO: 11) | ++ | ++ |
| SEQ ID NO: 100 | *Acinetobacter baumannii* endolysin (SEQ ID NO: 5) | Sushi 1 (SEQ ID NO: 32) | + | + |

Abreviations: ± <1 log; +: 1 log; ++: 2-3 log; n.d. means that this strain was not tested with the respective fusion protein.

The fusion proteins in Table 11 to 16 without any tag and linker were also tested with the activity assays described above. They all showed antimicrobial activity against the used bacterial strains (data not shown).

The invention claimed is:

1. A fusion protein comprising an endolysin having the activity of degrading the cell wall of Gram-negative bacteria and a peptide segment fused to the endolysin at the N- or C-terminus or at both termini, wherein the peptide segment is a cathelicidine or a magainine.

2. The fusion protein according to claim 1, wherein the peptide segment consists of about 12 to about 100 amino acid residues.

3. The fusion protein according to claim 2, wherein the peptide segment consists of about 12 to 50 amino acid residues.

4. The fusion protein according to claim 2, wherein the peptide segment consists of about 12 to 30 amino acid residues.

5. The fusion protein according to claim 1, wherein said fusion protein comprises an additional amino acid residue on the N-terminus.

6. The fusion protein according to claim 1, wherein said fusion protein comprises a tag or additional protein on the C- and/or N-terminus.

7. The fusion protein according to claim 1, wherein the peptide segment is linked to the endolysin by one or more additional amino acid residues.

8. The fusion protein according to claim 1, wherein the endolysin comprises an amino acid sequence according to any of SEQ ID NO: 1, 2, 3, 4, 5, 18, 20, 21, 22, 23, 24, 25 or 34.

9. The fusion protein according to claim 1, wherein the peptide segment comprises an amino acid sequence according to any of SEQ ID NO: 9, 10, 11, 12, or 13.

10. The fusion protein according to claim 1, wherein the Gram-negative bacteria are selected from the group consisting of:

Enterobacteriaceae, Pseudomonadaceae, *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella,* Spirochaetaceae, Leptospiraceae, *Campylobacter, Helicobacter, Spirillum, Streptobacillus,* Bacteroidaceae and *Acinetobacter.*

11. The fusion protein according to claim 10, wherein the Gram-negative bacteria are selected from the group consisting of *Escherichia, Salmonella, Shingella, Citrobacter, Edwardsiella, Enterobacter, Hafnia, Klebsiella, Moganella, Proteus, Providencia, Serratia, Yersinia, Pseudomonas, Burkholderia, Stenotrophomonas, Shewanella, Sphingomonas, Comamonas, Treponema, Borrelia, Bacteroides, Fusobacterium, Prevotella, Porphyromonas* and *A. baumanii.*

12. An isolated nucleic acid molecule encoding a fusion protein according to claim 1.

13. A vector comprising the nucleic acid molecule according to claim 12.

14. A host cell comprising the nucleic acid molecule according to claim 12 or the vector according to claim 13.

15. The host cell according to claim 14, wherein the cell is a bacterial cell or a yeast cell.

16. A pharmaceutical composition comprising a fusion protein according to claim 1.

17. A fusion protein comprising an endolysin having the activity of degrading the cell wall of Gram-negative bacteria and a peptide segment fused to the endolysin at the N- or C-terminus or at both termini, wherein the peptide segment comprises SEQ ID NO: 33.

* * * * *

```
                              SEQUENCE LISTING

<160> NUMBER OF SEQ ID NOS: 100

<210> SEQ ID NO 1
<211> LENGTH: 260
<212> TYPE: PRT
<213> ORGANISM: unknown
<220> FEATURE:
<223> OTHER INFORMATION: phiKZgp144

<400> SEQUENCE: 1

Met Lys Val Leu Arg Lys Gly Asp Arg Gly Asp Glu Val Cys Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Cys Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
65                  70                  75                  80

Pro Thr Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Ile Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Met Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Gly Pro Gly Ala Ala Arg
        195                 200                 205

Arg Phe Leu Thr Thr Gly Gln Asn Glu Leu Ala Ala Thr His Phe Pro
    210                 215                 220

Lys Glu Ala Gln Ala Asn Pro Ser Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 2
<211> LENGTH: 292
<212> TYPE: PRT
<213> ORGANISM: unknown
<220> FEATURE:
<223> OTHER INFORMATION: ELgp188

<400> SEQUENCE: 2

Met Asn Phe Arg Thr Lys Asn Gly Tyr Arg Asp Leu Gln Ala Leu Val
1               5                   10                  15
```

```
Lys Glu Leu Gly Leu Tyr Thr Gly Gln Ile Asp Gly Val Trp Gly Lys
                20                  25                  30

Gly Thr Ser Ser Ser Thr Glu Thr Leu Leu Arg Gly Tyr Ala Glu Val
            35                  40                  45

Val Gly Lys Asn Thr Gly Gly Ile Gly Leu Pro Thr Thr Ser Asp Ala
50                  55                  60

Ser Gly Tyr Asn Val Ile Thr Ala Leu Gln Arg Asn Leu Ala Phe Leu
65                  70                  75                  80

Gly Leu Tyr Ser Leu Thr Val Asp Gly Ile Trp Gly Asn Gly Thr Leu
                85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
        115                 120                 125

Ala Lys Val Lys Asp Trp Cys Gly Val His Val Pro Asn His Arg Ala
    130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
    210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr
    290

<210> SEQ ID NO 3
<211> LENGTH: 181
<212> TYPE: PRT
<213> ORGANISM: unknown
<220> FEATURE:
<223> OTHER INFORMATION: Salmonella endolysin

<400> SEQUENCE: 3

Met Lys Pro Lys Asp Glu Ile Phe Asp Glu Ile Leu Gly Lys Glu Gly
1               5                   10                  15

Gly Tyr Val Asn His Pro Asp Asp Lys Gly Gly Pro Thr Lys Trp Gly
                20                  25                  30

Ile Thr Glu Lys Val Ala Arg Ala His Gly Tyr Arg Gly Asp Met Arg
            35                  40                  45

Asn Leu Thr Arg Gly Gln Ala Leu Glu Ile Leu Glu Thr Asp Tyr Trp
        50                  55                  60

Tyr Gly Pro Arg Phe Asp Arg Val Ala Lys Ala Ser Pro Asp Val Ala
65                  70                  75                  80
```

```
Ala Glu Leu Cys Asp Thr Gly Val Asn Met Gly Pro Ser Val Ala Ala
                85                  90                  95

Lys Met Leu Gln Arg Trp Leu Asn Val Phe Asn Gln Gly Gly Arg Leu
            100                 105                 110

Tyr Pro Asp Met Asp Thr Asp Gly Arg Ile Gly Pro Arg Thr Leu Asn
        115                 120                 125

Ala Leu Arg Val Tyr Leu Glu Lys Arg Gly Lys Asp Gly Glu Arg Val
    130                 135                 140

Leu Leu Val Ala Leu Asn Cys Thr Gln Gly Glu Arg Tyr Leu Glu Leu
145                 150                 155                 160

Ala Glu Lys Arg Glu Ala Asp Glu Ser Phe Val Tyr Gly Trp Met Lys
                165                 170                 175

Glu Arg Val Leu Ile
            180

<210> SEQ ID NO 4
<211> LENGTH: 163
<212> TYPE: PRT
<213> ORGANISM: unknown
<220> FEATURE:
<223> OTHER INFORMATION: Enterobacteria phage T4 endolysin

<400> SEQUENCE: 4

Met Asn Ile Phe Glu Met Leu Arg Ile Asp Glu Gly Leu Arg Leu Lys
1               5                   10                  15

Ile Tyr Lys Asp Thr Glu Gly Tyr Tyr Thr Ile Gly Ile Gly His Leu
                20                  25                  30

Leu Thr Lys Ser Pro Ser Leu Asn Ala Ala Lys Ser Glu Leu Asp Lys
            35                  40                  45

Ala Ile Gly Arg Asn Cys Asn Gly Val Ile Thr Lys Asp Glu Ala Glu
        50                  55                  60

Lys Leu Phe Asn Gln Asp Val Asp Ala Ala Val Arg Gly Ile Leu Arg
65                  70                  75                  80

Asn Ala Lys Leu Lys Pro Val Tyr Asp Ser Leu Asp Ala Val Arg Arg
                85                  90                  95

Cys Ala Leu Ile Asn Met Val Phe Gln Met Gly Glu Thr Gly Val Ala
            100                 105                 110

Gly Phe Thr Asn Ser Leu Arg Met Leu Gln Gln Lys Arg Trp Asp Glu
        115                 120                 125

Ala Ala Val Asn Leu Ala Lys Ser Arg Trp Tyr Asn Gln Thr Pro Asn
    130                 135                 140

Arg Ala Lys Arg Val Ile Thr Thr Phe Arg Thr Gly Thr Trp Asp Ala
145                 150                 155                 160

Tyr Lys Asn

<210> SEQ ID NO 5
<211> LENGTH: 280
<212> TYPE: PRT
<213> ORGANISM: unknown
<220> FEATURE:
<223> OTHER INFORMATION: Acinetobacter baumanii endolysin

<400> SEQUENCE: 5

Met Glu Tyr Asp Met Ile Leu Lys Phe Gly Ser Lys Gly Asp Ala Val
1               5                   10                  15

Ala Thr Leu Gln Lys Gln Leu Ala Lys Met Gly Tyr Lys Gly Val Lys
                20                  25                  30
```

```
Asp Lys Pro Leu Ser Val Asp Gly His Phe Gly Glu Ser Thr Glu Phe
         35                  40                  45

Ala Val Ile Gln Leu Gln Arg Lys Phe Gly Leu Val Ala Asp Gly Lys
 50                  55                  60

Val Gly Asp Lys Thr Arg Gln Ala Leu Ala Gly Asp Ser Val Ser Lys
 65                  70                  75                  80

Phe Leu Lys Asp Glu Asp Tyr Lys Lys Ala Ala Ile Arg Leu Lys Val
                 85                  90                  95

Pro Glu Leu Val Ile Arg Val Phe Gly Ala Val Glu Gly Leu Gly Val
                100                 105                 110

Gly Phe Leu Pro Asn Gly Lys Ala Lys Ile Leu Phe Glu Arg His Arg
            115                 120                 125

Met Tyr Phe Tyr Leu Cys Gln Ala Leu Gly Lys Thr Phe Ala Asn Ser
130                 135                 140

Gln Val Lys Ile Thr Pro Asn Ile Val Asn Thr Leu Thr Gly Gly Tyr
145                 150                 155                 160

Lys Gly Asp Ala Ala Glu Tyr Thr Arg Leu Ser Met Ala Ile Asn Ile
                165                 170                 175

His Lys Glu Ser Ala Leu Met Ser Thr Ser Trp Gly Gln Phe Gln Ile
                180                 185                 190

Met Gly Glu Asn Trp Lys Asp Leu Gly Tyr Ser Ser Val Gln Glu Phe
            195                 200                 205

Val Asp Gln Gln Gln Leu Asn Glu Gly Asn Gln Leu Glu Ala Phe Ile
210                 215                 220

Arg Phe Ile Glu Trp Lys Pro Gly Leu Leu Glu Ala Leu Arg Lys Gln
225                 230                 235                 240

Asp Trp Asp Thr Val Phe Thr Leu Tyr Asn Gly Lys Asn Tyr Lys Lys
                245                 250                 255

Leu Gly Tyr Gln Ala Lys Phe Gln Lys Glu Trp Asp His Leu Glu Pro
                260                 265                 270

Ile Tyr Arg Glu Lys Thr Ala Ala
                275                 280

<210> SEQ ID NO 6
<211> LENGTH: 25
<212> TYPE: PRT
<213> ORGANISM: unknown
<220> FEATURE:
<223> OTHER INFORMATION: amphipatic peptide Pleurocidin

<400> SEQUENCE: 6

Gly Trp Gly Ser Phe Phe Lys Lys Ala Ala His Val Gly Lys His Val
 1               5                  10                  15

Gly Lys Ala Ala Leu Thr His Tyr Leu
            20                  25

<210> SEQ ID NO 7
<211> LENGTH: 31
<212> TYPE: PRT
<213> ORGANISM: unknown
<220> FEATURE:
<223> OTHER INFORMATION: amphipatic peptide Cecropin P1

<400> SEQUENCE: 7

Ser Trp Leu Ser Lys Thr Ala Lys Lys Leu Glu Asn Ser Ala Lys Lys
 1               5                  10                  15

Arg Ile Ser Glu Gly Ile Ala Ile Ala Ile Gln Gly Gly Pro Arg
            20                  25                  30
```

<210> SEQ ID NO 8
<211> LENGTH: 21
<212> TYPE: PRT
<213> ORGANISM: unknown
<220> FEATURE:
<223> OTHER INFORMATION: amphipatic peptide Buforin II

<400> SEQUENCE: 8

Thr Arg Ser Ser Arg Ala Gly Leu Gln Phe Pro Val Gly Arg Val His
1               5                   10                  15

Arg Leu Leu Arg Lys
            20

<210> SEQ ID NO 9
<211> LENGTH: 23
<212> TYPE: PRT
<213> ORGANISM: unknown
<220> FEATURE:
<223> OTHER INFORMATION: amphipatic peptide Magainin

<400> SEQUENCE: 9

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 10
<211> LENGTH: 37
<212> TYPE: PRT
<213> ORGANISM: unknown
<220> FEATURE:
<223> OTHER INFORMATION: amphipatic peptides Cathelidicine LL-37

<400> SEQUENCE: 10

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 11
<211> LENGTH: 29
<212> TYPE: PRT
<213> ORGANISM: unknown
<220> FEATURE:
<223> OTHER INFORMATION: SMAP-29

<400> SEQUENCE: 11

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 12
<211> LENGTH: 13
<212> TYPE: PRT
<213> ORGANISM: unknown
<220> FEATURE:
<223> OTHER INFORMATION: Indolicidin

<400> SEQUENCE: 12

Ile Leu Pro Trp Lys Trp Pro Trp Trp Pro Trp Arg Arg

```
<210> SEQ ID NO 13
<211> LENGTH: 18
<212> TYPE: PRT
<213> ORGANISM: unknown
<220> FEATURE:
<223> OTHER INFORMATION: Protegrin

<400> SEQUENCE: 13

Arg Gly Gly Arg Leu Cys Tyr Cys Arg Arg Arg Phe Cys Val Cys Val
1               5                   10                  15

Gly Arg

<210> SEQ ID NO 14
<211> LENGTH: 36
<212> TYPE: PRT
<213> ORGANISM: unknown
<220> FEATURE:
<223> OTHER INFORMATION: Cecropin A (A.aegypti)

<400> SEQUENCE: 14

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
                20                  25                  30

Ala Leu Arg Lys
        35

<210> SEQ ID NO 15
<211> LENGTH: 40
<212> TYPE: PRT
<213> ORGANISM: unknown
<220> FEATURE:
<223> OTHER INFORMATION: Cecropin A (D. melanogaster)

<400> SEQUENCE: 15

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
                20                  25                  30

Asn Val Ala Ala Thr Ala Arg Gly
        35                  40

<210> SEQ ID NO 16
<211> LENGTH: 39
<212> TYPE: PRT
<213> ORGANISM: unknown
<220> FEATURE:
<223> OTHER INFORMATION: Sarcotoxin IA

<400> SEQUENCE: 16

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
                20                  25                  30

Asn Val Ala Ala Thr Ala Arg
        35

<210> SEQ ID NO 17
<211> LENGTH: 5
<212> TYPE: PRT
<213> ORGANISM: unknown
```

-continued

```
<220> FEATURE:
<223> OTHER INFORMATION: Synthetic peptide

<400> SEQUENCE: 17

Phe Phe Val Ala Pro
1               5

<210> SEQ ID NO 18
<211> LENGTH: 152
<212> TYPE: PRT
<213> ORGANISM: unknown
<220> FEATURE:
<223> OTHER INFORMATION: E. coli phage K1F

<400> SEQUENCE: 18

Met Val Ser Lys Val Gln Phe Asn Pro Arg Ser Arg Thr Asp Ala Ile
1               5                   10                  15

Phe Val His Cys Ser Ala Thr Lys Pro Glu Met Asp Ile Gly Val Glu
                20                  25                  30

Thr Ile Arg Met Trp His Lys Gln Gln Ala Trp Leu Asp Val Gly Tyr
            35                  40                  45

His Phe Ile Ile Lys Arg Asp Gly Thr Val Glu Glu Gly Arg Pro Val
    50                  55                  60

Asn Val Val Gly Ser His Val Lys Asp Trp Asn Ser Arg Ser Val Gly
65                  70                  75                  80

Val Cys Leu Val Gly Ile Asn Ala Lys Gly Gln Phe Glu Ala Asn
                85                  90                  95

Phe Thr Pro Ala Gln Met Asn Ser Leu Arg Asn Lys Leu Asp Asp Leu
            100                 105                 110

Lys Val Met Tyr Pro Gln Ala Glu Ile Arg Ala His His Asp Val Ala
        115                 120                 125

Pro Lys Ala Cys Pro Ser Phe Asp Leu Gln Arg Trp Leu Ser Thr Asn
    130                 135                 140

Glu Leu Val Thr Ser Asp Arg Gly
145                 150

<210> SEQ ID NO 19
<211> LENGTH: 39
<212> TYPE: PRT
<213> ORGANISM: unknown
<220> FEATURE:
<223> OTHER INFORMATION: Buforin I

<400> SEQUENCE: 19

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
                20                  25                  30

Leu Leu Arg Lys Gly Asn Tyr
            35

<210> SEQ ID NO 20
<211> LENGTH: 165
<212> TYPE: PRT
<213> ORGANISM: unknown
<220> FEATURE:
<223> OTHER INFORMATION: PSP3 gp10 Salmonella endolysin

<400> SEQUENCE: 20

Met Pro Val Ile Asn Thr His Gln Asn Ile Ala Ala Phe Leu Asp Met
1               5                   10                  15
```

Leu Ala Tyr Ser Glu Gly Thr Ala Asn His Pro Leu Thr Lys Asn Arg
            20                  25                  30

Gly Tyr Asp Val Ile Val Thr Gly Phe Asp Gly Ser Pro Glu Ile Phe
                35                  40                  45

Thr Asp Tyr Ser Asp His Pro Phe Ala His Gly Arg Pro Pro Lys Val
 50                  55                  60

Phe Asn Arg Arg Gly Glu Lys Ser Thr Ala Ser Gly Arg Tyr Gln Gln
 65                  70                  75                  80

Leu Tyr Ile Phe Trp Pro His Tyr Lys Lys Gln Leu Ala Leu Pro Asp
                85                  90                  95

Phe Ser Pro Leu Ser Gln Asp Lys Leu Ala Ile Gln Leu Ile Arg Glu
            100                 105                 110

Arg Gly Ala Ile Asp Asp Ile Arg Ala Gly Arg Ile Glu Arg Ala Val
            115                 120                 125

Ser Arg Cys Arg Asn Ile Trp Ala Ser Leu Pro Gly Ala Gly Tyr Gly
130                 135                 140

Gln Arg Glu His Ser Leu Glu Lys Leu Val Thr Val Trp Arg Thr Ala
145                 150                 155                 160

Gly Gly Val Met Ala
            165

<210> SEQ ID NO 21
<211> LENGTH: 165
<212> TYPE: PRT
<213> ORGANISM: unknown
<220> FEATURE:
<223> OTHER INFORMATION: E. coli phage endolysin P2gp09

<400> SEQUENCE: 21

Met Pro Val Ile Asn Thr His Gln Asn Ile Ala Ala Phe Leu Asp Met
 1               5                  10                  15

Leu Ala Val Ser Glu Gly Thr Ala Asn His Pro Leu Thr Lys Asn Arg
            20                  25                  30

Gly Tyr Asp Val Ile Val Thr Gly Leu Asp Gly Lys Pro Glu Ile Phe
                35                  40                  45

Thr Asp Tyr Ser Asp His Pro Phe Ala His Gly Arg Pro Ala Lys Val
 50                  55                  60

Phe Asn Arg Arg Gly Glu Lys Ser Thr Ala Ser Gly Arg Tyr Gln Gln
 65                  70                  75                  80

Leu Tyr Leu Phe Trp Pro His Tyr Arg Lys Gln Leu Ala Leu Pro Asp
                85                  90                  95

Phe Ser Pro Leu Ser Gln Asp Arg Leu Ala Ile Gln Leu Ile Arg Glu
            100                 105                 110

Arg Gly Ala Leu Asp Asp Ile Arg Ala Gly Arg Ile Glu Arg Ala Ile
            115                 120                 125

Ser Arg Cys Arg Asn Ile Trp Ala Ser Leu Pro Gly Ala Gly Tyr Gly
130                 135                 140

Gln Arg Glu His Ser Leu Glu Lys Leu Val Thr Val Trp Arg Thr Ala
145                 150                 155                 160

Gly Gly Val Pro Ala
            165

<210> SEQ ID NO 22
<211> LENGTH: 176
<212> TYPE: PRT
<213> ORGANISM: unknown

<220> FEATURE:
<223> OTHER INFORMATION: STM0016

<400> SEQUENCE: 22

Asn Pro Ile Ile Asp Gly Ile Ile Ala Leu Glu Gly Gly Tyr Val Phe
1               5                   10                  15

Asn Pro Lys Asp Lys Gly Gly Ala Thr His Trp Gly Ile Thr Glu Ala
            20                  25                  30

Thr Ala Arg Ala His Gly Tyr Ala Gly Asp Met Arg Asp Leu Thr His
        35                  40                  45

Ala Glu Ala Tyr Ala Ile Leu Glu Gly Asp Tyr Trp Ile Lys Pro Gly
50                  55                  60

Phe Asp Val Ile Ser Thr Leu Ser Trp Pro Val Ser Phe Glu Leu Cys
65                  70                  75                  80

Asp Ala Ala Val Asn Ile Gly Ala Tyr His Pro Ser Ala Trp Leu Gln
                85                  90                  95

Arg Trp Leu Asn Val Phe Asn His Glu Gly Lys Arg Tyr Pro Asp Ile
            100                 105                 110

His Val Asp Gly Asn Ile Gly Pro Arg Thr Leu Ala Ala Leu Glu His
        115                 120                 125

Tyr Leu Ala Trp Arg Gly Gln Glu Gly Glu Ala Val Leu Val Lys Ala
130                 135                 140

Leu Asn Cys Ser Gln Gly Thr Tyr Tyr Leu Asn Val Ala Glu Lys Asn
145                 150                 155                 160

His Asn Asn Glu Gln Phe Ile Tyr Gly Trp Ile Lys Asn Arg Val Thr
                165                 170                 175

<210> SEQ ID NO 23
<211> LENGTH: 208
<212> TYPE: PRT
<213> ORGANISM: unknown
<220> FEATURE:
<223> OTHER INFORMATION: E.coli Phage N4 muramidase N4-gp61

<400> SEQUENCE: 23

Met Ala Ile Ser Lys Lys Val Gly Val Gly Gly Val Ile Ala
1               5                   10                  15

Ala Ile Ile Ala Ala Val Phe Ala Val Glu Gly Gly Tyr Val Asn Asp
            20                  25                  30

Pro Lys Asp Pro Gly Gly Glu Thr Asn His Gly Val Thr Ile Gln Val
        35                  40                  45

Ala Gln Lys His Lys Gln Glu Leu Glu Ser Met Tyr Asn Trp Asp Gly
50                  55                  60

Ser Met Lys Asn Leu Thr Gln Glu Met Ala Ser Ser Ile Tyr Tyr Asn
65                  70                  75                  80

Asp Tyr Ile Leu Lys Pro Gly Phe Val Lys Phe Ala Asp Val Ser Pro
                85                  90                  95

Ala Val Thr Glu Lys Leu Val Asp Ala Gly Val Asn Thr Gly Pro Ala
            100                 105                 110

Arg Pro Ser Arg Trp Leu Gln Glu Ser Leu Asn Ala Phe Ser Arg Asn
        115                 120                 125

Gly Lys Asp Tyr Pro Lys Ile Gln Val Asp Gly Lys Val Gly Ser Gly
130                 135                 140

Thr Leu Ser Ala Tyr Lys Ser Leu Gln Asn Lys Arg Gly Lys Val Glu
145                 150                 155                 160

Ala Cys Lys Leu Ile Leu Lys Ser Leu Asp Gly Lys Gln Leu Asn Tyr 165                 170                 175

Tyr Leu Ser Leu Asn Met Pro Glu Tyr Thr Thr Gly Trp Ile Ala Asn
            180                 185                 190

Arg Ile Gly Asn Val Pro Leu Glu Arg Cys Asn Glu Asp Ile Val Asn
        195                 200                 205

<210> SEQ ID NO 24
<211> LENGTH: 184
<212> TYPE: PRT
<213> ORGANISM: unknown
<220> FEATURE:
<223> OTHER INFORMATION: 24 N4-gp61 trunc.

<400> SEQUENCE: 24

Val Glu Gly Gly Tyr Val Asn Asp Pro Lys Asp Pro Gly Gly Glu Thr
1               5                   10                  15

Asn His Gly Val Thr Ile Gln Val Ala Gln Lys His Lys Gln Glu Leu
            20                  25                  30

Glu Ser Met Tyr Asn Trp Asp Gly Ser Met Lys Asn Leu Thr Gln Glu
        35                  40                  45

Met Ala Ser Ser Ile Tyr Tyr Asn Asp Tyr Ile Leu Lys Pro Gly Phe
    50                  55                  60

Val Lys Phe Ala Asp Val Ser Pro Ala Val Thr Glu Lys Leu Val Asp
65                  70                  75                  80

Ala Gly Val Asn Thr Gly Pro Ala Arg Pro Ser Arg Trp Leu Gln Glu
                85                  90                  95

Ser Leu Asn Ala Phe Ser Arg Asn Gly Lys Asp Tyr Pro Lys Ile Gln
            100                 105                 110

Val Asp Gly Lys Val Gly Ser Gly Thr Leu Ser Ala Tyr Lys Ser Leu
        115                 120                 125

Gln Asn Lys Arg Gly Lys Val Glu Ala Cys Lys Leu Ile Leu Lys Ser
    130                 135                 140

Leu Asp Gly Lys Gln Leu Asn Tyr Tyr Leu Ser Leu Asn Met Pro Glu
145                 150                 155                 160

Tyr Thr Thr Gly Trp Ile Ala Asn Arg Ile Gly Asn Val Pro Leu Glu
                165                 170                 175

Arg Cys Asn Glu Asp Ile Val Asn
            180

<210> SEQ ID NO 25
<211> LENGTH: 259
<212> TYPE: PRT
<213> ORGANISM: unknown
<220> FEATURE:
<223> OTHER INFORMATION: E.coli phage KZ144

<400> SEQUENCE: 25

Lys Val Leu Arg Lys Gly Asp Arg Gly Asp Glu Val Cys Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Cys Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80

```
Thr Ala Asn Lys Ser Arg Ala Ala Thr Pro Val Met Asn Ala Val
            85                  90                  95
Glu Asn Ala Thr Gly Val Arg Ser Gln Leu Leu Leu Thr Phe Ala Ser
            100                 105                 110
Ile Glu Ser Ala Phe Asp Tyr Glu Ile Lys Ala Lys Thr Ser Ser Ala
            115                 120                 125
Thr Gly Trp Phe Gln Phe Leu Thr Gly Thr Trp Lys Thr Met Ile Glu
            130                 135                 140
Asn Tyr Gly Met Lys Tyr Gly Val Leu Thr Asp Pro Thr Gly Ala Leu
145                 150                 155                 160
Arg Lys Asp Pro Arg Ile Ser Ala Leu Met Gly Ala Glu Leu Ile Lys
            165                 170                 175
Glu Asn Met Asn Ile Leu Arg Pro Val Leu Lys Arg Glu Pro Thr Asp
            180                 185                 190
Thr Asp Leu Tyr Leu Ala His Phe Phe Gly Pro Gly Ala Ala Arg Arg
            195                 200                 205
Phe Leu Thr Thr Gly Gln Asn Glu Leu Ala Ala Thr His Phe Pro Lys
            210                 215                 220
Glu Ala Gln Ala Asn Pro Ser Ile Phe Tyr Asn Lys Asp Gly Ser Pro
225                 230                 235                 240
Lys Thr Ile Gln Glu Val Tyr Asn Leu Met Asp Gly Lys Val Ala Ala
            245                 250                 255
His Arg Lys

<210> SEQ ID NO 26
<211> LENGTH: 22
<212> TYPE: PRT
<213> ORGANISM: unknown
<220> FEATURE:
<223> OTHER INFORMATION: Nigrocine 2

<400> SEQUENCE: 26

Gly Leu Leu Ser Lys Val Leu Gly Val Gly Lys Lys Val Leu Cys Gly
1               5                   10                  15
Val Ser Gly Leu Val Cys
            20

<210> SEQ ID NO 27
<211> LENGTH: 24
<212> TYPE: PRT
<213> ORGANISM: unknown
<220> FEATURE:
<223> OTHER INFORMATION: Ascaphine 5

<400> SEQUENCE: 27

Gly Ile Lys Asp Trp Ile Lys Gly Ala Ala Lys Lys Leu Ile Lys Thr
1               5                   10                  15
Val Ala Ser His Ile Ala Asn Gln
            20

<210> SEQ ID NO 28
<211> LENGTH: 17
<212> TYPE: PRT
<213> ORGANISM: unknown
<220> FEATURE:
<223> OTHER INFORMATION: Apidaecin

<400> SEQUENCE: 28

Ala Asn Arg Pro Val Tyr Ile Pro Pro Pro Arg Pro Pro His Pro Arg
1               5                   10                  15
```

Leu

<210> SEQ ID NO 29
<211> LENGTH: 24
<212> TYPE: PRT
<213> ORGANISM: unknown
<220> FEATURE:
<223> OTHER INFORMATION: Pseudin 1

<400> SEQUENCE: 29

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 30
<211> LENGTH: 18
<212> TYPE: PRT
<213> ORGANISM: unknown
<220> FEATURE:
<223> OTHER INFORMATION: Ranalexin

<400> SEQUENCE: 30

Phe Leu Gly Gly Leu Ile Val Pro Ala Met Ile Cys Ala Val Thr Lys
1               5                   10                  15

Lys Cys

<210> SEQ ID NO 31
<211> LENGTH: 26
<212> TYPE: PRT
<213> ORGANISM: unknown
<220> FEATURE:
<223> OTHER INFORMATION: Melittin

<400> SEQUENCE: 31

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 32
<211> LENGTH: 34
<212> TYPE: PRT
<213> ORGANISM: unknown
<220> FEATURE:
<223> OTHER INFORMATION: Sushi 1

<400> SEQUENCE: 32

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser

<210> SEQ ID NO 33
<211> LENGTH: 27
<212> TYPE: PRT
<213> ORGANISM: unknown
<220> FEATURE:
<223> OTHER INFORMATION: WLUB2 variant

<400> SEQUENCE: 33

Lys Arg Trp Val Lys Arg Val Lys Arg Val Lys Arg Trp Val Lys Arg

```
                1               5                   10                  15
        Val Val Arg Val Val Lys Arg Trp Val Lys Arg
                        20                  25
```

<210> SEQ ID NO 34
<211> LENGTH: 332
<212> TYPE: PRT
<213> ORGANISM: unknown
<220> FEATURE:
<223> OTHER INFORMATION: OBPgpLYS

<400> SEQUENCE: 34

```
Met Gly Ser Lys Asn Ser Glu Lys Asn Ala Ser Ile Ile Met Ser Ile
1               5                   10                  15

Gln Arg Thr Leu Ala Ser Leu Ser Leu Tyr Gly Gly Arg Ile Asp Gly
            20                  25                  30

Leu Phe Gly Glu Lys Cys Arg Gly Ala Ile Ile Leu Met Leu Asn Lys
        35                  40                  45

Val Tyr Pro Asn Phe Ser Thr Asn Lys Leu Pro Ser Asn Thr Tyr Glu
    50                  55                  60

Ala Glu Ser Val Phe Thr Phe Leu Gln Thr Ala Leu Ala Gly Val Gly
65                  70                  75                  80

Leu Tyr Thr Ile Thr Ile Asp Gly Lys Trp Gly Thr Ser Gln Gly
                85                  90                  95

Ala Ile Asp Ala Leu Val Lys Ser Tyr Arg Gln Ile Thr Glu Ala Glu
            100                 105                 110

Arg Ala Gly Ser Thr Leu Pro Leu Gly Leu Ala Thr Val Met Ser Lys
        115                 120                 125

His Met Ser Ile Glu Gln Leu Arg Ala Met Leu Pro Thr Asp Arg Gln
    130                 135                 140

Gly Tyr Ala Glu Val Tyr Ile Asp Pro Leu Asn Glu Thr Met Asp Ile
145                 150                 155                 160

Phe Glu Ile Asn Thr Pro Leu Arg Ile Ala His Phe Met Ala Gln Ile
                165                 170                 175

Leu His Glu Thr Ala Cys Phe Lys Tyr Thr Glu Glu Leu Ala Ser Gly
            180                 185                 190

Lys Ala Tyr Glu Gly Arg Ala Asp Leu Gly Asn Thr Arg Pro Gly Asp
        195                 200                 205

Gly Pro Leu Phe Lys Gly Arg Gly Leu Leu Gln Ile Thr Gly Arg Leu
    210                 215                 220

Asn Tyr Val Lys Cys Gln Val Tyr Leu Arg Glu Lys Leu Lys Asp Pro
225                 230                 235                 240

Thr Phe Asp Ile Thr Ser Ser Val Thr Cys Ala Gln Gln Leu Ser Glu
                245                 250                 255

Ser Pro Leu Leu Ala Ala Leu Ala Ser Gly Tyr Phe Trp Arg Phe Ile
            260                 265                 270

Lys Pro Lys Leu Asn Glu Thr Ala Asp Lys Asp Ile Tyr Trp Val
        275                 280                 285

Ser Val Tyr Val Asn Gly Tyr Ala Lys Gln Ala Asn Pro Tyr Tyr Pro
    290                 295                 300

Asn Arg Asp Lys Glu Pro Asn His Met Lys Glu Arg Val Gln Met Leu
305                 310                 315                 320

Ala Val Thr Lys Lys Ala Leu Gly Ile Val Lys Gly
                325                 330
```

```
<210> SEQ ID NO 35
<211> LENGTH: 18
<212> TYPE: PRT
<213> ORGANISM: unknown
<220> FEATURE:
<223> OTHER INFORMATION: 35 Walmagh1

<400> SEQUENCE: 35

Gly Phe Phe Ile Pro Ala Val Ile Leu Pro Ser Ile Ala Phe Leu Ile
1               5                   10                  15

Val Pro

<210> SEQ ID NO 36
<211> LENGTH: 283
<212> TYPE: PRT
<213> ORGANISM: unknown
<220> FEATURE:
<223> OTHER INFORMATION: Ascaphine5-KZ144

<400> SEQUENCE: 36

Gly Ile Lys Asp Trp Ile Lys Gly Ala Ala Lys Lys Leu Ile Lys Thr
1               5                   10                  15

Val Ala Ser His Ile Ala Asn Gln Lys Val Leu Arg Lys Gly Asp Arg
                20                  25                  30

Gly Asp Glu Val Cys Gln Leu Gln Thr Leu Leu Asn Leu Cys Gly Tyr
            35                  40                  45

Asp Val Gly Lys Pro Asp Gly Ile Phe Gly Asn Asn Thr Phe Asn Gln
        50                  55                  60

Val Val Lys Phe Gln Lys Asp Asn Cys Leu Asp Ser Asp Gly Ile Val
65                  70                  75                  80

Gly Lys Asn Thr Trp Ala Glu Leu Phe Ser Lys Tyr Ser Pro Pro Ile
                85                  90                  95

Pro Tyr Lys Thr Ile Pro Met Pro Thr Ala Asn Lys Ser Arg Ala Ala
            100                 105                 110

Ala Thr Pro Val Met Asn Ala Val Glu Asn Ala Thr Gly Val Arg Ser
        115                 120                 125

Gln Leu Leu Leu Thr Phe Ala Ser Ile Glu Ser Ala Phe Asp Tyr Glu
130                 135                 140

Ile Lys Ala Lys Thr Ser Ser Ala Thr Gly Trp Phe Gln Phe Leu Thr
145                 150                 155                 160

Gly Thr Trp Lys Thr Met Ile Glu Asn Tyr Gly Met Lys Tyr Gly Val
                165                 170                 175

Leu Thr Asp Pro Thr Gly Ala Leu Arg Lys Asp Pro Arg Ile Ser Ala
            180                 185                 190

Leu Met Gly Ala Glu Leu Ile Lys Glu Asn Met Asn Ile Leu Arg Pro
        195                 200                 205

Val Leu Lys Arg Glu Pro Thr Asp Thr Asp Leu Tyr Leu Ala His Phe
210                 215                 220

Phe Gly Pro Gly Ala Ala Arg Arg Phe Leu Thr Thr Gly Gln Asn Glu
225                 230                 235                 240

Leu Ala Ala Thr His Phe Pro Lys Glu Ala Gln Ala Asn Pro Ser Ile
                245                 250                 255

Phe Tyr Asn Lys Asp Gly Ser Pro Lys Thr Ile Gln Glu Val Tyr Asn
            260                 265                 270

Leu Met Asp Gly Lys Val Ala Ala His Arg Lys
        275                 280
```

-continued

```
<210> SEQ ID NO 37
<211> LENGTH: 276
<212> TYPE: PRT
<213> ORGANISM: unknown
<220> FEATURE:
<223> OTHER INFORMATION: Apidaecine-KZ144

<400> SEQUENCE: 37

Ala Asn Arg Pro Val Tyr Ile Pro Pro Arg Pro Pro His Pro Arg
1               5                   10                  15

Leu Lys Val Leu Arg Lys Gly Asp Arg Gly Asp Glu Val Cys Gln Leu
            20                  25                  30

Gln Thr Leu Leu Asn Leu Cys Gly Tyr Asp Val Gly Lys Pro Asp Gly
        35                  40                  45

Ile Phe Gly Asn Asn Thr Phe Asn Gln Val Val Lys Phe Gln Lys Asp
50                  55                  60

Asn Cys Leu Asp Ser Asp Gly Ile Val Gly Lys Asn Thr Trp Ala Glu
65                  70                  75                  80

Leu Phe Ser Lys Tyr Ser Pro Pro Ile Pro Tyr Lys Thr Ile Pro Met
                85                  90                  95

Pro Thr Ala Asn Lys Ser Arg Ala Ala Ala Thr Pro Val Met Asn Ala
            100                 105                 110

Val Glu Asn Ala Thr Gly Val Arg Ser Gln Leu Leu Leu Thr Phe Ala
        115                 120                 125

Ser Ile Glu Ser Ala Phe Asp Tyr Glu Ile Lys Ala Lys Thr Ser Ser
    130                 135                 140

Ala Thr Gly Trp Phe Gln Phe Leu Thr Gly Thr Trp Lys Thr Met Ile
145                 150                 155                 160

Glu Asn Tyr Gly Met Lys Tyr Gly Val Leu Thr Asp Pro Thr Gly Ala
                165                 170                 175

Leu Arg Lys Asp Pro Arg Ile Ser Ala Leu Met Gly Ala Glu Leu Ile
            180                 185                 190

Lys Glu Asn Met Asn Ile Leu Arg Pro Val Leu Lys Arg Glu Pro Thr
        195                 200                 205

Asp Thr Asp Leu Tyr Leu Ala His Phe Phe Gly Pro Gly Ala Ala Arg
    210                 215                 220

Arg Phe Leu Thr Thr Gly Gln Asn Glu Leu Ala Ala Thr His Phe Pro
225                 230                 235                 240

Lys Glu Ala Gln Ala Asn Pro Ser Ile Phe Tyr Asn Lys Asp Gly Ser
                245                 250                 255

Pro Lys Thr Ile Gln Glu Val Tyr Asn Leu Met Asp Gly Lys Val Ala
            260                 265                 270

Ala His Arg Lys
        275

<210> SEQ ID NO 38
<211> LENGTH: 281
<212> TYPE: PRT
<213> ORGANISM: unknown
<220> FEATURE:
<223> OTHER INFORMATION: Nigrocine2-KZ144

<400> SEQUENCE: 38

Gly Leu Leu Ser Lys Val Leu Gly Val Gly Lys Lys Val Leu Cys Gly
1               5                   10                  15

Val Ser Gly Leu Val Cys Lys Val Leu Arg Lys Gly Asp Arg Gly Asp
            20                  25                  30
```

Glu Val Cys Gln Leu Gln Thr Leu Leu Asn Leu Cys Gly Tyr Asp Val
 35                   40                  45

Gly Lys Pro Asp Gly Ile Phe Gly Asn Asn Thr Phe Asn Gln Val Val
 50                   55                  60

Lys Phe Gln Lys Asp Asn Cys Leu Asp Ser Asp Gly Ile Val Gly Lys
 65                   70              75                      80

Asn Thr Trp Ala Glu Leu Phe Ser Lys Tyr Ser Pro Ile Pro Tyr
                 85                  90                  95

Lys Thr Ile Pro Met Pro Thr Ala Asn Lys Ser Arg Ala Ala Ala Thr
             100                 105                 110

Pro Val Met Asn Ala Val Glu Asn Ala Thr Gly Val Arg Ser Gln Leu
             115                 120                 125

Leu Leu Thr Phe Ala Ser Ile Glu Ser Ala Phe Asp Tyr Glu Ile Lys
130                 135                 140

Ala Lys Thr Ser Ser Ala Thr Gly Trp Phe Gln Phe Leu Thr Gly Thr
145                 150                 155                 160

Trp Lys Thr Met Ile Glu Asn Tyr Gly Met Lys Tyr Gly Val Leu Thr
                 165                 170                 175

Asp Pro Thr Gly Ala Leu Arg Lys Asp Pro Arg Ile Ser Ala Leu Met
             180                 185                 190

Gly Ala Glu Leu Ile Lys Glu Asn Met Asn Ile Leu Arg Pro Val Leu
             195                 200                 205

Lys Arg Glu Pro Thr Asp Thr Asp Leu Tyr Leu Ala His Phe Gly
             210                 215                 220

Pro Gly Ala Ala Arg Arg Phe Leu Thr Thr Gly Gln Asn Glu Leu Ala
225                 230                 235                 240

Ala Thr His Phe Pro Lys Glu Ala Gln Ala Asn Pro Ser Ile Phe Tyr
                 245                 250                 255

Asn Lys Asp Gly Ser Pro Lys Thr Ile Gln Glu Val Tyr Asn Leu Met
             260                 265                 270

Asp Gly Lys Val Ala Ala His Arg Lys
             275                 280

<210> SEQ ID NO 39
<211> LENGTH: 283
<212> TYPE: PRT
<213> ORGANISM: unknown
<220> FEATURE:
<223> OTHER INFORMATION: Pseudin1-KZ144

<400> SEQUENCE: 39

Gly Leu Asn Thr Leu Lys Lys Val Phe Gln Gly Leu His Glu Ala Ile
1               5                   10                  15

Lys Leu Ile Asn Asn His Val Gln Lys Val Leu Arg Lys Gly Asp Arg
             20                  25                  30

Gly Asp Glu Val Cys Gln Leu Gln Thr Leu Leu Asn Leu Cys Gly Tyr
             35                  40                  45

Asp Val Gly Lys Pro Asp Gly Ile Phe Gly Asn Asn Thr Phe Asn Gln
         50                  55                  60

Val Val Lys Phe Gln Lys Asp Asn Cys Leu Asp Ser Asp Gly Ile Val
65                  70                  75                  80

Gly Lys Asn Thr Trp Ala Glu Leu Phe Ser Lys Tyr Ser Pro Pro Ile
                 85                  90                  95

Pro Tyr Lys Thr Ile Pro Met Pro Thr Ala Asn Lys Ser Arg Ala Ala
             100                 105                 110

```
Ala Thr Pro Val Met Asn Ala Val Glu Asn Ala Thr Gly Val Arg Ser
        115                 120                 125

Gln Leu Leu Leu Thr Phe Ala Ser Ile Glu Ser Ala Phe Asp Tyr Glu
    130                 135                 140

Ile Lys Ala Lys Thr Ser Ser Ala Thr Gly Trp Phe Gln Phe Leu Thr
145                 150                 155                 160

Gly Thr Trp Lys Thr Met Ile Glu Asn Tyr Gly Met Lys Tyr Gly Val
                    165                 170                 175

Leu Thr Asp Pro Thr Gly Ala Leu Arg Lys Asp Pro Arg Ile Ser Ala
            180                 185                 190

Leu Met Gly Ala Glu Leu Ile Lys Glu Asn Met Asn Ile Leu Arg Pro
        195                 200                 205

Val Leu Lys Arg Glu Pro Thr Asp Thr Asp Leu Tyr Leu Ala His Phe
    210                 215                 220

Phe Gly Pro Gly Ala Ala Arg Arg Phe Leu Thr Thr Gly Gln Asn Glu
225                 230                 235                 240

Leu Ala Ala Thr His Phe Pro Lys Glu Ala Gln Ala Asn Pro Ser Ile
                    245                 250                 255

Phe Tyr Asn Lys Asp Gly Ser Pro Lys Thr Ile Gln Glu Val Tyr Asn
            260                 265                 270

Leu Met Asp Gly Lys Val Ala Ala His Arg Lys
        275                 280

<210> SEQ ID NO 40
<211> LENGTH: 277
<212> TYPE: PRT
<213> ORGANISM: unknown
<220> FEATURE:
<223> OTHER INFORMATION: Ranalexin-KZ144

<400> SEQUENCE: 40

Phe Leu Gly Gly Leu Ile Val Pro Ala Met Ile Cys Ala Val Thr Lys
1               5                   10                  15

Lys Cys Lys Val Leu Arg Lys Gly Asp Arg Gly Asp Glu Val Cys Gln
                20                  25                  30

Leu Gln Thr Leu Leu Asn Leu Cys Gly Tyr Asp Val Gly Lys Pro Asp
            35                  40                  45

Gly Ile Phe Gly Asn Asn Thr Phe Asn Gln Val Val Lys Phe Gln Lys
        50                  55                  60

Asp Asn Cys Leu Asp Ser Asp Gly Ile Val Gly Lys Asn Thr Trp Ala
65                  70                  75                  80

Glu Leu Phe Ser Lys Tyr Ser Pro Pro Ile Pro Tyr Lys Thr Ile Pro
                85                  90                  95

Met Pro Thr Ala Asn Lys Ser Arg Ala Ala Thr Pro Val Met Asn
            100                 105                 110

Ala Val Glu Asn Ala Thr Gly Val Arg Ser Gln Leu Leu Leu Thr Phe
        115                 120                 125

Ala Ser Ile Glu Ser Ala Phe Asp Tyr Glu Ile Lys Ala Lys Thr Ser
    130                 135                 140

Ser Ala Thr Gly Trp Phe Gln Phe Leu Thr Gly Thr Trp Lys Thr Met
145                 150                 155                 160

Ile Glu Asn Tyr Gly Met Lys Tyr Gly Val Leu Thr Asp Pro Thr Gly
                165                 170                 175

Ala Leu Arg Lys Asp Pro Arg Ile Ser Ala Leu Met Gly Ala Glu Leu
            180                 185                 190
```

-continued

```
Ile Lys Glu Asn Met Asn Ile Leu Arg Pro Val Leu Lys Arg Glu Pro
        195                 200                 205

Thr Asp Thr Asp Leu Tyr Leu Ala His Phe Phe Gly Pro Gly Ala Ala
    210                 215                 220

Arg Arg Phe Leu Thr Thr Gly Gln Asn Glu Leu Ala Ala Thr His Phe
225                 230                 235                 240

Pro Lys Glu Ala Gln Ala Asn Pro Ser Ile Phe Tyr Asn Lys Asp Gly
                245                 250                 255

Ser Pro Lys Thr Ile Gln Glu Val Tyr Asn Leu Met Asp Gly Lys Val
            260                 265                 270

Ala Ala His Arg Lys
        275

<210> SEQ ID NO 41
<211> LENGTH: 286
<212> TYPE: PRT
<213> ORGANISM: unknown
<220> FEATURE:
<223> OTHER INFORMATION: WLBU2-Variant-KZ144

<400> SEQUENCE: 41

Lys Arg Trp Val Lys Arg Val Lys Arg Val Lys Arg Trp Val Lys Arg
1               5                   10                  15

Val Val Arg Val Val Lys Arg Trp Val Lys Arg Lys Val Leu Arg Lys
            20                  25                  30

Gly Asp Arg Gly Asp Glu Val Cys Gln Leu Gln Thr Leu Leu Asn Leu
        35                  40                  45

Cys Gly Tyr Asp Val Gly Lys Pro Asp Gly Ile Phe Gly Asn Asn Thr
    50                  55                  60

Phe Asn Gln Val Val Lys Phe Gln Lys Asp Asn Cys Leu Asp Ser Asp
65                  70                  75                  80

Gly Ile Val Gly Lys Asn Thr Trp Ala Glu Leu Phe Ser Lys Tyr Ser
                85                  90                  95

Pro Pro Ile Pro Tyr Lys Thr Ile Pro Met Pro Thr Ala Asn Lys Ser
            100                 105                 110

Arg Ala Ala Ala Thr Pro Val Met Asn Ala Val Glu Asn Ala Thr Gly
        115                 120                 125

Val Arg Ser Gln Leu Leu Leu Thr Phe Ala Ser Ile Glu Ser Ala Phe
    130                 135                 140

Asp Tyr Glu Ile Lys Ala Lys Thr Ser Ser Ala Thr Gly Trp Phe Gln
145                 150                 155                 160

Phe Leu Thr Gly Thr Trp Lys Thr Met Ile Glu Asn Tyr Gly Met Lys
                165                 170                 175

Tyr Gly Val Leu Thr Asp Pro Thr Gly Ala Leu Arg Lys Asp Pro Arg
            180                 185                 190

Ile Ser Ala Leu Met Gly Ala Glu Leu Ile Lys Glu Asn Met Asn Ile
        195                 200                 205

Leu Arg Pro Val Leu Lys Arg Glu Pro Thr Asp Thr Asp Leu Tyr Leu
    210                 215                 220

Ala His Phe Phe Gly Pro Gly Ala Ala Arg Arg Phe Leu Thr Thr Gly
225                 230                 235                 240

Gln Asn Glu Leu Ala Ala Thr His Phe Pro Lys Glu Ala Gln Ala Asn
                245                 250                 255

Pro Ser Ile Phe Tyr Asn Lys Asp Gly Ser Pro Lys Thr Ile Gln Glu
            260                 265                 270
```

Val Tyr Asn Leu Met Asp Gly Lys Val Ala Ala His Arg Lys
          275                 280                 285

<210> SEQ ID NO 42
<211> LENGTH: 293
<212> TYPE: PRT
<213> ORGANISM: unknown
<220> FEATURE:
<223> OTHER INFORMATION: Sushi1-KZ144

<400> SEQUENCE: 42

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser Lys Val Leu Arg Lys Gly Asp Arg Gly Asp Glu Val Cys Gln
        35                  40                  45

Leu Gln Thr Leu Leu Asn Leu Cys Gly Tyr Asp Val Gly Lys Pro Asp
    50                  55                  60

Gly Ile Phe Gly Asn Asn Thr Phe Asn Gln Val Val Lys Phe Gln Lys
65                  70                  75                  80

Asp Asn Cys Leu Asp Ser Asp Gly Ile Val Gly Lys Asn Thr Trp Ala
                85                  90                  95

Glu Leu Phe Ser Lys Tyr Ser Pro Pro Ile Pro Tyr Lys Thr Ile Pro
            100                 105                 110

Met Pro Thr Ala Asn Lys Ser Arg Ala Ala Ala Thr Pro Val Met Asn
        115                 120                 125

Ala Val Glu Asn Ala Thr Gly Val Arg Ser Gln Leu Leu Thr Phe
    130                 135                 140

Ala Ser Ile Glu Ser Ala Phe Asp Tyr Glu Ile Lys Ala Lys Thr Ser
145                 150                 155                 160

Ser Ala Thr Gly Trp Phe Gln Phe Leu Thr Gly Thr Trp Lys Thr Met
                165                 170                 175

Ile Glu Asn Tyr Gly Met Lys Tyr Gly Val Leu Thr Asp Pro Thr Gly
            180                 185                 190

Ala Leu Arg Lys Asp Pro Arg Ile Ser Ala Leu Met Gly Ala Glu Leu
        195                 200                 205

Ile Lys Glu Asn Met Asn Ile Leu Arg Pro Val Leu Lys Arg Glu Pro
    210                 215                 220

Thr Asp Thr Asp Leu Tyr Leu Ala His Phe Phe Gly Pro Gly Ala Ala
225                 230                 235                 240

Arg Arg Phe Leu Thr Thr Gly Gln Asn Glu Leu Ala Ala Thr His Phe
                245                 250                 255

Pro Lys Glu Ala Gln Ala Asn Pro Ser Ile Phe Tyr Asn Lys Asp Gly
            260                 265                 270

Ser Pro Lys Thr Ile Gln Glu Val Tyr Asn Leu Met Asp Gly Lys Val
        275                 280                 285

Ala Ala His Arg Lys
    290

<210> SEQ ID NO 43
<211> LENGTH: 285
<212> TYPE: PRT
<213> ORGANISM: unknown
<220> FEATURE:
<223> OTHER INFORMATION: Melttin-KZ144

<400> SEQUENCE: 43

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln Lys Val Leu Arg Lys Gly
            20                  25                  30

Asp Arg Gly Asp Glu Val Cys Gln Leu Gln Thr Leu Leu Asn Leu Cys
                35                  40                  45

Gly Tyr Asp Val Gly Lys Pro Asp Gly Ile Phe Gly Asn Asn Thr Phe
50                  55                  60

Asn Gln Val Val Lys Phe Gln Lys Asp Asn Cys Leu Asp Ser Asp Gly
65                  70                  75                  80

Ile Val Gly Lys Asn Thr Trp Ala Glu Leu Phe Ser Lys Tyr Ser Pro
                85                  90                  95

Pro Ile Pro Tyr Lys Thr Ile Pro Met Pro Thr Ala Asn Lys Ser Arg
                100                 105                 110

Ala Ala Ala Thr Pro Val Met Asn Ala Val Glu Asn Ala Thr Gly Val
                115                 120                 125

Arg Ser Gln Leu Leu Leu Thr Phe Ala Ser Ile Glu Ser Ala Phe Asp
130                 135                 140

Tyr Glu Ile Lys Ala Lys Thr Ser Ser Ala Thr Gly Trp Phe Gln Phe
145                 150                 155                 160

Leu Thr Gly Thr Trp Lys Thr Met Ile Glu Asn Tyr Gly Met Lys Tyr
                165                 170                 175

Gly Val Leu Thr Asp Pro Thr Gly Ala Leu Arg Lys Asp Pro Arg Ile
                180                 185                 190

Ser Ala Leu Met Gly Ala Glu Leu Ile Lys Glu Asn Met Asn Ile Leu
                195                 200                 205

Arg Pro Val Leu Lys Arg Glu Pro Thr Asp Thr Asp Leu Tyr Leu Ala
210                 215                 220

His Phe Phe Gly Pro Gly Ala Ala Arg Arg Phe Leu Thr Thr Gly Gln
225                 230                 235                 240

Asn Glu Leu Ala Ala Thr His Phe Pro Lys Glu Ala Gln Ala Asn Pro
                245                 250                 255

Ser Ile Phe Tyr Asn Lys Asp Gly Ser Pro Lys Thr Ile Gln Glu Val
                260                 265                 270

Tyr Asn Leu Met Asp Gly Lys Val Ala Ala His Arg Lys
275                 280                 285

<210> SEQ ID NO 44
<211> LENGTH: 296
<212> TYPE: PRT
<213> ORGANISM: unknown
<220> FEATURE:
<223> OTHER INFORMATION: LL-37-KZ144

<400> SEQUENCE: 44

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Lys Val Leu Arg Lys Gly Asp Arg Gly Asp Glu
                35                  40                  45

Val Cys Gln Leu Gln Thr Leu Leu Asn Leu Cys Gly Tyr Asp Val Gly
50                  55                  60

Lys Pro Asp Gly Ile Phe Gly Asn Asn Thr Phe Asn Gln Val Val Lys
65                  70                  75                  80
```

```
Phe Gln Lys Asp Asn Cys Leu Asp Ser Asp Gly Ile Val Gly Lys Asn
                85                  90                  95

Thr Trp Ala Glu Leu Phe Ser Lys Tyr Ser Pro Pro Ile Pro Tyr Lys
            100                 105                 110

Thr Ile Pro Met Pro Thr Ala Asn Lys Ser Arg Ala Ala Ala Thr Pro
        115                 120                 125

Val Met Asn Ala Val Glu Asn Ala Thr Gly Val Arg Ser Gln Leu Leu
    130                 135                 140

Leu Thr Phe Ala Ser Ile Glu Ser Ala Phe Asp Tyr Glu Ile Lys Ala
145                 150                 155                 160

Lys Thr Ser Ser Ala Thr Gly Trp Phe Gln Phe Leu Thr Gly Thr Trp
                165                 170                 175

Lys Thr Met Ile Glu Asn Tyr Gly Met Lys Tyr Gly Val Leu Thr Asp
            180                 185                 190

Pro Thr Gly Ala Leu Arg Lys Asp Pro Arg Ile Ser Ala Leu Met Gly
        195                 200                 205

Ala Glu Leu Ile Lys Glu Asn Met Asn Ile Leu Arg Pro Val Leu Lys
    210                 215                 220

Arg Glu Pro Thr Asp Thr Asp Leu Tyr Leu Ala His Phe Phe Gly Pro
225                 230                 235                 240

Gly Ala Ala Arg Arg Phe Leu Thr Thr Gly Gln Asn Glu Leu Ala Ala
                245                 250                 255

Thr His Phe Pro Lys Glu Ala Gln Ala Asn Pro Ser Ile Phe Tyr Asn
            260                 265                 270

Lys Asp Gly Ser Pro Lys Thr Ile Gln Glu Val Tyr Asn Leu Met Asp
        275                 280                 285

Gly Lys Val Ala Ala His Arg Lys
    290                 295

<210> SEQ ID NO 45
<211> LENGTH: 272
<212> TYPE: PRT
<213> ORGANISM: unknown
<220> FEATURE:
<223> OTHER INFORMATION: Indolicidin-KZ144

<400> SEQUENCE: 45

Ile Leu Pro Trp Lys Trp Pro Trp Trp Pro Trp Arg Arg Lys Val Leu
1               5                   10                  15

Arg Lys Gly Asp Arg Gly Asp Glu Val Cys Gln Leu Gln Thr Leu Leu
            20                  25                  30

Asn Leu Cys Gly Tyr Asp Val Gly Lys Pro Asp Gly Ile Phe Gly Asn
        35                  40                  45

Asn Thr Phe Asn Gln Val Val Lys Phe Gln Lys Asp Asn Cys Leu Asp
    50                  55                  60

Ser Asp Gly Ile Val Gly Lys Asn Thr Trp Ala Glu Leu Phe Ser Lys
65                  70                  75                  80

Tyr Ser Pro Pro Ile Pro Tyr Lys Thr Ile Pro Met Pro Thr Ala Asn
                85                  90                  95

Lys Ser Arg Ala Ala Ala Thr Pro Val Met Asn Ala Val Glu Asn Ala
            100                 105                 110

Thr Gly Val Arg Ser Gln Leu Leu Leu Thr Phe Ala Ser Ile Glu Ser
        115                 120                 125

Ala Phe Asp Tyr Glu Ile Lys Ala Lys Thr Ser Ser Ala Thr Gly Trp
    130                 135                 140
```

-continued

```
Phe Gln Phe Leu Thr Gly Thr Trp Lys Thr Met Ile Glu Asn Tyr Gly
145                 150                 155                 160

Met Lys Tyr Gly Val Leu Thr Asp Pro Thr Gly Ala Leu Arg Lys Asp
                165                 170                 175

Pro Arg Ile Ser Ala Leu Met Gly Ala Glu Leu Ile Lys Glu Asn Met
            180                 185                 190

Asn Ile Leu Arg Pro Val Leu Lys Arg Glu Pro Thr Asp Thr Asp Leu
        195                 200                 205

Tyr Leu Ala His Phe Phe Gly Pro Gly Ala Ala Arg Arg Phe Leu Thr
210                 215                 220

Thr Gly Gln Asn Glu Leu Ala Ala Thr His Phe Pro Lys Glu Ala Gln
225                 230                 235                 240

Ala Asn Pro Ser Ile Phe Tyr Asn Lys Asp Gly Ser Pro Lys Thr Ile
                245                 250                 255

Gln Glu Val Tyr Asn Leu Met Asp Gly Lys Val Ala Ala His Arg Lys
                260                 265                 270
```

<210> SEQ ID NO 46
<211> LENGTH: 288
<212> TYPE: PRT
<213> ORGANISM: unknown
<220> FEATURE:
<223> OTHER INFORMATION: SMAP-29-KZ144

<400> SEQUENCE: 46

```
Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Lys Val Leu
                20                  25                  30

Arg Lys Gly Asp Arg Gly Asp Glu Val Cys Gln Leu Gln Thr Leu Leu
            35                  40                  45

Asn Leu Cys Gly Tyr Asp Val Gly Lys Pro Asp Gly Ile Phe Gly Asn
        50                  55                  60

Asn Thr Phe Asn Gln Val Val Lys Phe Gln Lys Asp Asn Cys Leu Asp
65                  70                  75                  80

Ser Asp Gly Ile Val Gly Lys Asn Thr Trp Ala Glu Leu Phe Ser Lys
                85                  90                  95

Tyr Ser Pro Pro Ile Pro Tyr Lys Thr Ile Pro Met Pro Thr Ala Asn
                100                 105                 110

Lys Ser Arg Ala Ala Ala Thr Pro Val Met Asn Ala Val Glu Asn Ala
            115                 120                 125

Thr Gly Val Arg Ser Gln Leu Leu Leu Thr Phe Ala Ser Ile Glu Ser
130                 135                 140

Ala Phe Asp Tyr Glu Ile Lys Ala Lys Thr Ser Ser Ala Thr Gly Trp
145                 150                 155                 160

Phe Gln Phe Leu Thr Gly Thr Trp Lys Thr Met Ile Glu Asn Tyr Gly
                165                 170                 175

Met Lys Tyr Gly Val Leu Thr Asp Pro Thr Gly Ala Leu Arg Lys Asp
                180                 185                 190

Pro Arg Ile Ser Ala Leu Met Gly Ala Glu Leu Ile Lys Glu Asn Met
            195                 200                 205

Asn Ile Leu Arg Pro Val Leu Lys Arg Glu Pro Thr Asp Thr Asp Leu
        210                 215                 220

Tyr Leu Ala His Phe Phe Gly Pro Gly Ala Ala Arg Arg Phe Leu Thr
225                 230                 235                 240
```

Thr Gly Gln Asn Glu Leu Ala Ala Thr His Phe Pro Lys Glu Ala Gln
                245                 250                 255

Ala Asn Pro Ser Ile Phe Tyr Asn Lys Asp Gly Ser Pro Lys Thr Ile
            260                 265                 270

Gln Glu Val Tyr Asn Leu Met Asp Gly Lys Val Ala Ala His Arg Lys
        275                 280                 285

<210> SEQ ID NO 47
<211> LENGTH: 277
<212> TYPE: PRT
<213> ORGANISM: unknown
<220> FEATURE:
<223> OTHER INFORMATION: Protegrin-KZ144

<400> SEQUENCE: 47

Arg Gly Gly Arg Leu Cys Tyr Cys Arg Arg Phe Cys Val Cys Val
1               5                   10                  15

Gly Arg Lys Val Leu Arg Lys Gly Asp Arg Gly Asp Glu Val Cys Gln
            20                  25                  30

Leu Gln Thr Leu Leu Asn Leu Cys Gly Tyr Asp Val Gly Lys Pro Asp
        35                  40                  45

Gly Ile Phe Gly Asn Asn Thr Phe Asn Gln Val Val Lys Phe Gln Lys
    50                  55                  60

Asp Asn Cys Leu Asp Ser Asp Gly Ile Val Gly Lys Asn Thr Trp Ala
65                  70                  75                  80

Glu Leu Phe Ser Lys Tyr Ser Pro Pro Ile Pro Tyr Lys Thr Ile Pro
                85                  90                  95

Met Pro Thr Ala Asn Lys Ser Arg Ala Ala Thr Pro Val Met Asn
            100                 105                 110

Ala Val Glu Asn Ala Thr Gly Val Arg Ser Gln Leu Leu Leu Thr Phe
        115                 120                 125

Ala Ser Ile Glu Ser Ala Phe Asp Tyr Glu Ile Lys Ala Lys Thr Ser
    130                 135                 140

Ser Ala Thr Gly Trp Phe Gln Phe Leu Thr Gly Thr Trp Lys Thr Met
145                 150                 155                 160

Ile Glu Asn Tyr Gly Met Lys Tyr Gly Val Leu Thr Asp Pro Thr Gly
                165                 170                 175

Ala Leu Arg Lys Asp Pro Arg Ile Ser Ala Leu Met Gly Ala Glu Leu
            180                 185                 190

Ile Lys Glu Asn Met Asn Ile Leu Arg Pro Val Leu Lys Arg Glu Pro
        195                 200                 205

Thr Asp Thr Asp Leu Tyr Leu Ala His Phe Phe Gly Pro Gly Ala Ala
    210                 215                 220

Arg Arg Phe Leu Thr Thr Gly Gln Asn Glu Leu Ala Ala Thr His Phe
225                 230                 235                 240

Pro Lys Glu Ala Gln Ala Asn Pro Ser Ile Phe Tyr Asn Lys Asp Gly
                245                 250                 255

Ser Pro Lys Thr Ile Gln Glu Val Tyr Asn Leu Met Asp Gly Lys Val
            260                 265                 270

Ala Ala His Arg Lys
        275

<210> SEQ ID NO 48
<211> LENGTH: 290
<212> TYPE: PRT
<213> ORGANISM: unknown

<220> FEATURE:
<223> OTHER INFORMATION: Cecropin P1-KZ144

<400> SEQUENCE: 48

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg Lys
            20                  25                  30

Val Leu Arg Lys Gly Asp Arg Gly Asp Glu Val Cys Gln Leu Gln Thr
        35                  40                  45

Leu Leu Asn Leu Cys Gly Tyr Asp Val Gly Lys Pro Asp Gly Ile Phe
    50                  55                  60

Gly Asn Asn Thr Phe Asn Gln Val Val Lys Phe Gln Lys Asp Asn Cys
65                  70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Thr
            100                 105                 110

Ala Asn Lys Ser Arg Ala Ala Ala Thr Pro Val Met Asn Ala Val Glu
        115                 120                 125

Asn Ala Thr Gly Val Arg Ser Gln Leu Leu Leu Thr Phe Ala Ser Ile
130                 135                 140

Glu Ser Ala Phe Asp Tyr Glu Ile Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Ala Leu Arg
            180                 185                 190

Lys Asp Pro Arg Ile Ser Ala Leu Met Gly Ala Glu Leu Ile Lys Glu
        195                 200                 205

Asn Met Asn Ile Leu Arg Pro Val Leu Lys Arg Glu Pro Thr Asp Thr
210                 215                 220

Asp Leu Tyr Leu Ala His Phe Phe Gly Pro Gly Ala Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Ser Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys
    290

<210> SEQ ID NO 49
<211> LENGTH: 282
<212> TYPE: PRT
<213> ORGANISM: unknown
<220> FEATURE:
<223> OTHER INFORMATION: Magainin-KZ144

<400> SEQUENCE: 49

Gly Ile Gly Lys Phe Leu His Ser Ala Lys Lys Phe Gly Lys Ala Phe
1               5                   10                  15

Val Gly Glu Ile Met Asn Ser Lys Val Leu Arg Lys Gly Asp Arg Gly
            20                  25                  30

Asp Glu Val Cys Gln Leu Gln Thr Leu Leu Asn Leu Cys Gly Tyr Asp

```
            35                  40                  45
Val Gly Lys Pro Asp Gly Ile Phe Gly Asn Asn Thr Phe Asn Gln Val
 50                  55                  60

Val Lys Phe Gln Lys Asp Asn Cys Leu Asp Ser Asp Gly Ile Val Gly
 65                  70                  75                  80

Lys Asn Thr Trp Ala Glu Leu Phe Ser Lys Tyr Ser Pro Pro Ile Pro
                 85                  90                  95

Tyr Lys Thr Ile Pro Met Pro Thr Ala Asn Lys Ser Arg Ala Ala Ala
            100                 105                 110

Thr Pro Val Met Asn Ala Val Glu Asn Ala Thr Gly Val Arg Ser Gln
            115                 120                 125

Leu Leu Leu Thr Phe Ala Ser Ile Glu Ser Ala Phe Asp Tyr Glu Ile
130                 135                 140

Lys Ala Lys Thr Ser Ser Ala Thr Gly Trp Phe Gln Phe Leu Thr Gly
145                 150                 155                 160

Thr Trp Lys Thr Met Ile Glu Asn Tyr Gly Met Lys Tyr Gly Val Leu
                165                 170                 175

Thr Asp Pro Thr Gly Ala Leu Arg Lys Asp Pro Arg Ile Ser Ala Leu
            180                 185                 190

Met Gly Ala Glu Leu Ile Lys Glu Asn Met Asn Ile Leu Arg Pro Val
            195                 200                 205

Leu Lys Arg Glu Pro Thr Asp Thr Asp Leu Tyr Leu Ala His Phe Phe
210                 215                 220

Gly Pro Gly Ala Ala Arg Arg Phe Leu Thr Thr Gly Gln Asn Glu Leu
225                 230                 235                 240

Ala Ala Thr His Phe Pro Lys Glu Ala Gln Ala Asn Pro Ser Ile Phe
                245                 250                 255

Tyr Asn Lys Asp Gly Ser Pro Lys Thr Ile Gln Glu Val Tyr Asn Leu
            260                 265                 270

Met Asp Gly Lys Val Ala Ala His Arg Lys
            275                 280

<210> SEQ ID NO 50
<211> LENGTH: 284
<212> TYPE: PRT
<213> ORGANISM: unknown
<220> FEATURE:
<223> OTHER INFORMATION: Pleurocidin-KZ144

<400> SEQUENCE: 50

Gly Trp Gly Ser Phe Phe Lys Lys Ala Ala His Val Gly Lys His Val
 1               5                  10                  15

Gly Lys Ala Ala Leu Thr His Tyr Leu Lys Val Leu Arg Lys Gly Asp
                 20                  25                  30

Arg Gly Asp Glu Val Cys Gln Leu Gln Thr Leu Leu Asn Leu Cys Gly
            35                  40                  45

Tyr Asp Val Gly Lys Pro Asp Gly Ile Phe Gly Asn Asn Thr Phe Asn
 50                  55                  60

Gln Val Val Lys Phe Gln Lys Asp Asn Cys Leu Asp Ser Asp Gly Ile
 65                  70                  75                  80

Val Gly Lys Asn Thr Trp Ala Glu Leu Phe Ser Lys Tyr Ser Pro Pro
                 85                  90                  95

Ile Pro Tyr Lys Thr Ile Pro Met Pro Thr Ala Asn Lys Ser Arg Ala
            100                 105                 110

Ala Ala Thr Pro Val Met Asn Ala Val Glu Asn Ala Thr Gly Val Arg
```

```
            115                 120                 125
Ser Gln Leu Leu Leu Thr Phe Ala Ser Ile Glu Ser Ala Phe Asp Tyr
    130                 135                 140

Glu Ile Lys Ala Lys Thr Ser Ser Ala Thr Gly Trp Phe Gln Phe Leu
145                 150                 155                 160

Thr Gly Thr Trp Lys Thr Met Ile Glu Asn Tyr Gly Met Lys Tyr Gly
                165                 170                 175

Val Leu Thr Asp Pro Thr Gly Ala Leu Arg Lys Asp Pro Arg Ile Ser
            180                 185                 190

Ala Leu Met Gly Ala Glu Leu Ile Lys Glu Asn Met Asn Ile Leu Arg
        195                 200                 205

Pro Val Leu Lys Arg Glu Pro Thr Asp Thr Asp Leu Tyr Leu Ala His
    210                 215                 220

Phe Phe Gly Pro Gly Ala Ala Arg Arg Phe Leu Thr Thr Gly Gln Asn
225                 230                 235                 240

Glu Leu Ala Ala Thr His Phe Pro Lys Glu Ala Gln Ala Asn Pro Ser
                245                 250                 255

Ile Phe Tyr Asn Lys Asp Gly Ser Pro Lys Thr Ile Gln Glu Val Tyr
            260                 265                 270

Asn Leu Met Asp Gly Lys Val Ala Ala His Arg Lys
        275                 280

<210> SEQ ID NO 51
<211> LENGTH: 295
<212> TYPE: PRT
<213> ORGANISM: unknown
<220> FEATURE:
<223> OTHER INFORMATION: Cecropin A (A.aegypti)-KZ144

<400> SEQUENCE: 51

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys Lys Val Leu Arg Lys Gly Asp Arg Gly Asp Glu Val
        35                  40                  45

Cys Gln Leu Gln Thr Leu Leu Asn Leu Cys Gly Tyr Asp Val Gly Lys
    50                  55                  60

Pro Asp Gly Ile Phe Gly Asn Asn Thr Phe Asn Gln Val Val Lys Phe
65                  70                  75                  80

Gln Lys Asp Asn Cys Leu Asp Ser Asp Gly Ile Val Gly Lys Asn Thr
                85                  90                  95

Trp Ala Glu Leu Phe Ser Lys Tyr Ser Pro Pro Ile Pro Tyr Lys Thr
            100                 105                 110

Ile Pro Met Pro Thr Ala Asn Lys Ser Arg Ala Ala Ala Thr Pro Val
        115                 120                 125

Met Asn Ala Val Glu Asn Ala Thr Gly Val Arg Ser Gln Leu Leu Leu
    130                 135                 140

Thr Phe Ala Ser Ile Glu Ser Ala Phe Asp Tyr Glu Ile Lys Ala Lys
145                 150                 155                 160

Thr Ser Ser Ala Thr Gly Trp Phe Gln Phe Leu Thr Thr Trp Lys
                165                 170                 175

Thr Met Ile Glu Asn Tyr Gly Met Lys Tyr Gly Val Leu Thr Asp Pro
            180                 185                 190

Thr Gly Ala Leu Arg Lys Asp Pro Arg Ile Ser Ala Leu Met Gly Ala
```

```
                195                 200                 205
Glu Leu Ile Lys Glu Asn Met Asn Ile Leu Arg Pro Val Lys Arg
210                 215                 220

Glu Pro Thr Asp Thr Asp Leu Tyr Leu Ala His Phe Gly Pro Gly
225                 230                 235                 240

Ala Ala Arg Arg Phe Leu Thr Thr Gly Gln Asn Glu Leu Ala Thr
                245                 250                 255

His Phe Pro Lys Glu Ala Gln Ala Asn Pro Ser Ile Phe Tyr Asn Lys
                260                 265                 270

Asp Gly Ser Pro Lys Thr Ile Gln Glu Val Tyr Asn Leu Met Asp Gly
                275                 280                 285

Lys Val Ala Ala His Arg Lys
                290                 295

<210> SEQ ID NO 52
<211> LENGTH: 299
<212> TYPE: PRT
<213> ORGANISM: unknown
<220> FEATURE:
<223> OTHER INFORMATION: Cecropin A (D.melanogaster)-KZ144

<400> SEQUENCE: 52

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
                20                  25                  30

Asn Val Ala Ala Thr Ala Arg Gly Lys Val Leu Arg Lys Gly Asp Arg
                35                  40                  45

Gly Asp Glu Val Cys Gln Leu Gln Thr Leu Leu Asn Leu Cys Gly Tyr
50                  55                  60

Asp Val Gly Lys Pro Asp Gly Ile Phe Gly Asn Asn Thr Phe Asn Gln
65                  70                  75                  80

Val Val Lys Phe Gln Lys Asp Asn Cys Leu Asp Ser Asp Gly Ile Val
                85                  90                  95

Gly Lys Asn Thr Trp Ala Glu Leu Phe Ser Lys Tyr Ser Pro Pro Ile
                100                 105                 110

Pro Tyr Lys Thr Ile Pro Met Pro Thr Ala Asn Lys Ser Arg Ala Ala
                115                 120                 125

Ala Thr Pro Val Met Asn Ala Val Glu Asn Ala Thr Gly Val Arg Ser
                130                 135                 140

Gln Leu Leu Leu Thr Phe Ala Ser Ile Glu Ser Ala Phe Asp Tyr Glu
145                 150                 155                 160

Ile Lys Ala Lys Thr Ser Ser Ala Thr Gly Trp Phe Gln Phe Leu Thr
                165                 170                 175

Gly Thr Trp Lys Thr Met Ile Glu Asn Tyr Gly Met Lys Tyr Gly Val
                180                 185                 190

Leu Thr Asp Pro Thr Gly Ala Leu Arg Lys Asp Pro Arg Ile Ser Ala
                195                 200                 205

Leu Met Gly Ala Glu Leu Ile Lys Glu Asn Met Asn Ile Leu Arg Pro
210                 215                 220

Val Leu Lys Arg Glu Pro Thr Asp Thr Asp Leu Tyr Leu Ala His Phe
225                 230                 235                 240

Phe Gly Pro Gly Ala Ala Arg Arg Phe Leu Thr Thr Gly Gln Asn Glu
                245                 250                 255

Leu Ala Ala Thr His Phe Pro Lys Glu Ala Gln Ala Asn Pro Ser Ile
```

```
                260             265              270
Phe Tyr Asn Lys Asp Gly Ser Pro Lys Thr Ile Gln Glu Val Tyr Asn
        275                 280                 285

Leu Met Asp Gly Lys Val Ala Ala His Arg Lys
        290                 295

<210> SEQ ID NO 53
<211> LENGTH: 280
<212> TYPE: PRT
<213> ORGANISM: unknown
<220> FEATURE:
<223> OTHER INFORMATION: BuforinII-KZ144

<400> SEQUENCE: 53

Thr Arg Ser Ser Arg Ala Gly Leu Gln Phe Pro Val Gly Arg Val His
1               5                   10                  15

Arg Leu Leu Arg Lys Val Leu Arg Lys Gly Asp Arg Gly Asp Val Glu
            20                  25                  30

Val Cys Gln Leu Gln Thr Leu Leu Asn Leu Cys Gly Tyr Asp Val Gly
        35                  40                  45

Lys Pro Asp Gly Ile Phe Gly Asn Asn Thr Phe Asn Gln Val Val Lys
    50                  55                  60

Phe Gln Lys Asp Asn Cys Leu Asp Ser Asp Gly Ile Val Gly Lys Asn
65                  70                  75                  80

Thr Trp Ala Glu Leu Phe Ser Lys Tyr Ser Pro Ile Pro Tyr Lys
                85                  90                  95

Thr Ile Pro Met Pro Thr Ala Asn Lys Ser Arg Ala Ala Ala Thr Pro
            100                 105                 110

Val Met Asn Ala Val Glu Asn Ala Thr Gly Val Arg Ser Gln Leu Leu
        115                 120                 125

Leu Thr Phe Ala Ser Ile Glu Ser Ala Phe Asp Tyr Glu Ile Lys Ala
    130                 135                 140

Lys Thr Ser Ser Ala Thr Gly Trp Phe Gln Phe Leu Thr Gly Thr Trp
145                 150                 155                 160

Lys Thr Met Ile Glu Asn Tyr Gly Met Lys Tyr Gly Val Leu Thr Asp
                165                 170                 175

Pro Thr Gly Ala Leu Arg Lys Asp Pro Arg Ile Ser Ala Leu Met Gly
            180                 185                 190

Ala Glu Leu Ile Lys Glu Asn Met Asn Ile Leu Arg Pro Val Leu Lys
        195                 200                 205

Arg Glu Pro Thr Asp Thr Asp Leu Tyr Leu Ala His Phe Phe Gly Pro
    210                 215                 220

Gly Ala Ala Arg Arg Phe Leu Thr Thr Gly Gln Asn Glu Leu Ala Ala
225                 230                 235                 240

Thr His Phe Pro Lys Glu Ala Gln Ala Asn Pro Ser Ile Phe Tyr Asn
                245                 250                 255

Lys Asp Gly Ser Pro Lys Thr Ile Gln Glu Val Tyr Asn Leu Met Asp
            260                 265                 270

Gly Lys Val Ala Ala His Arg Lys
        275                 280

<210> SEQ ID NO 54
<211> LENGTH: 298
<212> TYPE: PRT
<213> ORGANISM: unknown
<220> FEATURE:
<223> OTHER INFORMATION: Sarcotoxin IA-KZ144
```

<400> SEQUENCE: 54

```
Gly Trp Leu Lys Lys Ile Gly Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg Lys Val Leu Arg Lys Gly Asp Arg Gly
                35                  40                  45

Asp Glu Val Cys Gln Leu Gln Thr Leu Leu Asn Leu Cys Gly Tyr Asp
    50                  55                  60

Val Gly Lys Pro Asp Gly Ile Phe Gly Asn Asn Thr Phe Asn Gln Val
65                  70                  75                  80

Val Lys Phe Gln Lys Asp Asn Cys Leu Asp Ser Asp Gly Ile Val Gly
                85                  90                  95

Lys Asn Thr Trp Ala Glu Leu Phe Ser Lys Tyr Ser Pro Pro Ile Pro
                100                 105                 110

Tyr Lys Thr Ile Pro Met Pro Thr Ala Asn Lys Ser Arg Ala Ala Ala
                115                 120                 125

Thr Pro Val Met Asn Ala Val Glu Asn Ala Thr Gly Val Arg Ser Gln
130                 135                 140

Leu Leu Leu Thr Phe Ala Ser Ile Glu Ser Ala Phe Asp Tyr Glu Ile
145                 150                 155                 160

Lys Ala Lys Thr Ser Ser Ala Thr Gly Trp Phe Gln Phe Leu Thr Gly
                165                 170                 175

Thr Trp Lys Thr Met Ile Glu Asn Tyr Gly Met Lys Tyr Gly Val Leu
                180                 185                 190

Thr Asp Pro Thr Gly Ala Leu Arg Lys Asp Pro Arg Ile Ser Ala Leu
                195                 200                 205

Met Gly Ala Glu Leu Ile Lys Glu Asn Met Asn Ile Leu Arg Pro Val
            210                 215                 220

Leu Lys Arg Glu Pro Thr Asp Thr Asp Leu Tyr Leu Ala His Phe Phe
225                 230                 235                 240

Gly Pro Gly Ala Ala Arg Arg Phe Leu Thr Thr Gly Gln Asn Glu Leu
                245                 250                 255

Ala Ala Thr His Phe Pro Lys Glu Ala Gln Ala Asn Pro Ser Ile Phe
                260                 265                 270

Tyr Asn Lys Asp Gly Ser Pro Lys Thr Ile Gln Glu Val Tyr Asn Leu
                275                 280                 285

Met Asp Gly Lys Val Ala Ala His Arg Lys
    290                 295
```

<210> SEQ ID NO 55
<211> LENGTH: 200
<212> TYPE: PRT
<213> ORGANISM: unknown
<220> FEATURE:
<223> OTHER INFORMATION: Ascaphine 5-STM0016

<400> SEQUENCE: 55

```
Gly Ile Lys Asp Trp Ile Lys Gly Ala Ala Lys Lys Leu Ile Lys Thr
1               5                   10                  15

Val Ala Ser His Ile Ala Asn Gln Asn Pro Ile Ile Asp Gly Ile Ile
            20                  25                  30

Ala Leu Glu Gly Gly Tyr Val Phe Asn Pro Lys Asp Lys Gly Gly Ala
                35                  40                  45
```

Thr His Trp Gly Ile Thr Glu Ala Thr Ala Arg Ala His Gly Tyr Ala
 50                  55                  60

Gly Asp Met Arg Asp Leu Thr His Ala Glu Ala Tyr Ala Ile Leu Glu
 65                  70                  75                  80

Glu Asp Tyr Trp Ile Lys Pro Gly Phe Asp Val Ile Ser Thr Leu Ser
                 85                  90                  95

Trp Pro Val Ser Phe Glu Leu Cys Asp Ala Ala Val Asn Ile Gly Ala
                100                 105                 110

Tyr His Pro Ser Ala Trp Leu Gln Arg Trp Leu Asn Val Phe Asn His
            115                 120                 125

Glu Gly Lys Arg Tyr Pro Asp Ile His Val Asp Gly Asn Ile Gly Pro
130                 135                 140

Arg Thr Leu Ala Ala Leu Glu His Tyr Leu Ala Trp Arg Gly Gln Glu
145                 150                 155                 160

Gly Glu Ala Val Leu Val Lys Ala Leu Asn Cys Ser Gln Gly Thr Tyr
                165                 170                 175

Tyr Leu Asn Val Ala Glu Lys Asn His Asn Asn Glu Gln Phe Ile Tyr
            180                 185                 190

Gly Trp Ile Lys Asn Arg Val Thr
        195                 200

<210> SEQ ID NO 56
<211> LENGTH: 198
<212> TYPE: PRT
<213> ORGANISM: unknown
<220> FEATURE:
<223> OTHER INFORMATION: Nigrocine2-STM0016

<400> SEQUENCE: 56

Gly Leu Leu Ser Lys Val Leu Gly Val Gly Lys Lys Val Leu Cys Gly
1               5                   10                  15

Val Ser Gly Leu Val Cys Asn Pro Ile Ile Asp Gly Ile Ile Ala Leu
            20                  25                  30

Glu Gly Gly Tyr Val Phe Asn Pro Lys Asp Lys Gly Ala Thr His
        35                  40                  45

Trp Gly Ile Thr Glu Ala Thr Ala Arg Ala His Gly Tyr Ala Gly Asp
 50                  55                  60

Met Arg Asp Leu Thr His Ala Glu Ala Tyr Ala Ile Leu Glu Glu Asp
 65                  70                  75                  80

Tyr Trp Ile Lys Pro Gly Phe Asp Val Ile Ser Thr Leu Ser Trp Pro
                85                  90                  95

Val Ser Phe Glu Leu Cys Asp Ala Ala Val Asn Ile Gly Ala Tyr His
            100                 105                 110

Pro Ser Ala Trp Leu Gln Arg Trp Leu Asn Val Phe Asn His Glu Gly
        115                 120                 125

Lys Arg Tyr Pro Asp Ile His Val Asp Gly Asn Ile Gly Pro Arg Thr
130                 135                 140

Leu Ala Ala Leu Glu His Tyr Leu Ala Trp Arg Gly Gln Glu Gly Glu
145                 150                 155                 160

Ala Val Leu Val Lys Ala Leu Asn Cys Ser Gln Gly Thr Tyr Tyr Leu
                165                 170                 175

Asn Val Ala Glu Lys Asn His Asn Asn Glu Gln Phe Ile Tyr Gly Trp
            180                 185                 190

Ile Lys Asn Arg Val Thr
        195

<210> SEQ ID NO 57
<211> LENGTH: 205
<212> TYPE: PRT
<213> ORGANISM: unknown
<220> FEATURE:
<223> OTHER INFORMATION: SMAP-29-STM0016

<400> SEQUENCE: 57

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Asn Pro Ile
            20                  25                  30

Ile Asp Gly Ile Ile Ala Leu Glu Gly Gly Tyr Val Phe Asn Pro Lys
        35                  40                  45

Asp Lys Gly Gly Ala Thr His Trp Gly Ile Thr Glu Ala Thr Ala Arg
    50                  55                  60

Ala His Gly Tyr Ala Gly Asp Met Arg Asp Leu Thr His Ala Glu Ala
65                  70                  75                  80

Tyr Ala Ile Leu Glu Glu Asp Tyr Trp Ile Lys Pro Gly Phe Asp Val
                85                  90                  95

Ile Ser Thr Leu Ser Trp Pro Val Ser Phe Glu Leu Cys Asp Ala Ala
            100                 105                 110

Val Asn Ile Gly Ala Tyr His Pro Ser Ala Trp Leu Gln Arg Trp Leu
        115                 120                 125

Asn Val Phe Asn His Glu Gly Lys Arg Tyr Pro Asp Ile His Val Asp
    130                 135                 140

Gly Asn Ile Gly Pro Arg Thr Leu Ala Ala Leu Glu His Tyr Leu Ala
145                 150                 155                 160

Trp Arg Gly Gln Glu Gly Glu Ala Val Leu Val Lys Ala Leu Asn Cys
                165                 170                 175

Ser Gln Gly Thr Tyr Tyr Leu Asn Val Ala Glu Lys Asn His Asn Asn
            180                 185                 190

Glu Gln Phe Ile Tyr Gly Trp Ile Lys Asn Arg Val Thr
        195                 200                 205

<210> SEQ ID NO 58
<211> LENGTH: 215
<212> TYPE: PRT
<213> ORGANISM: unknown
<220> FEATURE:
<223> OTHER INFORMATION: Sarcotoxin IA-STM0016

<400> SEQUENCE: 58

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg Asn Pro Ile Ile Asp Gly Ile Ile Ala
        35                  40                  45

Leu Glu Gly Gly Tyr Val Phe Asn Pro Lys Asp Lys Gly Gly Ala Thr
    50                  55                  60

His Trp Gly Ile Thr Glu Ala Thr Ala Arg Ala His Gly Tyr Ala Gly
65                  70                  75                  80

Asp Met Arg Asp Leu Thr His Ala Glu Ala Tyr Ala Ile Leu Glu Glu
                85                  90                  95

Asp Tyr Trp Ile Lys Pro Gly Phe Asp Val Ile Ser Thr Leu Ser Trp
            100                 105                 110

```
Pro Val Ser Phe Glu Leu Cys Asp Ala Val Asn Ile Gly Ala Tyr
        115                 120                 125

His Pro Ser Ala Trp Leu Gln Arg Trp Leu Asn Val Phe Asn His Glu
    130                 135                 140

Gly Lys Arg Tyr Pro Asp Ile His Val Asp Gly Asn Ile Gly Pro Arg
145                 150                 155                 160

Thr Leu Ala Ala Leu Glu His Tyr Leu Ala Trp Arg Gly Gln Glu Gly
                165                 170                 175

Glu Ala Val Leu Val Lys Ala Leu Asn Cys Ser Gln Gly Thr Tyr Tyr
            180                 185                 190

Leu Asn Val Ala Glu Lys Asn His Asn Asn Glu Gln Phe Ile Tyr Gly
        195                 200                 205

Trp Ile Lys Asn Arg Val Thr
        210                 215

<210> SEQ ID NO 59
<211> LENGTH: 233
<212> TYPE: PRT
<213> ORGANISM: unknown
<220> FEATURE:
<223> OTHER INFORMATION: Melittin-N4gp61

<400> SEQUENCE: 59

Gly Ile Gly Ala Val Leu Lys Val Leu Thr Thr Gly Leu Pro Ala Leu
1               5                   10                  15

Ile Ser Trp Ile Lys Arg Lys Arg Gln Gln Ala Ile Ser Lys Lys Lys
            20                  25                  30

Val Gly Gly Val Gly Gly Val Ile Ala Ala Ile Ile Ala Ala Val Phe
        35                  40                  45

Ala Val Glu Gly Gly Tyr Val Asn Asp Pro Lys Asp Pro Gly Gly Glu
    50                  55                  60

Thr Asn His Gly Val Thr Ile Gln Val Ala Gln Lys His Lys Gln Glu
65                  70                  75                  80

Leu Glu Ser Met Tyr Asn Trp Asp Gly Ser Met Lys Asn Leu Thr Gln
                85                  90                  95

Glu Met Ala Ser Ser Ile Tyr Tyr Asn Asp Tyr Ile Leu Lys Pro Gly
            100                 105                 110

Phe Val Lys Phe Ala Asp Val Ser Pro Ala Val Thr Glu Lys Leu Val
        115                 120                 125

Asp Ala Gly Val Asn Thr Gly Pro Ala Arg Pro Ser Arg Trp Leu Gln
    130                 135                 140

Glu Ser Leu Asn Ala Phe Ser Arg Asn Gly Lys Asp Tyr Pro Lys Ile
145                 150                 155                 160

Gln Val Asp Gly Lys Val Gly Ser Gly Thr Leu Ser Ala Tyr Lys Ser
                165                 170                 175

Leu Gln Asn Lys Arg Gly Lys Val Glu Ala Cys Lys Leu Ile Leu Lys
            180                 185                 190

Ser Leu Asp Gly Lys Gln Leu Asn Tyr Tyr Leu Ser Leu Asn Met Pro
        195                 200                 205

Glu Tyr Thr Thr Gly Trp Ile Ala Asn Arg Ile Gly Asn Val Pro Leu
    210                 215                 220

Glu Arg Cys Asn Glu Asp Ile Val Asn
225                 230

<210> SEQ ID NO 60
```

<211> LENGTH: 236
<212> TYPE: PRT
<213> ORGANISM: unknown
<220> FEATURE:
<223> OTHER INFORMATION: SMAP-29-N4gp61

<400> SEQUENCE: 60

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Ala Ile Ser
            20                  25                  30

Lys Lys Lys Val Gly Val Gly Val Ile Ala Ala Ile Ile Ala
        35                  40                  45

Ala Val Phe Ala Val Glu Gly Gly Tyr Val Asn Asp Pro Lys Asp Pro
50                  55                  60

Gly Gly Glu Thr Asn His Gly Val Thr Ile Gln Val Ala Gln Lys His
65                  70                  75                  80

Lys Gln Glu Leu Glu Ser Met Tyr Asn Trp Asp Gly Ser Met Lys Asn
                85                  90                  95

Leu Thr Gln Glu Met Ala Ser Ser Ile Tyr Tyr Asn Asp Tyr Ile Leu
            100                 105                 110

Lys Pro Gly Phe Val Lys Phe Ala Asp Val Ser Pro Ala Val Thr Glu
        115                 120                 125

Lys Leu Val Asp Ala Gly Val Asn Thr Gly Pro Ala Arg Pro Ser Arg
130                 135                 140

Trp Leu Gln Glu Ser Leu Asn Ala Phe Ser Arg Asn Gly Lys Asp Tyr
145                 150                 155                 160

Pro Lys Ile Gln Val Asp Gly Lys Val Gly Ser Gly Thr Leu Ser Ala
                165                 170                 175

Tyr Lys Ser Leu Gln Asn Lys Arg Gly Lys Val Glu Ala Cys Lys Leu
            180                 185                 190

Ile Leu Lys Ser Leu Asp Gly Lys Gln Leu Asn Tyr Tyr Leu Ser Leu
        195                 200                 205

Asn Met Pro Glu Tyr Thr Thr Gly Trp Ile Ala Asn Arg Ile Gly Asn
210                 215                 220

Val Pro Leu Glu Arg Cys Asn Glu Asp Ile Val Asn
225                 230                 235

<210> SEQ ID NO 61
<211> LENGTH: 210
<212> TYPE: PRT
<213> ORGANISM: unknown
<220> FEATURE:
<223> OTHER INFORMATION: Melittin-N4gp61trunc

<400> SEQUENCE: 61

Gly Ile Gly Ala Val Leu Lys Val Leu Thr Thr Gly Leu Pro Ala Leu
1               5                   10                  15

Ile Ser Trp Ile Lys Arg Lys Arg Gln Gln Val Glu Gly Gly Tyr Val
            20                  25                  30

Asn Asp Pro Lys Asp Pro Gly Gly Glu Thr Asn His Gly Val Thr Ile
        35                  40                  45

Gln Val Ala Gln Lys His Lys Gln Glu Leu Glu Ser Met Tyr Asn Trp
50                  55                  60

Asp Gly Ser Met Lys Asn Leu Thr Gln Glu Met Ala Ser Ser Ile Tyr
65                  70                  75                  80

Tyr Asn Asp Tyr Ile Leu Lys Pro Gly Phe Val Lys Phe Ala Asp Val

```
            85                  90                  95
Ser Pro Ala Val Thr Glu Lys Leu Val Asp Ala Gly Val Asn Thr Gly
            100                 105                 110

Pro Ala Arg Pro Ser Arg Trp Leu Gln Glu Ser Leu Asn Ala Phe Ser
            115                 120                 125

Arg Asn Gly Lys Asp Tyr Pro Lys Ile Gln Val Asp Gly Lys Val Gly
            130                 135                 140

Ser Gly Thr Leu Ser Ala Tyr Lys Ser Leu Gln Asn Lys Arg Gly Lys
145                 150                 155                 160

Val Glu Ala Cys Lys Leu Ile Leu Lys Ser Leu Asp Gly Lys Gln Leu
                    165                 170                 175

Asn Tyr Tyr Leu Ser Leu Asn Met Pro Glu Tyr Thr Thr Gly Trp Ile
                    180                 185                 190

Ala Asn Arg Ile Gly Asn Val Pro Leu Glu Arg Cys Asn Glu Asp Ile
                    195                 200                 205

Val Asn
    210
```

<210> SEQ ID NO 62
<211> LENGTH: 215
<212> TYPE: PRT
<213> ORGANISM: unknown
<220> FEATURE:
<223> OTHER INFORMATION: Cecropin P1-N4gp61trunc

<400> SEQUENCE: 62

```
Ser Trp Leu Ser Lys Thr Ala Lys Leu Glu Asn Ser Ala Lys Lys
1               5                   10                  15

Arg Ile Ser Glu Gly Ile Ala Ile Ala Ile Gln Gly Gly Pro Arg Val
                20                  25                  30

Glu Gly Gly Tyr Val Asn Asp Pro Lys Asp Pro Gly Gly Glu Thr Asn
                35                  40                  45

His Gly Val Thr Ile Gln Val Ala Gln Lys His Lys Gln Glu Leu Glu
            50                  55                  60

Ser Met Tyr Asn Trp Asp Gly Ser Met Lys Asn Leu Thr Gln Glu Met
65                  70                  75                  80

Ala Ser Ser Ile Tyr Tyr Asn Asp Tyr Ile Leu Lys Pro Gly Phe Val
                    85                  90                  95

Lys Phe Ala Asp Val Ser Pro Ala Val Thr Glu Lys Leu Val Asp Ala
            100                 105                 110

Gly Val Asn Thr Gly Pro Ala Arg Pro Ser Arg Trp Leu Gln Glu Ser
            115                 120                 125

Leu Asn Ala Phe Ser Arg Asn Gly Lys Asp Tyr Pro Lys Ile Gln Val
130                 135                 140

Asp Gly Lys Val Gly Ser Gly Thr Leu Ser Ala Tyr Lys Ser Leu Gln
145                 150                 155                 160

Asn Lys Arg Gly Lys Val Glu Ala Cys Lys Leu Ile Leu Lys Ser Leu
                165                 170                 175

Asp Gly Lys Gln Leu Asn Tyr Tyr Leu Ser Leu Asn Met Pro Glu Tyr
                180                 185                 190

Thr Thr Gly Trp Ile Ala Asn Arg Ile Gly Asn Val Pro Leu Glu Arg
                195                 200                 205

Cys Asn Glu Asp Ile Val Asn
210                 215
```

<210> SEQ ID NO 63
<211> LENGTH: 213
<212> TYPE: PRT
<213> ORGANISM: unknown
<220> FEATURE:
<223> OTHER INFORMATION: SMAP-29-N4gp61trunc

<400> SEQUENCE: 63

```
Arg Gly Leu Arg Arg Leu Gly Arg Lys Ile Ala His Gly Val Lys Lys
1               5                   10                  15
Tyr Gly Pro Thr Val Leu Arg Ile Ile Arg Ile Ala Gly Val Glu Gly
            20                  25                  30
Gly Tyr Val Asn Asp Pro Lys Asp Pro Gly Gly Glu Thr Asn His Gly
        35                  40                  45
Val Thr Ile Gln Val Ala Gln Lys His Lys Gln Glu Leu Glu Ser Met
    50                  55                  60
Tyr Asn Trp Asp Gly Ser Met Lys Asn Leu Thr Gln Glu Met Ala Ser
65                  70                  75                  80
Ser Ile Tyr Tyr Asn Asp Tyr Ile Leu Lys Pro Gly Phe Val Lys Phe
                85                  90                  95
Ala Asp Val Ser Pro Ala Val Thr Glu Lys Leu Val Asp Ala Gly Val
            100                 105                 110
Asn Thr Gly Pro Ala Arg Pro Ser Arg Trp Leu Gln Glu Ser Leu Asn
        115                 120                 125
Ala Phe Ser Arg Asn Gly Lys Asp Tyr Pro Lys Ile Gln Val Asp Gly
    130                 135                 140
Lys Val Gly Ser Gly Thr Leu Ser Ala Tyr Lys Ser Leu Gln Asn Lys
145                 150                 155                 160
Arg Gly Lys Val Glu Ala Cys Lys Leu Ile Leu Lys Ser Leu Asp Gly
                165                 170                 175
Lys Gln Leu Asn Tyr Tyr Leu Ser Leu Asn Met Pro Glu Tyr Thr Thr
            180                 185                 190
Gly Trp Ile Ala Asn Arg Ile Gly Asn Val Pro Leu Glu Arg Cys Asn
        195                 200                 205
Glu Asp Ile Val Asn
    210
```

<210> SEQ ID NO 64
<211> LENGTH: 777
<212> TYPE: DNA
<213> ORGANISM: unknown
<220> FEATURE:
<223> OTHER INFORMATION: KZ144

<400> SEQUENCE: 64

```
aaagtattac gcaaaggcga tagggggtgat gaggtatgtc aactccagac actcttaaat      60
ttatgtggct atgatgttgg aaagccagat ggtattttg gaaataacac ctttaatcag       120
gtagttaaat ttcaaaaaga taattgtcta gatagtgatg gtattgtagg taagaatact      180
tgggctgaat tattcagtaa atattctcca cctattcctt ataaaactat ccctatgcca      240
actgcaaata atcacgtgc agctgcaact ccagttatga atgcagtaga aaatgctact       300
ggcgttcgta gccagttgct actaacattt gcttctattg aatcagcatt cgattacgaa      360
ataaaagcta agacttcatc agctactggt tggttccaat tccttactgg aacatggaaa      420
acaatgattg aaaattatgg catgaagtat ggcgtactta ctgatccaac tggggcatta      480
cgtaaagatc cacgtataag tgctttaatg ggtgccgaac taattaaaga gaatatgaat      540
```

```
attcttcgtc ctgtccttaa acgtgaacca actgatactg atctttATTt agctcacttc    600
tttgggcctg gtgcagcccg tcgtttcctg accactggcc agaatgaatt agctgctacc    660
catttcccaa aagaagctca ggcaaaccca tctattttTT ataacaaaga tgggtcacct    720
aaaaccattc aagaagttta aacttaatg gatggtaaag ttgcagcaca tagaaaa       777

<210> SEQ ID NO 65
<211> LENGTH: 528
<212> TYPE: DNA
<213> ORGANISM: unknown
<220> FEATURE:
<223> OTHER INFORMATION: STM0016

<400> SEQUENCE: 65
aacccgatta tcgatggcat tatcgcgctg gaaggaggtt acgtctttaa tccgaaagat     60
aagggtggag caacacattg gggtattaca gaagcgacgg cacgagcaca tggttatgca    120
ggagacatgc gtgatctaac tcatgccgaa gcctacgcaa tacttgagga ggattactgg    180
atcaaaccgg gttttgatgt tatctcaacg ctgtcgtggc ctgtgagctt tgaattgtgt    240
gatgcagcgg ttaacatagg tgcataccac cctagtgcct ggttacagag atggcttaac    300
gtgttcaatc acgaaggcaa acgctatcca gacattcatg tagacggcaa cattggtccc    360
aggactttag cagccttaga acattacttg gcttggagag ggcaagaagg tgaagctgta    420
ctggtgaaag ctctgaattg cagccaaggg acctactatc taaacgtcgc tgagaagaac    480
cacaacaacg aacagttcat ctacggttgg atcaagaatc gtgtgacc               528

<210> SEQ ID NO 66
<211> LENGTH: 528
<212> TYPE: DNA
<213> ORGANISM: unknown
<220> FEATURE:
<223> OTHER INFORMATION: Pseudin 1

<400> SEQUENCE: 66
aacccgatta tcgatggcat tatcgcgctg gaaggaggtt acgtctttaa tccgaaagat     60
aagggtggag caacacattg gggtattaca gaagcgacgg cacgagcaca tggttatgca    120
ggagacatgc gtgatctaac tcatgccgaa gcctacgcaa tacttgagga ggattactgg    180
atcaaaccgg gttttgatgt tatctcaacg ctgtcgtggc ctgtgagctt tgaattgtgt    240
gatgcagcgg ttaacatagg tgcataccac cctagtgcct ggttacagag atggcttaac    300
gtgttcaatc acgaaggcaa acgctatcca gacattcatg tagacggcaa cattggtccc    360
aggactttag cagccttaga acattacttg gcttggagag ggcaagaagg tgaagctgta    420
ctggtgaaag ctctgaattg cagccaaggg acctactatc taaacgtcgc tgagaagaac    480
cacaacaacg aacagttcat ctacggttgg atcaagaatc gtgtgacc               528

<210> SEQ ID NO 67
<211> LENGTH: 54
<212> TYPE: DNA
<213> ORGANISM: unknown
<220> FEATURE:
<223> OTHER INFORMATION: Ranalexin

<400> SEQUENCE: 67
ttcctgggcg gtctgattgt tccagctatg atctgtgcgg tgaccaaaaa atgc           54

<210> SEQ ID NO 68
<211> LENGTH: 102
```

```
<212> TYPE: DNA
<213> ORGANISM: unknown
<220> FEATURE:
<223> OTHER INFORMATION: Sushi 1

<400> SEQUENCE: 68
ggcttcaaac tgaaaggtat ggctcgtatc tcctgtctgc caaacggtca gtggtctaac     60
tttccaccga aatgcatccg tgaatgcgcg atggttagct ct                       102

<210> SEQ ID NO 69
<211> LENGTH: 81
<212> TYPE: DNA
<213> ORGANISM: unknown
<220> FEATURE:
<223> OTHER INFORMATION: WLBU2-Variant

<400> SEQUENCE: 69
aaacgctggg ttaaacgcgt gaaacgtgtc aaacgttggg tcaaacgtgt tgtccgtgta     60
gtgaaacgtt gggtgaaacg c                                              81

<210> SEQ ID NO 70
<211> LENGTH: 78
<212> TYPE: DNA
<213> ORGANISM: unknown
<220> FEATURE:
<223> OTHER INFORMATION: Melittin

<400> SEQUENCE: 70
ggtatcggtg ctgtgctgaa agttctgacc actggtctgc cggcactgat ttcttggatc     60
aaacgcaaac gtcagcag                                                  78

<210> SEQ ID NO 71
<211> LENGTH: 87
<212> TYPE: DNA
<213> ORGANISM: unknown
<220> FEATURE:
<223> OTHER INFORMATION: SMAP-29

<400> SEQUENCE: 71
cgtggtctgc gtcgcctggg tcgcaaaatt gcgcacggcg tcaaaaaata cggcccgacc     60
gtgctgcgca ttatccgcat cgctggt                                        87

<210> SEQ ID NO 72
<211> LENGTH: 75
<212> TYPE: DNA
<213> ORGANISM: unknown
<220> FEATURE:
<223> OTHER INFORMATION: Pleurocidin

<400> SEQUENCE: 72
ggctggggtt ctttctttaa aaaagcggct cacgttggca acatgtagg taaagcagct      60 ctgacccact atctg                                                     75

<210> SEQ ID NO 73
<211> LENGTH: 108
<212> TYPE: DNA
<213> ORGANISM: unknown
<220> FEATURE:
<223> OTHER INFORMATION: Cecropin A (A. aegypti)

<400> SEQUENCE: 73
ggcggcctga aaaaactggg caaaaaactg gaaggtgccg gcaaacgtgt gttcaacgct     60
```

```
gcagaaaaag cactgccggt tgtagctggt gctaaagctc tccgtaaa        108
```

<210> SEQ ID NO 74
<211> LENGTH: 120
<212> TYPE: DNA
<213> ORGANISM: unknown
<220> FEATURE:
<223> OTHER INFORMATION: Cecropin A (D. melanogaster)

<400> SEQUENCE: 74

```
ggctggctga aaaaaattgg caaaaaaatc gaacgcgtgg gccagcacac gcgtgatgca    60
accatccagg gtctgggtat cccacagcag gcagctaacg tagccgcgac tgctcgtggt   120
```

<210> SEQ ID NO 75
<211> LENGTH: 63
<212> TYPE: DNA
<213> ORGANISM: unknown
<220> FEATURE:
<223> OTHER INFORMATION: Buforin II

<400> SEQUENCE: 75

```
acccgtagct ctcgtgctgg cctgcagttt ccggttggtc gcgtgcaccg tctgctccgc    60
aaa                                                                 63
```

<210> SEQ ID NO 76
<211> LENGTH: 117
<212> TYPE: DNA
<213> ORGANISM: unknown
<220> FEATURE:
<223> OTHER INFORMATION: Sarcotoxin IA

<400> SEQUENCE: 76

```
ggatggctca aaagattgg caagaaaatc gagcgagtcg gtcagcatac gcgtgatgca    60
actatccagg gtttaggtat cgcacagcaa gcagctaatg tagcagctac tgctcgg     117
```

<210> SEQ ID NO 77
<211> LENGTH: 294
<212> TYPE: PRT
<213> ORGANISM: unknown
<220> FEATURE:
<223> OTHER INFORMATION: Pseudin 1-KZ144

<400> SEQUENCE: 77

```
Met Gly Leu Asn Thr Leu Lys Lys Val Phe Gln Gly Leu His Glu Ala
1               5                   10                  15

Ile Lys Leu Ile Asn Asn His Val Gln Gly Ser Lys Val Leu Arg Lys
            20                  25                  30

Gly Asp Arg Gly Asp Glu Val Cys Gln Leu Gln Thr Leu Leu Asn Leu
        35                  40                  45

Cys Gly Tyr Asp Val Gly Lys Pro Asp Gly Ile Phe Gly Asn Asn Thr
    50                  55                  60

Phe Asn Gln Val Val Lys Phe Gln Lys Asp Asn Cys Leu Asp Ser Asp
65                  70                  75                  80

Gly Ile Val Gly Lys Asn Thr Trp Ala Glu Leu Phe Ser Lys Tyr Ser
                85                  90                  95

Pro Pro Ile Pro Tyr Lys Thr Ile Pro Met Pro Thr Ala Asn Lys Ser
            100                 105                 110

Arg Ala Ala Ala Thr Pro Val Met Asn Ala Val Glu Asn Ala Thr Gly
        115                 120                 125

Val Arg Ser Gln Leu Leu Leu Thr Phe Ala Ser Ile Glu Ser Ala Phe
```

```
          130                 135                 140
Asp Tyr Glu Ile Lys Ala Lys Thr Ser Ser Ala Thr Gly Trp Phe Gln
145                 150                 155                 160

Phe Leu Thr Gly Thr Trp Lys Thr Met Ile Glu Asn Tyr Gly Met Lys
                165                 170                 175

Tyr Gly Val Leu Thr Asp Pro Thr Gly Ala Leu Arg Lys Asp Pro Arg
            180                 185                 190

Ile Ser Ala Leu Met Gly Ala Glu Leu Ile Lys Glu Asn Met Asn Ile
        195                 200                 205

Leu Arg Pro Val Leu Lys Arg Glu Pro Thr Asp Thr Asp Leu Tyr Leu
    210                 215                 220

Ala His Phe Phe Gly Pro Gly Ala Ala Arg Arg Phe Leu Thr Thr Gly
225                 230                 235                 240

Gln Asn Glu Leu Ala Ala Thr His Phe Pro Lys Glu Ala Gln Ala Asn
                245                 250                 255

Pro Ser Ile Phe Tyr Asn Lys Asp Gly Ser Pro Lys Thr Ile Gln Glu
            260                 265                 270

Val Tyr Asn Leu Met Asp Gly Lys Val Ala Ala His Arg Lys Leu Glu
        275                 280                 285

His His His His His His
    290

<210> SEQ ID NO 78
<211> LENGTH: 288
<212> TYPE: PRT
<213> ORGANISM: unknown
<220> FEATURE:
<223> OTHER INFORMATION: Ranalexin-KZ144

<400> SEQUENCE: 78

Met Phe Leu Gly Gly Leu Ile Val Pro Ala Met Ile Cys Ala Val Thr
1               5                   10                  15

Lys Lys Cys Gly Ser Lys Val Leu Arg Lys Gly Asp Arg Gly Asp Glu
                20                  25                  30

Val Cys Gln Leu Gln Thr Leu Leu Asn Leu Cys Gly Tyr Asp Val Gly
            35                  40                  45

Lys Pro Asp Gly Ile Phe Gly Asn Asn Thr Phe Asn Gln Val Val Lys
        50                  55                  60

Phe Gln Lys Asp Asn Cys Leu Asp Ser Asp Gly Ile Val Gly Lys Asn
65                  70                  75                  80

Thr Trp Ala Glu Leu Phe Ser Lys Tyr Ser Pro Pro Ile Pro Tyr Lys
                85                  90                  95

Thr Ile Pro Met Pro Thr Ala Asn Lys Ser Arg Ala Ala Ala Thr Pro
            100                 105                 110

Val Met Asn Ala Val Glu Asn Ala Thr Gly Val Arg Ser Gln Leu Leu
        115                 120                 125

Leu Thr Phe Ala Ser Ile Glu Ser Ala Phe Asp Tyr Glu Ile Lys Ala
    130                 135                 140

Lys Thr Ser Ser Ala Thr Gly Trp Phe Gln Phe Leu Thr Gly Thr Trp
145                 150                 155                 160

Lys Thr Met Ile Glu Asn Tyr Gly Met Lys Tyr Gly Val Leu Thr Asp
                165                 170                 175

Pro Thr Gly Ala Leu Arg Lys Asp Pro Arg Ile Ser Ala Leu Met Gly
            180                 185                 190

Ala Glu Leu Ile Lys Glu Asn Met Asn Ile Leu Arg Pro Val Leu Lys
```

```
                195                 200                 205
Arg Glu Pro Thr Asp Thr Asp Leu Tyr Leu Ala His Phe Phe Gly Pro
210                 215                 220
Gly Ala Ala Arg Arg Phe Leu Thr Thr Gly Gln Asn Glu Leu Ala Ala
225                 230                 235                 240
Thr His Phe Pro Lys Glu Ala Gln Ala Asn Pro Ser Ile Phe Tyr Asn
                245                 250                 255
Lys Asp Gly Ser Pro Lys Thr Ile Gln Glu Val Tyr Asn Leu Met Asp
            260                 265                 270
Gly Lys Val Ala Ala His Arg Lys Leu Glu His His His His His His
                275                 280                 285
```

<210> SEQ ID NO 79
<211> LENGTH: 306
<212> TYPE: PRT
<213> ORGANISM: unknown
<220> FEATURE:
<223> OTHER INFORMATION: Sushi1-KZ144

<400> SEQUENCE: 79

```
Ala Met Gly Gly Phe Lys Leu Lys Gly Met Ala Arg Ile Ser Cys Leu
1               5                   10                  15
Pro Asn Gly Gln Trp Ser Asn Phe Pro Pro Lys Cys Ile Arg Glu Cys
                20                  25                  30
Ala Met Val Ser Ser Gly Ser Lys Val Leu Arg Lys Gly Asp Arg Gly
            35                  40                  45
Asp Glu Val Cys Gln Leu Gln Thr Leu Leu Asn Leu Cys Gly Tyr Asp
        50                  55                  60
Val Gly Lys Pro Asp Gly Ile Phe Gly Asn Asn Thr Phe Asn Gln Val
65                  70                  75                  80
Val Lys Phe Gln Lys Asp Asn Cys Leu Asp Ser Asp Gly Ile Val Gly
                85                  90                  95
Lys Asn Thr Trp Ala Glu Leu Phe Ser Lys Tyr Ser Pro Pro Ile Pro
                100                 105                 110
Tyr Lys Thr Ile Pro Met Pro Thr Ala Asn Lys Ser Arg Ala Ala Ala
            115                 120                 125
Thr Pro Val Met Asn Ala Val Glu Asn Ala Thr Gly Val Arg Ser Gln
        130                 135                 140
Leu Leu Leu Thr Phe Ala Ser Ile Glu Ser Ala Phe Asp Tyr Glu Ile
145                 150                 155                 160
Lys Ala Lys Thr Ser Ser Ala Thr Gly Trp Phe Gln Phe Leu Thr Gly
                165                 170                 175
Thr Trp Lys Thr Met Ile Glu Asn Tyr Gly Met Lys Tyr Gly Val Leu
                180                 185                 190
Thr Asp Pro Thr Gly Ala Leu Arg Lys Asp Pro Arg Ile Ser Ala Leu
            195                 200                 205
Met Gly Ala Glu Leu Ile Lys Glu Asn Met Asn Ile Leu Arg Pro Val
        210                 215                 220
Leu Lys Arg Glu Pro Thr Asp Thr Asp Leu Tyr Leu Ala His Phe Phe
225                 230                 235                 240
Gly Pro Gly Ala Ala Arg Arg Phe Leu Thr Thr Gly Gln Asn Glu Leu
                245                 250                 255
Ala Ala Thr His Phe Pro Lys Glu Ala Gln Ala Asn Pro Ser Ile Phe
                260                 265                 270
Tyr Asn Lys Asp Gly Ser Pro Lys Thr Ile Gln Glu Val Tyr Asn Leu
```

```
                    275                 280                 285

Met Asp Gly Lys Val Ala Ala His Arg Lys Leu Glu His His His
    290                 295                 300

His His
305

<210> SEQ ID NO 80
<211> LENGTH: 297
<212> TYPE: PRT
<213> ORGANISM: unknown
<220> FEATURE:
<223> OTHER INFORMATION: WLBU2-Variant-KZ144

<400> SEQUENCE: 80

Met Lys Arg Trp Val Lys Arg Val Lys Arg Trp Val Lys
1               5                  10                  15

Arg Val Val Arg Val Val Lys Arg Trp Val Lys Arg Gly Ser Lys Val
                20                  25                  30

Leu Arg Lys Gly Asp Arg Gly Asp Glu Val Cys Gln Leu Gln Thr Leu
            35                  40                  45

Leu Asn Leu Cys Gly Tyr Asp Val Gly Lys Pro Asp Gly Ile Phe Gly
50                  55                  60

Asn Asn Thr Phe Asn Gln Val Val Lys Phe Gln Lys Asp Asn Cys Leu
65                  70                  75                  80

Asp Ser Asp Gly Ile Val Gly Lys Asn Thr Trp Ala Glu Leu Phe Ser
                85                  90                  95

Lys Tyr Ser Pro Pro Ile Pro Tyr Lys Thr Ile Pro Met Pro Thr Ala
            100                 105                 110

Asn Lys Ser Arg Ala Ala Ala Thr Pro Val Met Asn Ala Val Glu Asn
        115                 120                 125

Ala Thr Gly Val Arg Ser Gln Leu Leu Leu Thr Phe Ala Ser Ile Glu
130                 135                 140

Ser Ala Phe Asp Tyr Glu Ile Lys Ala Lys Thr Ser Ser Ala Thr Gly
145                 150                 155                 160

Trp Phe Gln Phe Leu Thr Gly Thr Trp Lys Thr Met Ile Glu Asn Tyr
                165                 170                 175

Gly Met Lys Tyr Gly Val Leu Thr Asp Pro Thr Gly Ala Leu Arg Lys
            180                 185                 190

Asp Pro Arg Ile Ser Ala Leu Met Gly Ala Glu Leu Ile Lys Glu Asn
        195                 200                 205

Met Asn Ile Leu Arg Pro Val Leu Lys Arg Glu Pro Thr Asp Thr Asp
210                 215                 220

Leu Tyr Leu Ala His Phe Phe Gly Pro Gly Ala Ala Arg Arg Phe Leu
225                 230                 235                 240

Thr Thr Gly Gln Asn Glu Leu Ala Ala Thr His Phe Pro Lys Glu Ala
                245                 250                 255

Gln Ala Asn Pro Ser Ile Phe Tyr Asn Lys Asp Gly Ser Pro Lys Thr
            260                 265                 270

Ile Gln Glu Val Tyr Asn Leu Met Asp Gly Lys Val Ala Ala His Arg
        275                 280                 285

Lys Leu Glu His His His His His His
    290                 295

<210> SEQ ID NO 81
<211> LENGTH: 296
<212> TYPE: PRT
```

<213> ORGANISM: unknown
<220> FEATURE:
<223> OTHER INFORMATION: Melttin-KZ144

<400> SEQUENCE: 81

Met Gly Ile Gly Ala Val Leu Lys Val Leu Thr Thr Gly Leu Pro Ala
1               5                   10                  15

Leu Ile Ser Trp Ile Lys Arg Lys Arg Gln Gln Gly Ser Lys Val Leu
            20                  25                  30

Arg Lys Gly Asp Arg Gly Asp Glu Val Cys Gln Leu Gln Thr Leu Leu
        35                  40                  45

Asn Leu Cys Gly Tyr Asp Val Gly Lys Pro Asp Gly Ile Phe Gly Asn
    50                  55                  60

Asn Thr Phe Asn Gln Val Val Lys Phe Gln Lys Asp Asn Cys Leu Asp
65                  70                  75                  80

Ser Asp Gly Ile Val Gly Lys Asn Thr Trp Ala Glu Leu Phe Ser Lys
                85                  90                  95

Tyr Ser Pro Pro Ile Pro Tyr Lys Thr Ile Pro Met Pro Thr Ala Asn
            100                 105                 110

Lys Ser Arg Ala Ala Ala Thr Pro Val Met Asn Ala Val Glu Asn Ala
        115                 120                 125

Thr Gly Val Arg Ser Gln Leu Leu Leu Thr Phe Ala Ser Ile Glu Ser
    130                 135                 140

Ala Phe Asp Tyr Glu Ile Lys Ala Lys Thr Ser Ser Ala Thr Gly Trp
145                 150                 155                 160

Phe Gln Phe Leu Thr Gly Thr Trp Lys Thr Met Ile Glu Asn Tyr Gly
                165                 170                 175

Met Lys Tyr Gly Val Leu Thr Asp Pro Thr Gly Ala Leu Arg Lys Asp
            180                 185                 190

Pro Arg Ile Ser Ala Leu Met Gly Ala Glu Leu Ile Lys Glu Asn Met
        195                 200                 205

Asn Ile Leu Arg Pro Val Leu Lys Arg Glu Pro Thr Asp Thr Asp Leu
    210                 215                 220

Tyr Leu Ala His Phe Gly Pro Gly Ala Ala Arg Arg Phe Leu Thr
225                 230                 235                 240

Thr Gly Gln Asn Glu Leu Ala Ala Thr His Phe Pro Lys Glu Ala Gln
                245                 250                 255

Ala Asn Pro Ser Ile Phe Tyr Asn Lys Asp Gly Ser Pro Lys Thr Ile
            260                 265                 270

Gln Glu Val Tyr Asn Leu Met Asp Gly Lys Val Ala Ala His Arg Lys
        275                 280                 285

Leu Glu His His His His His His
    290                 295

<210> SEQ ID NO 82
<211> LENGTH: 299
<212> TYPE: PRT
<213> ORGANISM: unknown
<220> FEATURE:
<223> OTHER INFORMATION: SMAP-29-KZ144

<400> SEQUENCE: 82

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

```
Lys Val Leu Arg Lys Gly Asp Arg Gly Asp Glu Val Cys Gln Leu Gln
             35                  40                  45

Thr Leu Leu Asn Leu Cys Gly Tyr Asp Val Gly Lys Pro Asp Gly Ile
 50                  55                  60

Phe Gly Asn Asn Thr Phe Asn Gln Val Val Lys Phe Gln Lys Asp Asn
 65                  70                  75                  80

Cys Leu Asp Ser Asp Gly Ile Val Gly Lys Asn Thr Trp Ala Glu Leu
                 85                  90                  95

Phe Ser Lys Tyr Ser Pro Pro Ile Pro Tyr Lys Thr Ile Pro Met Pro
                100                 105                 110

Thr Ala Asn Lys Ser Arg Ala Ala Ala Thr Pro Val Met Asn Ala Val
                115                 120                 125

Glu Asn Ala Thr Gly Val Arg Ser Gln Leu Leu Leu Thr Phe Ala Ser
130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Ala Leu
                180                 185                 190

Arg Lys Asp Pro Arg Ile Ser Ala Leu Met Gly Ala Glu Leu Ile Lys
            195                 200                 205

Glu Asn Met Asn Ile Leu Arg Pro Val Leu Lys Arg Glu Pro Thr Asp
210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
                260                 265                 270

Lys Thr Ile Gln Glu Val Tyr Asn Leu Met Asp Gly Lys Val Ala Ala
            275                 280                 285

His Arg Lys Leu Glu His His His His His His
            290                 295

<210> SEQ ID NO 83
<211> LENGTH: 306
<212> TYPE: PRT
<213> ORGANISM: unknown
<220> FEATURE:
<223> OTHER INFORMATION: Cecropin A (A.aegypti)-KZ144

<400> SEQUENCE: 83

Met Gly Gly Leu Lys Lys Leu Gly Lys Lys Leu Glu Gly Ala Gly Lys
 1               5                  10                  15

Arg Val Phe Asn Ala Ala Glu Lys Ala Leu Pro Val Val Ala Gly Ala
                 20                  25                  30

Lys Ala Leu Arg Lys Gly Ser Lys Val Leu Arg Lys Gly Asp Arg Gly
             35                  40                  45

Asp Glu Val Cys Gln Leu Gln Thr Leu Leu Asn Leu Cys Gly Tyr Asp
 50                  55                  60

Val Gly Lys Pro Asp Gly Ile Phe Gly Asn Asn Thr Phe Asn Gln Val
 65                  70                  75                  80

Val Lys Phe Gln Lys Asp Asn Cys Leu Asp Ser Asp Gly Ile Val Gly
                 85                  90                  95
```

```
Lys Asn Thr Trp Ala Glu Leu Phe Ser Lys Tyr Ser Pro Pro Ile Pro
                100                 105                 110

Tyr Lys Thr Ile Pro Met Pro Thr Ala Asn Lys Ser Arg Ala Ala Ala
            115                 120                 125

Thr Pro Val Met Asn Ala Val Glu Asn Ala Thr Gly Val Arg Ser Gln
130                 135                 140

Leu Leu Leu Thr Phe Ala Ser Ile Glu Ser Ala Phe Asp Tyr Glu Ile
145                 150                 155                 160

Lys Ala Lys Thr Ser Ser Ala Thr Gly Trp Phe Gln Phe Leu Thr Gly
                165                 170                 175

Thr Trp Lys Thr Met Ile Glu Asn Tyr Gly Met Lys Tyr Gly Val Leu
            180                 185                 190

Thr Asp Pro Thr Gly Ala Leu Arg Lys Asp Pro Arg Ile Ser Ala Leu
        195                 200                 205

Met Gly Ala Glu Leu Ile Lys Glu Asn Met Asn Ile Leu Arg Pro Val
210                 215                 220

Leu Lys Arg Glu Pro Thr Asp Thr Asp Leu Tyr Leu Ala His Phe Phe
225                 230                 235                 240

Gly Pro Gly Ala Ala Arg Arg Phe Leu Thr Thr Gly Gln Asn Glu Leu
                245                 250                 255

Ala Ala Thr His Phe Pro Lys Glu Ala Gln Ala Asn Pro Ser Ile Phe
            260                 265                 270

Tyr Asn Lys Asp Gly Ser Pro Lys Thr Ile Gln Glu Val Tyr Asn Leu
        275                 280                 285

Met Asp Gly Lys Val Ala Ala His Arg Lys Leu Glu His His His His
290                 295                 300

His His
305

<210> SEQ ID NO 84
<211> LENGTH: 295
<212> TYPE: PRT
<213> ORGANISM: unknown
<220> FEATURE:
<223> OTHER INFORMATION: Pleurocidin-KZ144

<400> SEQUENCE: 84

Met Gly Trp Gly Ser Phe Phe Lys Lys Ala Ala His Val Gly Lys His
1               5                   10                  15

Val Gly Lys Ala Ala Leu Thr His Tyr Leu Gly Ser Lys Val Leu Arg
            20                  25                  30

Lys Gly Asp Arg Gly Asp Glu Val Cys Gln Leu Gln Thr Leu Leu Asn
        35                  40                  45

Leu Cys Gly Tyr Asp Val Gly Lys Pro Asp Gly Ile Phe Gly Asn Asn
50                  55                  60

Thr Phe Asn Gln Val Val Lys Phe Gln Lys Asp Asn Cys Leu Asp Ser
65                  70                  75                  80

Asp Gly Ile Val Gly Lys Asn Thr Trp Ala Glu Leu Phe Ser Lys Tyr
                85                  90                  95

Ser Pro Pro Ile Pro Tyr Lys Thr Ile Pro Met Pro Thr Ala Asn Lys
            100                 105                 110

Ser Arg Ala Ala Ala Thr Pro Val Met Asn Ala Val Glu Asn Ala Thr
        115                 120                 125

Gly Val Arg Ser Gln Leu Leu Leu Thr Phe Ala Ser Ile Glu Ser Ala
130                 135                 140
```

```
Phe Asp Tyr Glu Ile Lys Ala Lys Thr Ser Ser Ala Thr Gly Trp Phe
145                 150                 155                 160

Gln Phe Leu Thr Gly Thr Trp Lys Thr Met Ile Glu Asn Tyr Gly Met
            165                 170                 175

Lys Tyr Gly Val Leu Thr Asp Pro Thr Gly Ala Leu Arg Lys Asp Pro
            180                 185                 190

Arg Ile Ser Ala Leu Met Gly Ala Glu Leu Ile Lys Glu Asn Met Asn
            195                 200                 205

Ile Leu Arg Pro Val Leu Lys Arg Glu Pro Thr Asp Thr Asp Leu Tyr
            210                 215                 220

Leu Ala His Phe Phe Gly Pro Gly Ala Ala Arg Arg Phe Leu Thr Thr
225                 230                 235                 240

Gly Gln Asn Glu Leu Ala Ala Thr His Phe Pro Lys Glu Ala Gln Ala
            245                 250                 255

Asn Pro Ser Ile Phe Tyr Asn Lys Asp Gly Ser Pro Lys Thr Ile Gln
            260                 265                 270

Glu Val Tyr Asn Leu Met Asp Gly Lys Val Ala Ala His Arg Lys Leu
            275                 280                 285

Glu His His His His His His
            290                 295

<210> SEQ ID NO 85
<211> LENGTH: 310
<212> TYPE: PRT
<213> ORGANISM: unknown
<220> FEATURE:
<223> OTHER INFORMATION: Cecropin A (D.melanogaster)-KZ144

<400> SEQUENCE: 85

Met Gly Trp Leu Lys Lys Ile Gly Lys Lys Ile Glu Arg Val Gly Gln
1               5                   10                  15

His Thr Arg Asp Ala Thr Ile Gln Gly Leu Gly Ile Pro Gln Gln Ala
            20                  25                  30

Ala Asn Val Ala Ala Thr Ala Arg Gly Gly Ser Lys Val Leu Arg Lys
            35                  40                  45

Gly Asp Arg Gly Asp Glu Val Cys Gln Leu Gln Thr Leu Leu Asn Leu
        50                  55                  60

Cys Gly Tyr Asp Val Gly Lys Pro Asp Gly Ile Phe Gly Asn Asn Thr
65                  70                  75                  80

Phe Asn Gln Val Val Lys Phe Gln Lys Asp Asn Cys Leu Asp Ser Asp
            85                  90                  95

Gly Ile Val Gly Lys Asn Thr Trp Ala Glu Leu Phe Ser Lys Tyr Ser
            100                 105                 110

Pro Pro Ile Pro Tyr Lys Thr Ile Pro Met Pro Thr Ala Asn Lys Ser
            115                 120                 125

Arg Ala Ala Thr Pro Val Met Asn Ala Val Glu Asn Ala Thr Gly
130                 135                 140

Val Arg Ser Gln Leu Leu Leu Thr Phe Ala Ser Ile Glu Ser Ala Phe
145                 150                 155                 160

Asp Tyr Glu Ile Lys Ala Lys Thr Ser Ser Ala Thr Gly Trp Phe Gln
            165                 170                 175

Phe Leu Thr Gly Thr Trp Lys Thr Met Ile Glu Asn Tyr Gly Met Lys
            180                 185                 190

Tyr Gly Val Leu Thr Asp Pro Thr Gly Ala Leu Arg Lys Asp Pro Arg
            195                 200                 205
```

-continued

```
Ile Ser Ala Leu Met Gly Ala Glu Leu Ile Lys Glu Asn Met Asn Ile
    210                 215                 220

Leu Arg Pro Val Leu Lys Arg Glu Pro Thr Asp Thr Asp Leu Tyr Leu
225                 230                 235                 240

Ala His Phe Phe Gly Pro Gly Ala Ala Arg Arg Phe Leu Thr Thr Gly
                245                 250                 255

Gln Asn Glu Leu Ala Ala Thr His Phe Pro Lys Glu Ala Gln Ala Asn
            260                 265                 270

Pro Ser Ile Phe Tyr Asn Lys Asp Gly Ser Pro Lys Thr Ile Gln Glu
                275                 280                 285

Val Tyr Asn Leu Met Asp Gly Lys Val Ala Ala His Arg Lys Leu Glu
290                 295                 300

His His His His His His
305                 310

<210> SEQ ID NO 86
<211> LENGTH: 291
<212> TYPE: PRT
<213> ORGANISM: unknown
<220> FEATURE:
<223> OTHER INFORMATION: BuforinII-KZ144

<400> SEQUENCE: 86

Met Thr Arg Ser Ser Arg Ala Gly Leu Gln Phe Pro Val Gly Arg Val
1               5                   10                  15

His Arg Leu Leu Arg Lys Gly Ser Lys Val Leu Arg Lys Gly Asp Arg
                20                  25                  30

Gly Asp Glu Val Cys Gln Leu Gln Thr Leu Leu Asn Leu Cys Gly Tyr
            35                  40                  45

Asp Val Gly Lys Pro Asp Gly Ile Phe Gly Asn Asn Thr Phe Asn Gln
50                  55                  60

Val Val Lys Phe Gln Lys Asp Asn Cys Leu Asp Ser Asp Gly Ile Val
65                  70                  75                  80

Gly Lys Asn Thr Trp Ala Glu Leu Phe Ser Lys Tyr Ser Pro Pro Ile
                85                  90                  95

Pro Tyr Lys Thr Ile Pro Met Pro Thr Ala Asn Lys Ser Arg Ala Ala
                100                 105                 110

Ala Thr Pro Val Met Asn Ala Val Glu Asn Ala Thr Gly Val Arg Ser
            115                 120                 125

Gln Leu Leu Leu Thr Phe Ala Ser Ile Glu Ser Ala Phe Asp Tyr Glu
130                 135                 140

Ile Lys Ala Lys Thr Ser Ser Ala Thr Gly Trp Phe Gln Phe Leu Thr
145                 150                 155                 160

Gly Thr Trp Lys Thr Met Ile Glu Asn Tyr Gly Met Lys Tyr Gly Val
                165                 170                 175

Leu Thr Asp Pro Thr Gly Ala Leu Arg Lys Asp Pro Arg Ile Ser Ala
            180                 185                 190

Leu Met Gly Ala Glu Leu Ile Lys Glu Asn Met Asn Ile Leu Arg Pro
        195                 200                 205

Val Leu Lys Arg Glu Pro Thr Asp Thr Asp Leu Tyr Leu Ala His Phe
210                 215                 220

Phe Gly Pro Gly Ala Ala Arg Arg Phe Leu Thr Thr Gly Gln Asn Glu
225                 230                 235                 240

Leu Ala Ala Thr His Phe Pro Lys Glu Ala Gln Ala Asn Pro Ser Ile
                245                 250                 255
```

Phe Tyr Asn Lys Asp Gly Ser Pro Lys Thr Ile Gln Glu Val Tyr Asn
            260                 265                 270

Leu Met Asp Gly Lys Val Ala Ala His Arg Lys Leu Glu His His His
        275                 280                 285

His His His
    290

<210> SEQ ID NO 87
<211> LENGTH: 309
<212> TYPE: PRT
<213> ORGANISM: unknown
<220> FEATURE:
<223> OTHER INFORMATION: Sarcotoxin IA-KZ144

<400> SEQUENCE: 87

Met Gly Trp Leu Lys Lys Ile Gly Lys Ile Glu Arg Val Gly Gln
1               5                   10                  15

His Thr Arg Asp Ala Thr Ile Gln Gly Leu Gly Ile Ala Gln Gln Ala
            20                  25                  30

Ala Asn Val Ala Ala Thr Ala Arg Gly Ser Lys Val Leu Arg Lys Gly
        35                  40                  45

Asp Arg Gly Asp Glu Val Cys Gln Leu Gln Thr Leu Leu Asn Leu Cys
50                  55                  60

Gly Tyr Asp Val Gly Lys Pro Asp Gly Ile Phe Gly Asn Asn Thr Phe
65                  70                  75                  80

Asn Gln Val Val Lys Phe Gln Lys Asp Asn Cys Leu Asp Ser Asp Gly
                85                  90                  95

Ile Val Gly Lys Asn Thr Trp Ala Glu Leu Phe Ser Lys Tyr Ser Pro
            100                 105                 110

Pro Ile Pro Tyr Lys Thr Ile Pro Met Pro Thr Ala Asn Lys Ser Arg
        115                 120                 125

Ala Ala Ala Thr Pro Val Met Asn Ala Val Glu Asn Ala Thr Gly Val
130                 135                 140

Arg Ser Gln Leu Leu Leu Thr Phe Ala Ser Ile Glu Ser Ala Phe Asp
145                 150                 155                 160

Tyr Glu Ile Lys Ala Lys Thr Ser Ser Ala Thr Gly Trp Phe Gln Phe
                165                 170                 175

Leu Thr Gly Thr Trp Lys Thr Met Ile Glu Asn Tyr Gly Met Lys Tyr
            180                 185                 190

Gly Val Leu Thr Asp Pro Thr Gly Ala Leu Arg Lys Asp Pro Arg Ile
        195                 200                 205

Ser Ala Leu Met Gly Ala Glu Leu Ile Lys Glu Asn Met Asn Ile Leu
210                 215                 220

Arg Pro Val Leu Lys Arg Glu Pro Thr Asp Thr Asp Leu Tyr Leu Ala
225                 230                 235                 240

His Phe Phe Gly Pro Gly Ala Ala Arg Arg Phe Leu Thr Thr Gly Gln
                245                 250                 255

Asn Glu Leu Ala Ala Thr His Phe Pro Lys Glu Ala Gln Ala Asn Pro
            260                 265                 270

Ser Ile Phe Tyr Asn Lys Asp Gly Ser Pro Lys Thr Ile Gln Glu Val
        275                 280                 285

Tyr Asn Leu Met Asp Gly Lys Val Ala Ala His Arg Lys Leu Glu His
290                 295                 300

His His His His His
305

```
<210> SEQ ID NO 88
<211> LENGTH: 226
<212> TYPE: PRT
<213> ORGANISM: unknown
<220> FEATURE:
<223> OTHER INFORMATION: Sarcotoxin IA-STM0016

<400> SEQUENCE: 88

Met Gly Trp Leu Lys Lys Ile Gly Lys Lys Ile Glu Arg Val Gly Gln
1               5                   10                  15

His Thr Arg Asp Ala Thr Ile Gln Gly Leu Gly Ile Ala Gln Gln Ala
            20                  25                  30

Ala Asn Val Ala Ala Thr Ala Arg Gly Ser Asn Pro Ile Ile Asp Gly
        35                  40                  45

Ile Ile Ala Leu Glu Gly Gly Tyr Val Phe Asn Pro Lys Asp Lys Gly
    50                  55                  60

Gly Ala Thr His Trp Gly Ile Thr Glu Ala Thr Ala Arg Ala His Gly
65                  70                  75                  80

Tyr Ala Gly Asp Met Arg Asp Leu Thr His Ala Glu Ala Tyr Ala Ile
                85                  90                  95

Leu Glu Glu Asp Tyr Trp Ile Lys Pro Gly Phe Asp Val Ile Ser Thr
            100                 105                 110

Leu Ser Trp Pro Val Ser Phe Glu Leu Cys Asp Ala Ala Val Asn Ile
        115                 120                 125

Gly Ala Tyr His Pro Ser Ala Trp Leu Gln Arg Trp Leu Asn Val Phe
    130                 135                 140

Asn His Glu Gly Lys Arg Tyr Pro Asp Ile His Val Asp Gly Asn Ile
145                 150                 155                 160

Gly Pro Arg Thr Leu Ala Ala Leu Glu His Tyr Leu Ala Trp Arg Gly
                165                 170                 175

Gln Glu Gly Glu Ala Val Leu Val Lys Ala Leu Asn Cys Ser Gln Gly
            180                 185                 190

Thr Tyr Tyr Leu Asn Val Ala Glu Lys Asn His Asn Asn Glu Gln Phe
        195                 200                 205

Ile Tyr Gly Trp Ile Lys Asn Arg Val Thr Leu Glu His His His His
    210                 215                 220

His His
225

<210> SEQ ID NO 89
<211> LENGTH: 216
<212> TYPE: PRT
<213> ORGANISM: unknown
<220> FEATURE:
<223> OTHER INFORMATION: SMAP-29-STM0016

<400> SEQUENCE: 89

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Asn Pro Ile Ile Asp Gly Ile Ile Ala Leu Glu Gly Gly Tyr Val Phe
        35                  40                  45

Asn Pro Lys Asp Lys Gly Gly Ala Thr His Trp Gly Ile Thr Glu Ala
    50                  55                  60

Thr Ala Arg Ala His Gly Tyr Ala Gly Asp Met Arg Asp Leu Thr His
65                  70                  75                  80
```

-continued

```
Ala Glu Ala Tyr Ala Ile Leu Glu Glu Asp Tyr Trp Ile Lys Pro Gly
                85                  90                  95

Phe Asp Val Ile Ser Thr Leu Ser Trp Pro Val Ser Phe Glu Leu Cys
            100                 105                 110

Asp Ala Ala Val Asn Ile Gly Ala Tyr His Pro Ser Ala Trp Leu Gln
            115                 120                 125

Arg Trp Leu Asn Val Phe Asn His Glu Gly Lys Arg Tyr Pro Asp Ile
130                 135                 140

His Val Asp Gly Asn Ile Gly Pro Arg Thr Leu Ala Ala Leu Glu His
145                 150                 155                 160

Tyr Leu Ala Trp Arg Gly Gln Glu Gly Glu Ala Val Leu Val Lys Ala
                165                 170                 175

Leu Asn Cys Ser Gln Gly Thr Tyr Tyr Leu Asn Val Ala Glu Lys Asn
            180                 185                 190

His Asn Asn Glu Gln Phe Ile Tyr Gly Trp Ile Lys Asn Arg Val Thr
            195                 200                 205

Leu Glu His His His His His His
        210                 215

<210> SEQ ID NO 90
<211> LENGTH: 247
<212> TYPE: PRT
<213> ORGANISM: unknown
<220> FEATURE:
<223> OTHER INFORMATION: SMAP-29-N4gp61

<400> SEQUENCE: 90

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Ala Ile Ser Lys Lys Lys Val Gly Gly Val Gly Gly Val Ile Ala Ala
        35                  40                  45

Ile Ile Ala Ala Val Phe Ala Val Glu Gly Gly Tyr Val Asn Asp Pro
50                  55                  60

Lys Asp Pro Gly Gly Glu Thr Asn His Gly Val Thr Ile Gln Val Ala
65                  70                  75                  80

Gln Lys His Lys Gln Glu Leu Glu Ser Met Tyr Asn Trp Asp Gly Ser
                85                  90                  95

Met Lys Asn Leu Thr Gln Glu Met Ala Ser Ser Ile Tyr Tyr Asn Asp
            100                 105                 110

Tyr Ile Leu Lys Pro Gly Phe Val Lys Phe Ala Asp Val Ser Pro Ala
            115                 120                 125

Val Thr Glu Lys Leu Val Asp Ala Gly Val Asn Thr Gly Pro Ala Arg
        130                 135                 140

Pro Ser Arg Trp Leu Gln Glu Ser Leu Asn Ala Phe Ser Arg Asn Gly
145                 150                 155                 160

Lys Asp Tyr Pro Lys Ile Gln Val Asp Gly Lys Val Gly Ser Gly Thr
                165                 170                 175

Leu Ser Ala Tyr Lys Ser Leu Gln Asn Lys Arg Gly Lys Val Glu Ala
            180                 185                 190

Cys Lys Leu Ile Leu Lys Ser Leu Asp Gly Lys Gln Leu Asn Tyr Tyr
        195                 200                 205

Leu Ser Leu Asn Met Pro Glu Tyr Thr Thr Gly Trp Ile Ala Asn Arg
210                 215                 220
```

Ile Gly Asn Val Pro Leu Glu Arg Cys Asn Glu Asp Ile Val Asn Leu
225                 230                 235                 240

Glu His His His His His
            245

<210> SEQ ID NO 91
<211> LENGTH: 624
<212> TYPE: DNA
<213> ORGANISM: unknown
<220> FEATURE:
<223> OTHER INFORMATION: N4gp61

<400> SEQUENCE: 91

```
atggccatct cgaagaaaaa agttggaggt gttggtggag ttattgcggc aatcattgct      60
gcagtatttg ccgttgaagg tggatacgtt aatgacccga agatccagg aggtgaaaca     120
aaccatggtg taactattca ggtcgcacaa aaacacaagc aagaacttga gtcgatgtat    180
aactgggacg ggtcaatgaa gaatctgaca caggagatgg cctcaagtat atattacaac    240
gattatatcc tcaagcctgg ctttgtgaaa tttgcggatg taagtccagc ggttacggaa    300
aaacttgtgg atgctggagt aaatacaggt ccagcaagac caagccgttg gttacaagaa    360
tccttgaatg ctttctcacg caacggcaaa gattatccga aaatccaagt tgacgggaaa    420
gtaggttctg gaactttgag tgcttacaaa agcctgcaga taagcgagg aaaagtggaa     480
gcctgcaaat taatactgaa gtctctggat ggcaagcagc taaactacta tctgagcctc    540
aatatgcctg agtataccac aggttggatt gcgaatcgta ttggaaatgt gcctttggaa    600
cgctgtaatg aagatatcgt caac                                           624
```

<210> SEQ ID NO 92
<211> LENGTH: 13
<212> TYPE: PRT
<213> ORGANISM: unknown
<220> FEATURE:
<223> OTHER INFORMATION: beta 4 helix

<400> SEQUENCE: 92

Pro Asn Arg Ala Lys Arg Val Ile Thr Thr Phe Arg Thr
1               5                   10

<210> SEQ ID NO 93
<211> LENGTH: 272
<212> TYPE: PRT
<213> ORGANISM: unknown
<220> FEATURE:
<223> OTHER INFORMATION: beta 4 helix:KZ144

<400> SEQUENCE: 93

Pro Asn Arg Ala Lys Arg Val Ile Thr Thr Phe Arg Thr Lys Val Leu
1               5                   10                  15

Arg Lys Gly Asp Arg Gly Asp Glu Val Cys Gln Leu Gln Thr Leu Leu
            20                  25                  30

Asn Leu Cys Gly Tyr Asp Val Gly Lys Pro Asp Gly Ile Phe Gly Asn
        35                  40                  45

Asn Thr Phe Asn Gln Val Val Lys Phe Gln Lys Asp Asn Cys Leu Asp
    50                  55                  60

Ser Asp Gly Ile Val Gly Lys Asn Thr Trp Ala Glu Leu Phe Ser Lys
65                  70                  75                  80

Tyr Ser Pro Pro Ile Pro Tyr Lys Thr Ile Pro Met Pro Thr Ala Asn
                85                  90                  95

```
Lys Ser Arg Ala Ala Ala Thr Pro Val Met Asn Ala Val Glu Asn Ala
                100                 105                 110
Thr Gly Val Arg Ser Gln Leu Leu Thr Phe Ala Ser Ile Glu Ser
            115                 120                 125
Ala Phe Asp Tyr Glu Ile Lys Ala Lys Thr Ser Ala Thr Gly Trp
        130                 135                 140
Phe Gln Phe Leu Thr Gly Thr Trp Lys Thr Met Ile Glu Asn Tyr Gly
145                 150                 155                 160
Met Lys Tyr Gly Val Leu Thr Asp Pro Thr Gly Ala Leu Arg Lys Asp
                165                 170                 175
Pro Arg Ile Ser Ala Leu Met Gly Ala Glu Leu Ile Lys Glu Asn Met
                180                 185                 190
Asn Ile Leu Arg Pro Val Leu Lys Arg Glu Pro Thr Asp Thr Asp Leu
                195                 200                 205
Tyr Leu Ala His Phe Phe Gly Pro Gly Ala Ala Arg Arg Phe Leu Thr
        210                 215                 220
Thr Gly Gln Asn Glu Leu Ala Ala Thr His Phe Pro Lys Glu Ala Gln
225                 230                 235                 240
Ala Asn Pro Ser Ile Phe Tyr Asn Lys Asp Gly Ser Pro Lys Thr Ile
                245                 250                 255
Gln Glu Val Tyr Asn Leu Met Asp Gly Lys Val Ala Ala His Arg Lys
                260                 265                 270

<210> SEQ ID NO 94
<211> LENGTH: 304
<212> TYPE: PRT
<213> ORGANISM: unknown
<220> FEATURE:
<223> OTHER INFORMATION: beta 4 helix:gp188

<400> SEQUENCE: 94

Pro Asn Arg Ala Lys Arg Val Ile Thr Thr Phe Arg Thr Asn Phe Arg
1               5                   10                  15
Thr Lys Asn Gly Tyr Arg Asp Leu Gln Ala Leu Val Lys Glu Leu Gly
                20                  25                  30
Leu Tyr Thr Gly Gln Ile Asp Gly Val Trp Gly Lys Gly Thr Ser Ser
            35                  40                  45
Ser Thr Glu Thr Leu Leu Arg Gly Tyr Ala Glu Val Val Gly Lys Asn
        50                  55                  60
Thr Gly Gly Ile Gly Leu Pro Thr Thr Ser Asp Ala Ser Gly Tyr Asn
65                  70                  75                  80
Val Ile Thr Ala Leu Gln Arg Asn Leu Ala Phe Leu Gly Leu Tyr Ser
                85                  90                  95
Leu Thr Val Asp Gly Ile Trp Gly Asn Gly Thr Leu Ser Gly Leu Asp
                100                 105                 110
Lys Ala Phe Glu Val Tyr Lys Glu Arg Tyr Arg Thr Pro Thr Tyr Asp
            115                 120                 125
Ile Ala Trp Ser Gly Lys Val Ser Pro Ala Phe Thr Ala Lys Val Lys
        130                 135                 140
Asp Trp Cys Gly Val His Val Pro Asn His Arg Ala Pro His Trp Leu
145                 150                 155                 160
Met Ala Cys Met Ala Phe Glu Thr Gly Gln Thr Phe Ser Pro Ser Ile
                165                 170                 175
Lys Asn Ala Ala Gly Ser Glu Ala Tyr Gly Leu Ile Gln Phe Met Ser
                180                 185                 190
```

Pro Ala Ala Asn Asp Leu Asn Val Pro Leu Ser Val Ile Arg Ser Met
        195                 200                 205

Asp Gln Leu Thr Gln Leu Asp Leu Val Phe Lys Tyr Phe Glu Met Trp
210                 215                 220

Met Lys Arg Gly Lys Arg Tyr Thr Gln Leu Glu Asp Phe Tyr Leu Thr
225                 230                 235                 240

Ile Phe His Pro Ala Ser Val Gly Lys Ala Asp Glu Val Leu Phe
                245                 250                 255

Leu Gln Gly Ser Lys Ala Tyr Leu Gln Asn Lys Gly Phe Asp Val Asp
                260                 265                 270

Lys Asp Gly Lys Ile Thr Leu Gly Glu Ile Ser Ser Thr Leu Tyr Thr
                275                 280                 285

Thr Tyr Tyr Lys Gly Leu Leu Pro Glu Asn Arg His Val Ile Ser Tyr
290                 295                 300

<210> SEQ ID NO 95
<211> LENGTH: 320
<212> TYPE: PRT
<213> ORGANISM: unknown
<220> FEATURE:
<223> OTHER INFORMATION: SMAP-29:gp188

<400> SEQUENCE: 95

Arg Gly Leu Arg Leu Gly Arg Lys Ile Ala His Gly Val Lys Lys
1               5                   10                  15

Tyr Gly Pro Thr Val Leu Arg Ile Ile Arg Ile Ala Gly Asn Phe Arg
                20                  25                  30

Thr Lys Asn Gly Tyr Arg Asp Leu Gln Ala Leu Val Lys Glu Leu Gly
            35                  40                  45

Leu Tyr Thr Gly Gln Ile Asp Gly Val Trp Gly Lys Gly Thr Ser Ser
50                  55                  60

Ser Thr Glu Thr Leu Leu Arg Gly Tyr Ala Glu Val Val Gly Lys Asn
65                  70                  75                  80

Thr Gly Gly Ile Gly Leu Pro Thr Thr Ser Asp Ala Ser Gly Tyr Asn
                85                  90                  95

Val Ile Thr Ala Leu Gln Arg Asn Leu Ala Phe Leu Gly Leu Tyr Ser
            100                 105                 110

Leu Thr Val Asp Gly Ile Trp Gly Asn Gly Thr Leu Ser Gly Leu Asp
            115                 120                 125

Lys Ala Phe Glu Val Tyr Lys Glu Arg Tyr Arg Thr Pro Thr Tyr Asp
130                 135                 140

Ile Ala Trp Ser Gly Lys Val Ser Pro Ala Phe Thr Ala Lys Val Lys
145                 150                 155                 160

Asp Trp Cys Gly Val His Val Pro Asn His Arg Ala Pro His Trp Leu
                165                 170                 175

Met Ala Cys Met Ala Phe Glu Thr Gly Gln Thr Phe Ser Pro Ser Ile
            180                 185                 190

Lys Asn Ala Ala Gly Ser Glu Ala Tyr Gly Leu Ile Gln Phe Met Ser
            195                 200                 205

Pro Ala Ala Asn Asp Leu Asn Val Pro Leu Ser Val Ile Arg Ser Met
210                 215                 220

Asp Gln Leu Thr Gln Leu Asp Leu Val Phe Lys Tyr Phe Glu Met Trp
225                 230                 235                 240

Met Lys Arg Gly Lys Arg Tyr Thr Gln Leu Glu Asp Phe Tyr Leu Thr
                245                 250                 255

```
Ile Phe His Pro Ala Ser Val Gly Lys Lys Ala Asp Glu Val Leu Phe
                260                 265                 270

Leu Gln Gly Ser Lys Ala Tyr Leu Gln Asn Lys Gly Phe Asp Val Asp
            275                 280                 285

Lys Asp Gly Lys Ile Thr Leu Gly Glu Ile Ser Ser Thr Leu Tyr Thr
290                 295                 300

Thr Tyr Tyr Lys Gly Leu Leu Pro Glu Asn Arg His Val Ile Ser Tyr
305                 310                 315                 320

<210> SEQ ID NO 96
<211> LENGTH: 330
<212> TYPE: PRT
<213> ORGANISM: unknown
<220> FEATURE:
<223> OTHER INFORMATION: Sarcotoxin IA:gp188

<400> SEQUENCE: 96

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg Asn Phe Arg Thr Lys Asn Gly Tyr Arg
        35                  40                  45

Asp Leu Gln Ala Leu Val Lys Glu Leu Gly Leu Tyr Thr Gly Gln Ile
50                  55                  60

Asp Gly Val Trp Gly Lys Gly Thr Ser Ser Thr Glu Thr Leu Leu
65                  70                  75                  80

Arg Gly Tyr Ala Glu Val Val Gly Lys Asn Thr Gly Gly Ile Gly Leu
                85                  90                  95

Pro Thr Thr Ser Asp Ala Ser Gly Tyr Asn Val Ile Thr Ala Leu Gln
            100                 105                 110

Arg Asn Leu Ala Phe Leu Gly Leu Tyr Ser Leu Thr Val Asp Gly Ile
        115                 120                 125

Trp Gly Asn Gly Thr Leu Ser Gly Leu Asp Lys Ala Phe Glu Val Tyr
130                 135                 140

Lys Glu Arg Tyr Arg Thr Pro Thr Tyr Asp Ile Ala Trp Ser Gly Lys
145                 150                 155                 160

Val Ser Pro Ala Phe Thr Ala Lys Val Lys Asp Trp Cys Gly Val His
                165                 170                 175

Val Pro Asn His Arg Ala Pro His Trp Leu Met Ala Cys Met Ala Phe
            180                 185                 190

Glu Thr Gly Gln Thr Phe Ser Pro Ser Ile Lys Asn Ala Ala Gly Ser
        195                 200                 205

Glu Ala Tyr Gly Leu Ile Gln Phe Met Ser Pro Ala Ala Asn Asp Leu
210                 215                 220

Asn Val Pro Leu Ser Val Ile Arg Ser Met Asp Gln Leu Thr Gln Leu
225                 230                 235                 240

Asp Leu Val Phe Lys Tyr Phe Glu Met Trp Met Lys Arg Gly Lys Arg
                245                 250                 255

Tyr Thr Gln Leu Glu Asp Phe Tyr Leu Thr Ile Phe His Pro Ala Ser
            260                 265                 270

Val Gly Lys Lys Ala Asp Glu Val Leu Phe Leu Gln Gly Ser Lys Ala
        275                 280                 285

Tyr Leu Gln Asn Lys Gly Phe Asp Val Asp Lys Asp Gly Lys Ile Thr
290                 295                 300
```

```
Leu Gly Glu Ile Ser Ser Thr Leu Tyr Thr Thr Tyr Tyr Lys Gly Leu
305                 310                 315                 320

Leu Pro Glu Asn Arg His Val Ile Ser Tyr
                325                 330

<210> SEQ ID NO 97
<211> LENGTH: 209
<212> TYPE: PRT
<213> ORGANISM: unknown
<220> FEATURE:
<223> OTHER INFORMATION: SMAP-29:Salmonella endolysin

<400> SEQUENCE: 97

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Lys Pro Lys
                20                  25                  30

Asp Glu Ile Phe Asp Glu Ile Leu Gly Lys Glu Gly Gly Tyr Val Asn
            35                  40                  45

His Pro Asp Asp Lys Gly Gly Pro Thr Lys Trp Gly Ile Thr Glu Lys
        50                  55                  60

Val Ala Arg Ala His Gly Tyr Arg Gly Asp Met Arg Asn Leu Thr Arg
65                  70                  75                  80

Gly Gln Ala Leu Glu Ile Leu Glu Thr Asp Tyr Trp Tyr Gly Pro Arg
                85                  90                  95

Phe Asp Arg Val Ala Lys Ala Ser Pro Asp Val Ala Ala Glu Leu Cys
            100                 105                 110

Asp Thr Gly Val Asn Met Gly Pro Ser Val Ala Ala Lys Met Leu Gln
        115                 120                 125

Arg Trp Leu Asn Val Phe Asn Gln Gly Gly Arg Leu Tyr Pro Asp Met
130                 135                 140

Asp Thr Asp Gly Arg Ile Gly Pro Arg Thr Leu Asn Ala Leu Arg Val
145                 150                 155                 160

Tyr Leu Glu Lys Arg Gly Lys Asp Gly Glu Arg Val Leu Leu Val Ala
                165                 170                 175

Leu Asn Cys Thr Gln Gly Glu Arg Tyr Leu Glu Leu Ala Glu Lys Arg
            180                 185                 190

Glu Ala Asp Glu Ser Phe Val Tyr Gly Trp Met Lys Glu Arg Val Leu
        195                 200                 205

Ile

<210> SEQ ID NO 98
<211> LENGTH: 303
<212> TYPE: PRT
<213> ORGANISM: unknown
<220> FEATURE:
<223> OTHER INFORMATION: Pseudin 1:Acinetobacter baumannii endolysin

<400> SEQUENCE: 98

Gly Leu Asn Thr Leu Lys Lys Val Phe Gln Gly Leu His Glu Ala Ile
1               5                   10                  15

Lys Leu Ile Asn Asn His Val Gln Glu Tyr Asp Met Ile Leu Lys Phe
                20                  25                  30

Gly Ser Lys Gly Asp Ala Val Ala Thr Leu Gln Lys Gln Leu Ala Lys
            35                  40                  45

Met Gly Tyr Lys Gly Val Lys Asp Lys Pro Leu Ser Val Asp Gly His
        50                  55                  60
```

```
Phe Gly Glu Ser Thr Glu Phe Ala Val Ile Gln Leu Gln Arg Lys Phe
 65                  70                  75                  80

Gly Leu Val Ala Asp Gly Lys Val Gly Asp Lys Thr Arg Gln Ala Leu
                 85                  90                  95

Ala Gly Asp Ser Val Ser Lys Phe Leu Lys Asp Glu Asp Tyr Lys Lys
                100                 105                 110

Ala Ala Ile Arg Leu Lys Val Pro Glu Leu Val Ile Arg Val Phe Gly
            115                 120                 125

Ala Val Glu Gly Leu Gly Val Gly Phe Leu Pro Asn Gly Lys Ala Lys
        130                 135                 140

Ile Leu Phe Glu Arg His Arg Met Tyr Phe Tyr Leu Cys Gln Ala Leu
145                 150                 155                 160

Gly Lys Thr Phe Ala Asn Ser Gln Val Lys Ile Thr Pro Asn Ile Val
                165                 170                 175

Asn Thr Leu Thr Gly Gly Tyr Lys Gly Asp Ala Ala Glu Tyr Thr Arg
                180                 185                 190

Leu Ser Met Ala Ile Asn Ile His Lys Glu Ser Ala Leu Met Ser Thr
            195                 200                 205

Ser Trp Gly Gln Phe Gln Ile Met Gly Glu Asn Trp Lys Asp Leu Gly
        210                 215                 220

Tyr Ser Ser Val Gln Glu Phe Val Asp Gln Gln Leu Asn Glu Gly
225                 230                 235                 240

Asn Gln Leu Glu Ala Phe Ile Arg Phe Ile Glu Trp Lys Pro Gly Leu
                245                 250                 255

Leu Glu Ala Leu Arg Lys Gln Asp Trp Asp Thr Val Phe Thr Leu Tyr
                260                 265                 270

Asn Gly Lys Asn Tyr Lys Lys Leu Gly Tyr Gln Ala Lys Phe Gln Lys
            275                 280                 285

Glu Trp Asp His Leu Glu Pro Ile Tyr Arg Glu Lys Thr Ala Ala
        290                 295                 300

<210> SEQ ID NO 99
<211> LENGTH: 308
<212> TYPE: PRT
<213> ORGANISM: unknown
<220> FEATURE:
<223> OTHER INFORMATION: SMAP-29: Acinetobacter baumannii endolysin

<400> SEQUENCE: 99

Arg Gly Leu Arg Arg Leu Gly Arg Lys Ile Ala His Gly Val Lys Lys
  1               5                  10                  15

Tyr Gly Pro Thr Val Leu Arg Ile Ile Arg Ile Ala Gly Glu Tyr Asp
                 20                  25                  30

Met Ile Leu Lys Phe Gly Ser Lys Gly Asp Ala Val Ala Thr Leu Gln
             35                  40                  45

Lys Gln Leu Ala Lys Met Gly Tyr Lys Gly Val Lys Asp Lys Pro Leu
         50                  55                  60

Ser Val Asp Gly His Phe Gly Glu Ser Thr Glu Phe Ala Val Ile Gln
 65                  70                  75                  80

Leu Gln Arg Lys Phe Gly Leu Val Ala Asp Gly Lys Val Gly Asp Lys
                 85                  90                  95

Thr Arg Gln Ala Leu Ala Gly Asp Ser Val Ser Lys Phe Leu Lys Asp
                100                 105                 110

Glu Asp Tyr Lys Lys Ala Ala Ile Arg Leu Lys Val Pro Glu Leu Val
            115                 120                 125
```

Ile Arg Val Phe Gly Ala Val Glu Gly Leu Gly Val Gly Phe Leu Pro
130                 135                 140

Asn Gly Lys Ala Lys Ile Leu Phe Glu Arg His Arg Met Tyr Phe Tyr
145                 150                 155                 160

Leu Cys Gln Ala Leu Gly Lys Thr Phe Ala Asn Ser Gln Val Lys Ile
                165                 170                 175

Thr Pro Asn Ile Val Asn Thr Leu Thr Gly Gly Tyr Lys Gly Asp Ala
            180                 185                 190

Ala Glu Tyr Thr Arg Leu Ser Met Ala Ile Asn Ile His Lys Glu Ser
        195                 200                 205

Ala Leu Met Ser Thr Ser Trp Gly Gln Phe Gln Ile Met Gly Glu Asn
    210                 215                 220

Trp Lys Asp Leu Gly Tyr Ser Ser Val Gln Glu Phe Val Asp Gln Gln
225                 230                 235                 240

Gln Leu Asn Glu Gly Asn Gln Leu Glu Ala Phe Ile Arg Phe Ile Glu
                245                 250                 255

Trp Lys Pro Gly Leu Leu Glu Ala Leu Arg Lys Gln Asp Trp Asp Thr
            260                 265                 270

Val Phe Thr Leu Tyr Asn Gly Lys Asn Tyr Lys Leu Gly Tyr Gln
        275                 280                 285

Ala Lys Phe Gln Lys Glu Trp Asp His Leu Glu Pro Ile Tyr Arg Glu
    290                 295                 300

Lys Thr Ala Ala
305

<210> SEQ ID NO 100
<211> LENGTH: 313
<212> TYPE: PRT
<213> ORGANISM: unknown
<220> FEATURE:
<223> OTHER INFORMATION: Sushi 1: Acinetobacter baumannii endolysin

<400> SEQUENCE: 100

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
                20                  25                  30

Ser Ser Glu Tyr Asp Met Ile Leu Lys Phe Gly Ser Lys Gly Asp Ala
            35                  40                  45

Val Ala Thr Leu Gln Lys Gln Leu Ala Lys Met Gly Tyr Lys Gly Val
        50                  55                  60

Lys Asp Lys Pro Leu Ser Val Asp Gly His Phe Gly Glu Ser Thr Glu
65                  70                  75                  80

Phe Ala Val Ile Gln Leu Gln Arg Lys Phe Gly Leu Val Ala Asp Gly
                85                  90                  95

Lys Val Gly Asp Lys Thr Arg Gln Ala Leu Ala Gly Asp Ser Val Ser
            100                 105                 110

Lys Phe Leu Lys Asp Glu Asp Tyr Lys Lys Ala Ala Ile Arg Leu Lys
        115                 120                 125

Val Pro Glu Leu Val Ile Arg Val Phe Gly Ala Val Glu Gly Leu Gly
    130                 135                 140

Val Gly Phe Leu Pro Asn Gly Lys Ala Lys Ile Leu Phe Glu Arg His
145                 150                 155                 160

Arg Met Tyr Phe Tyr Leu Cys Gln Ala Leu Gly Lys Thr Phe Ala Asn
                165                 170                 175

-continued

```
Ser Gln Val Lys Ile Thr Pro Asn Ile Val Asn Thr Leu Thr Gly Gly
            180                 185                 190

Tyr Lys Gly Asp Ala Ala Glu Tyr Thr Arg Leu Ser Met Ala Ile Asn
        195                 200                 205

Ile His Lys Glu Ser Ala Leu Met Ser Thr Ser Trp Gly Gln Phe Gln
    210                 215                 220

Ile Met Gly Glu Asn Trp Lys Asp Leu Gly Tyr Ser Ser Val Gln Glu
225                 230                 235                 240

Phe Val Asp Gln Gln Gln Leu Asn Glu Gly Asn Gln Leu Glu Ala Phe
                245                 250                 255

Ile Arg Phe Ile Glu Trp Lys Pro Gly Leu Leu Glu Ala Leu Arg Lys
            260                 265                 270

Gln Asp Trp Asp Thr Val Phe Thr Leu Tyr Asn Gly Lys Asn Tyr Lys
        275                 280                 285

Lys Leu Gly Tyr Gln Ala Lys Phe Gln Lys Glu Trp Asp His Leu Glu
        290                 295                 300

Pro Ile Tyr Arg Glu Lys Thr Ala Ala
305                 310
```